United States Patent
Arcot Desai et al.

(10) Patent No.: US 10,966,625 B2
(45) Date of Patent: Apr. 6, 2021

(54) SYSTEMS, DEVICES AND METHODS USING PHASE-AMPLITUDE COUPLING MEASURES IN IMPLANTABLE MEDICAL DEVICES

(71) Applicant: NeuroPace, Inc., Mountain View, CA (US)

(72) Inventors: Sharanya Arcot Desai, Sunnyvale, CA (US); Thomas K. Tcheng, Pleasant Hill, CA (US); Stephen T. Archer, Sunnyvale, CA (US)

(73) Assignee: NeuroPace, Inc., Mountain View, CA (US)

( * ) Notice: Subject to any disclaimer, the term of this patent is extended or adjusted under 35 U.S.C. 154(b) by 597 days.

(21) Appl. No.: 15/838,383

(22) Filed: Dec. 12, 2017

(65) Prior Publication Data

US 2019/0175040 A1    Jun. 13, 2019

(51) Int. Cl.
*A61B 5/04* (2006.01)
*A61B 5/048* (2006.01)
(Continued)

(52) U.S. Cl.
CPC .......... *A61B 5/048* (2013.01); *A61B 5/04017* (2013.01); *A61B 5/0478* (2013.01);
(Continued)

(58) Field of Classification Search
CPC ......... A61B 5/048; A61B 5/00; A61B 5/0478; A61B 5/686; A61B 5/04017;
(Continued)

(56) References Cited

U.S. PATENT DOCUMENTS 6,810,285 B2    10/2004 Pless et al.
8,190,270 B2    5/2012 Wingeier et al.
(Continued)

OTHER PUBLICATIONS

G. O'Leary, T. A. Valiante and R. Genov, "Low-latency VLSI architecture for neural cross-frequency coupling analysis," 2017 39th Annual International Conference of the IEEE Engineering in Medicine and Biology Society (EMBC), Seogwipo, 2017, pp. 2247-2250, doi: 10.1109/EMBC.2017.8037302. (Year: 2017).*
(Continued)

*Primary Examiner* — Eric J Messersmith
(74) *Attorney, Agent, or Firm* — Loza & Loza, LLP; David S. Sarisky

(57) ABSTRACT

A sensor of an implantable medical device senses electrical activity of the brain. A data analyzer of the device monitors an electrographic signal corresponding to the electrical activity of the sensed brain signal, and processes the brain signal to obtain a measure of phase-amplitude coupling. For a selected portion of the electrographic signal, the data analyzer detects first features and second features of the electrographic signal. The first features represent oscillations in a low frequency range, while the second features represent oscillations in a frequency range higher than the low frequency range. For example, the low frequency range may correspond to theta frequency and the higher frequency range may correspond to gamma frequency. The data analyzer determines a measure of phase-amplitude coupling between oscillations in the low frequency range and oscillations in the higher frequency range based on occurrences of second features which coincide with first features.

22 Claims, 20 Drawing Sheets

(51) Int. Cl.
*A61B 5/00* (2006.01)
*A61N 1/372* (2006.01)
*A61M 5/172* (2006.01)
*A61N 1/36* (2006.01)
*A61B 5/0478* (2006.01)
*A61N 1/05* (2006.01)

(52) U.S. Cl.
CPC ............ *A61B 5/4094* (2013.01); *A61B 5/686* (2013.01); *A61B 5/6868* (2013.01); *A61M 5/1723* (2013.01); *A61N 1/36139* (2013.01); *A61N 1/36171* (2013.01); *A61N 1/37229* (2013.01); *A61M 2210/0693* (2013.01); *A61M 2230/10* (2013.01); *A61N 1/0534* (2013.01); *A61N 1/36064* (2013.01); *A61N 1/36067* (2013.01)

(58) Field of Classification Search
CPC ............ A61B 5/6868; A61B 5/4094; A61M 2230/10; A61M 5/172; A61M 5/1723; A61M 2210/0693; A61N 1/05; A61N 1/36; A61N 1/372; A61N 1/36064; A61N 1/3606; A61N 1/36139; A61N 1/36171; A61N 1/37229; A61N 1/0534
See application file for complete search history.

(56) References Cited

U.S. PATENT DOCUMENTS

| | | | |
|---|---|---|---|
| 2014/0276181 A1 | 9/2014 | Sun et al. | |
| 2016/0331307 A1* | 11/2016 | Purdon | A61B 5/048 |
| 2017/0001016 A1* | 1/2017 | De Ridder | A61N 1/36135 |
| 2017/0049351 A1 | 2/2017 | Esteller | |
| 2017/0113046 A1* | 4/2017 | Fried | G16H 20/40 |
| 2017/0311870 A1* | 11/2017 | Bardakjian | A61B 5/4094 |
| 2020/0030608 A1* | 1/2020 | Halpern | A61N 1/36139 |

OTHER PUBLICATIONS

Avarado-Rojas et al. "Slow modulations of high-frequency activity (40-140-Hz) discriminate preictal changes in human focal epilepsy." Sci Rep 4:4545 (2014).

Axmacher et al., "Cross-frequency coupling supports multi-item working memory in the human hippocampus." Proc Natl.Acad Sci U.S.A. 107 (7):3228-3233 (2010.).

Canolty et al. "High Gamma Power Is Phase-Locked to Theta Oscillations in Human Neocortex." Science, vol. 313 (Sep. 15, 2006).

Canolty et al. "The functional role of cross-frequency coupling." Trends Cogn Sci 14 (11):506-515 (2010).

Hemptinne et al., "Exaggerated phase-amplitude coupling in the primary motor cortex in Parkinson disease." Proc Natl.Acad Sci U.S.A. 110 (12):4780-4785 (2013).

Roux et al. "Working memory and neural oscillations: alpha-gamma versus theta-gamma codes for distinct WM Information?." Trends Cogn Sci 18 (1):16-25 (2014).

Shirvalkar et al., Bidirectional changes to hippocampal theta-gamma comodulation predict memory for recent spatial episodes. Proc Natl.Acad Sci U.S.A. 107 (15):7054-7059 (2010).

Tort et al. Theta-gamma coupling increases during the learning of item-context associations. Proc Natl.Acad Sci U.S.A. 106 (49):20942-20947 (2009).

Tort et al. "Measuring Phase-Amplitude Coupling Between Neuronal Oscillations of Different Frequencies." J Neurophysiol 104: 1195-1210 (May 12, 2010).

* cited by examiner

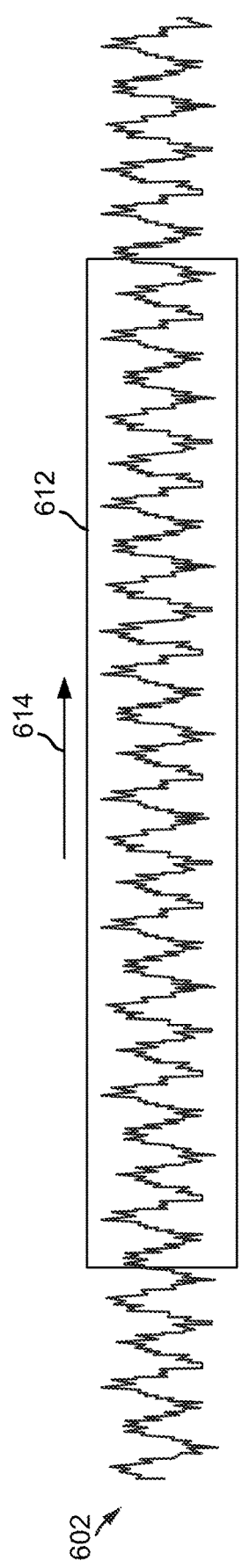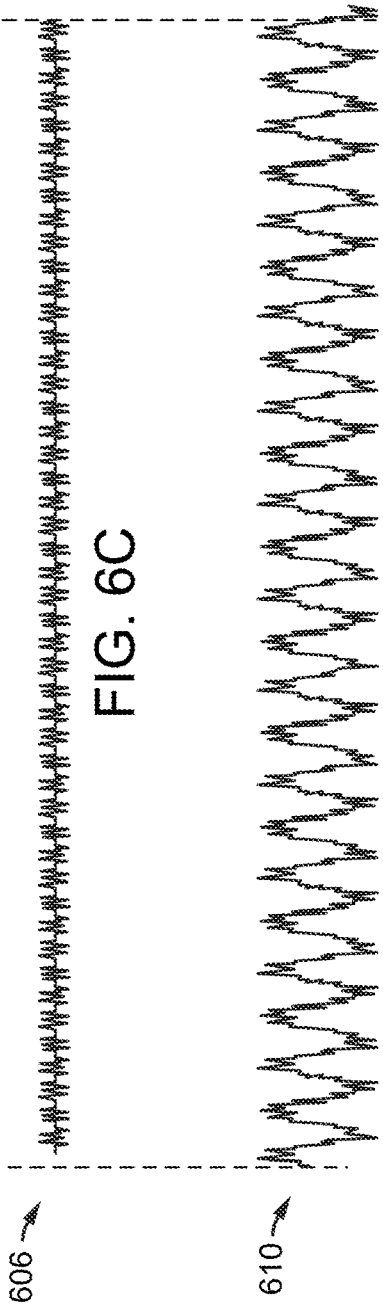

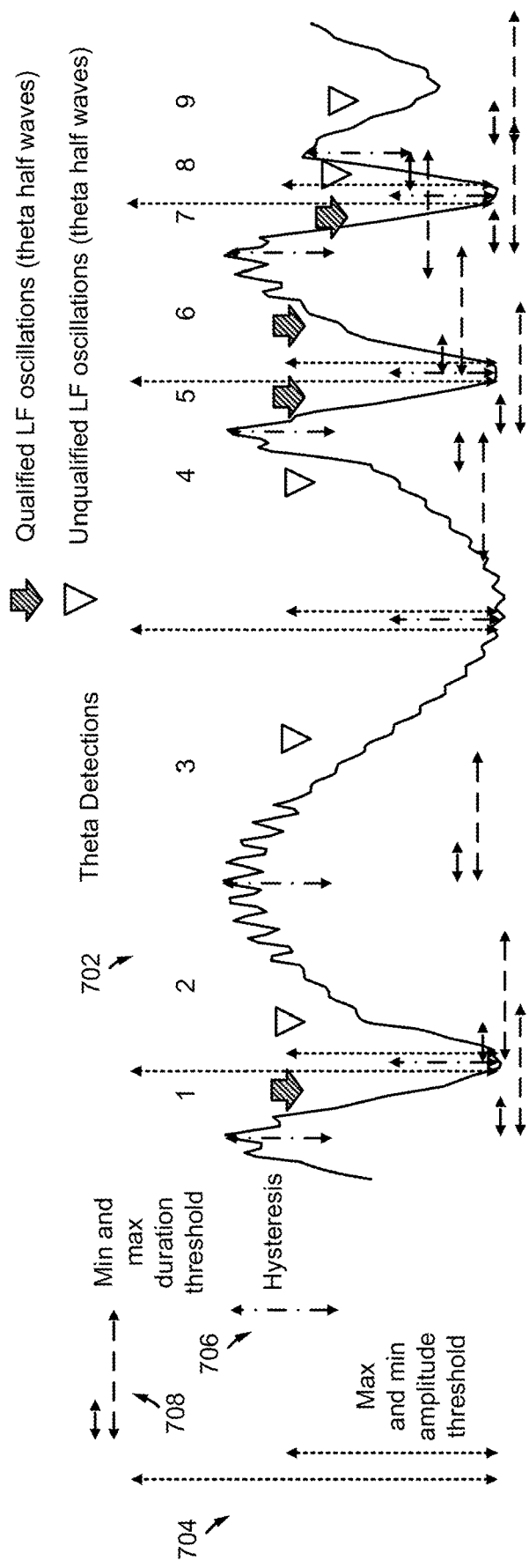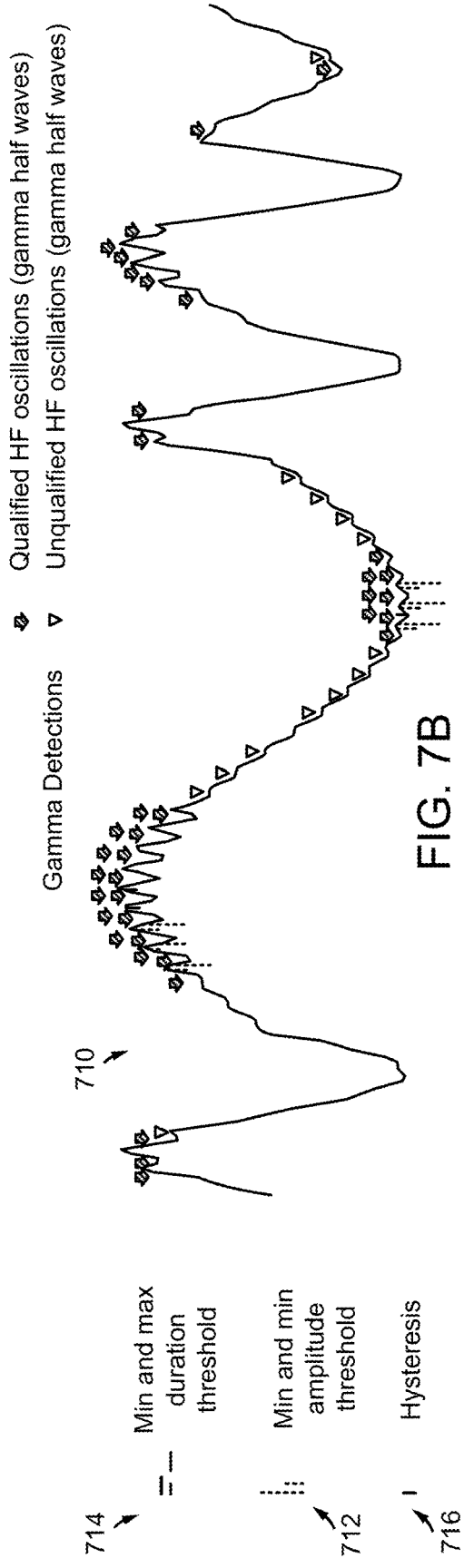
FIG. 7A
FIG. 7B

SYSTEMS, DEVICES AND METHODS USING PHASE-AMPLITUDE COUPLING MEASURES IN IMPLANTABLE MEDICAL DEVICES

BACKGROUND

Technical Field

The present disclosure relates to systems, devices, and methods for processing neuronal signals, and more particularly to systems including or devices comprising active implantable medical devices, and methods performed thereby, for computing measures of phase-amplitude coupling through analyses of intracranially-sensed brain signals.

Background

Neuronal oscillations of different frequencies can interact with one another. The interaction of oscillations in different frequency bands is commonly referred to as "cross-frequency coupling". In one type of cross-frequency coupling, known as "phase-amplitude coupling," the amplitude of high frequency oscillations is modulated by the phase of low-frequency oscillation. An example of phase-amplitude coupling is evident in certain neuronal oscillations of the hippocampus in the brain, where the phase of low frequency theta brain oscillations (where "low frequency" is between approximately 4 to 8 Hz), modulates the amplitude of high frequency gamma brain oscillations (where "high frequency" is generally greater than 40 Hz).

Several methods are known for assessing phase-amplitude coupling. In one technique described by Tort et al. in Measuring Phase-Amplitude Coupling Between Neuronal Oscillations of Different Frequencies, J Neurophysiol 104: 1195-1210, May 12, 2010, a sensed brain signal is filtered into two different frequency ranges, to obtain a low frequency brain signal and a high frequency brain signal. Using the standard Hilbert transform, a time series of phases is extracted from each of the low frequency brain signal and the high frequency brain signal. A composite time series is then constructed, which gives the amplitude of high frequency oscillations at each phase of the low frequency oscillations. A modulation index is derived from the composite time series. The index provides a measure of phase-amplitude coupling.

This technique of measuring phase-amplitude coupling, along with other existing techniques, can be computationally intensive, and generally requires the processing capability of an external computer (as opposed to being practical to carry out in a device implanted in a patient). (Processing performed on an external computer may be referred to herein as "offline" processing.) For reasons described more fully below, it may be desirable to measure phase-amplitude coupling in an implanted medical device. (Processing by an implantable medical device may be referred to herein as "online" processing.) Processing of data at the time it is being sensed, whether the processing is by an external computer or an implanted computer, may be referred to herein as "real time" processing. While technology continues to advance with respect to the potential computing power of implantable devices, and alternatives to a limited, on-device power source are the subject of research, design considerations for implanted devices still often limit the degree to which computationally intensive signal processing can be carried out in an implant (e.g., there are trade-offs between the power, memory and other resources required for the signal processing and other functions the implant is meant to perform).

Implantable medical devices are known that use algorithms of relatively low computational complexity to analyze activity within brain signals, and to determine when certain activity (e.g., patterns) should be deemed to have been detected by the device. One such algorithm involves identifying half waves in sensed brain signals that have been signal conditioned and otherwise processed by the implantable medical device. Half wave detection is a way of approximating the power of a signal in different frequency bands that is less computationally intensive than other methods of measuring the frequency content of a signal, such as Fast Fourier Transforms (FFTs) and Hilbert Transforms.

U.S. Pat. No. 6,810,285 to Pless et al. for "Seizure Sensing and Detection Using an Implantable Device" describes a half wave detector (also sometimes referred to as a half wave detection tool), for an implanted device (e.g., a neurostimulator). The implanted device can be configured so that the half wave detector is used alone or in combination with other forms of data analysis to decide whether some type of pre-defined neurological event has occurred. U.S. Patent Publication No. 2014/0276181 to Sun et al. for "Methods and Systems for Automatically Identifying Detection Parameters for an Implantable Medical Device" describes parameter sets for programming half wave detectors so that they can be tuned to identify the events of interest when they occur in the signals being monitored. U.S. Patent Publication No. 2017/0049351 to Rosana Esteller for "Neurological Event Detection Tools for Implantable Medical Devices" also describes various parameter sets for programming half wave detectors. Each of these patent documents is incorporated herein in its entirety by reference.

To date, algorithms of a low enough level of computational complexity to be practically implemented in an implantable medical device have not been applied to measure phase-amplitude coupling. Embodiments disclosed herein are directed to computing measures of phase-amplitude coupling, entirely or in significant part, in an implanted medical device. These measures may be computed by the implantable medical device in "real time" on brain signals being sensed by the device, or "online" by the device on records of brain signals previously sensed by the device and stored in device memory, or "offline" by an external device that obtains records of brain signals from the device memory. Also disclosed herein are various beneficial applications of such measures of phase-amplitude coupling with respect to certain neurological conditions or disorders, and their related brain states.

SUMMARY

In one embodiment, at least one sensor of an active implanted medical device senses electrical activity of the brain. A sensor may comprise one or more electrodes configured to sense field potential measurements corresponding to the electrical activity of a group of neurons. The device conditions and otherwise processes the sensed electrical activity to produce a digital representation of it—an electrographic signal (alternatively referred to herein as a brain signal or a waveform). The device can be configured to monitor electrical activity sensed from multiple sensors on one or more sensing channels. For example, the device can be configured so that the input from one sensor corresponds to a signal channel, or so that the input from one sensor corresponds to more than one channel, or so that the combined input from more than one sensor corresponds to a single channel.

A data analyzer of the device monitors the electrographic signal(s), and processes the electrographic signal(s) to obtain a measure of phase-amplitude coupling. The monitoring can be continuous, or substantially continuous, or accomplished according to a schedule or triggered by an event or events. The data analyzer is configured to, for a selected region of interest of each electrographic signal, detect different features. For example, the data analyzer may be configured to look for first features and second features in the region of interest. The first features may represent the content (or power) of the signal in one frequency range, while the second features may represent the content (or power) of the signal in a different frequency range. The frequencies in the second frequency range may be higher than those in the first frequency range. Analysis of these features may provide insight into the modulation of the amplitude of high frequency oscillations by the phase of low frequency oscillations, as described more fully herein.

For example, the first frequency range may correspond to frequencies in a low frequency range, such as the theta range (generally between about 4 Hz and 8 Hz) and the second frequency range may correspond to frequencies in a higher frequency range, such as the gamma range (generally above about 40 Hz). The first features and second features may correspond to the occurrence of one or more half waves in the signal that meet certain pre-determined criteria. To determine whether and, if so, when the pre-determined criteria are met, a first half wave detector or half wave tool is configured with parameter values that are tuned to identify first features, e.g., low-frequency features, based on pre-determined criteria, and a second half wave detector is configured with parameter values that are tuned to identify second features, e.g., higher-frequency features, based on pre-determined criteria. The data analyzer determines a measure of phase-amplitude coupling between the first features, e.g., the content of the electrographic signal in the region of interest in the first frequency range (such as theta), and the second features, e.g., the content of the electrographic signal in the region of interest in the second frequency range (such as gamma), based on where—and to what extent—the first features coincide with the second features.

Where the two features represent content of the signal in two different frequency ranges, determining phase-amplitude coupling between the two ranges may involve: (1) dividing the features (e.g., half waves) within the first or low frequency range into one or more portions, phases or phase bins, (2) assigning a designation (e.g., a phase range or phase bin number) to each portion, phase, or phase bin, (3) determining an individual metric for each portion, phase or phase bin corresponding to a measure (e.g. count) of features (e.g., half waves) within the second frequency range that coincides with the portion, phase or phase bin, and (4) aggregating the individual metrics on a per-phase-range or per-bin-number basis to obtain an aggregate metric that correlates to a degree (or a strength) of the phase-amplitude coupling between the two different frequency ranges for each assigned phase range or phase bin number. The aggregate metric may be a sum or statistical measure of individual metrics. A second aggregate metric is then computed across the different phase ranges or phase bin numbers of the low frequency range to derive a measure of the phase-amplitude coupling in the region of interest of the electrographic signal. This second aggregate metric corresponds to a measure of phase-amplitude coupling or a PAC score and provides an indication of the extent to which the amplitude of the higher frequency range in the electrographic signal has a preference to occur at selective phase(s) of the low frequency range in the electrographic signal.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein:

FIGS. 6A-6D illustrate a composite electrographic signal (FIG. 6A) and electrographic signals derived from the composite, namely, a theta-filtered electrographic signal (FIG. 6B), a gamma-filtered electrographic signal (FIG. 6C), and an electrographic signal comprising the coupling of the theta and gamma waves (FIG. 6D).

FIG. 7A-7B illustrate a method of analyzing a region of interest of an electrographic signal characterized by cross-frequency coupling, in which signal content or oscillations in a first frequency range (e.g. low-frequency, theta) is identified (FIG. 7A) and signal content or oscillations in a second frequency range (e.g., higher frequency, gamma) is identified (FIG. 7B).

DETAILED DESCRIPTION

Figure 1:
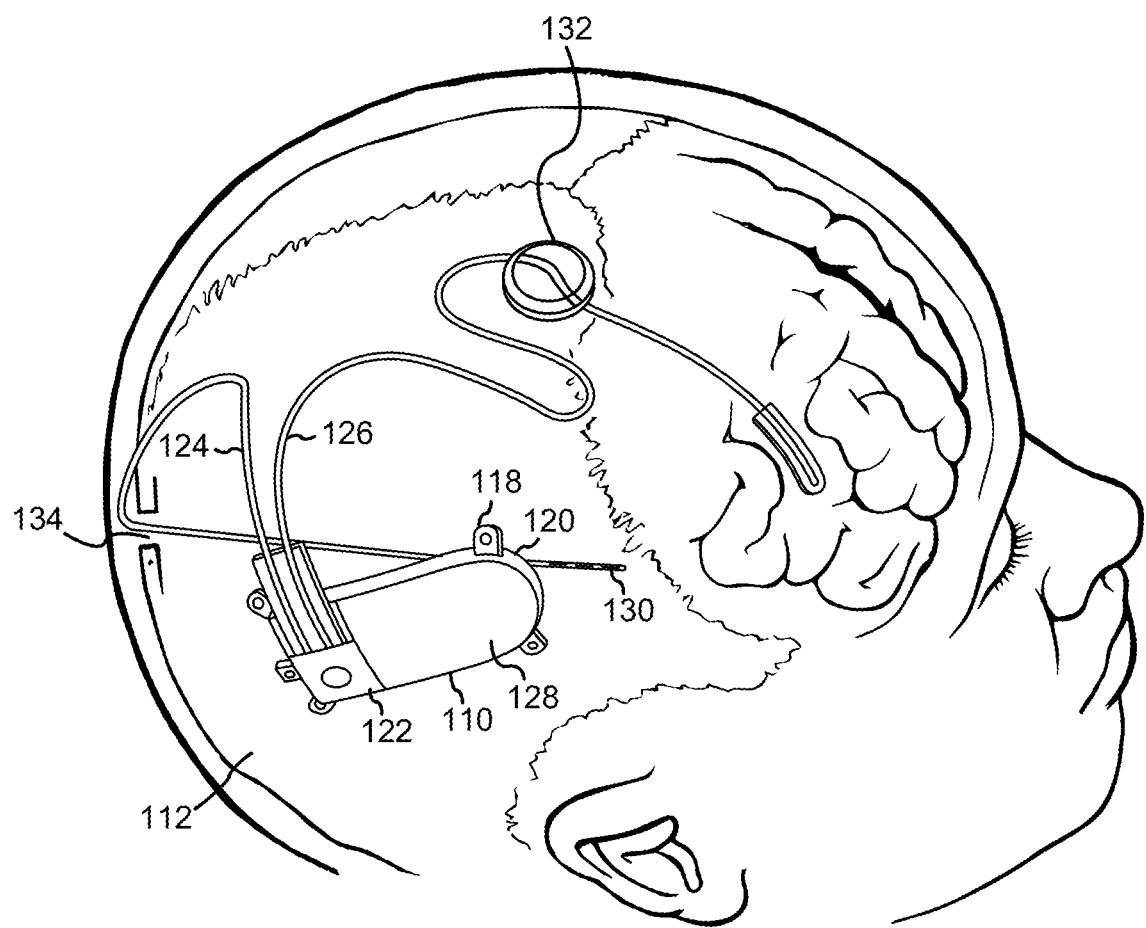
FIG. 1 is a perspective, schematic view of a patient's cranium in which implantable components are implanted, including an active medical device (e.g. a neurostimulator) and leads extending in or on the patient's brain configured to sense electrical activity from the patient's brain so that the activity can be monitored by the medical device.

Disclosed herein in detail is a method of calculating measures of phase-amplitude coupling in an active implantable medical device. The method analyzes electrographic signals in the time domain to approximate the power of the signal in a low frequency range and a higher frequency range by detecting oscillations in the electrographic signal in the low and higher frequency ranges. Once features in the low and higher frequency ranges are detected, the active implantable medical device processes information corresponding to the respective features to assign one or more phase ranges to the low frequency features, and to determine one or more metrics, e.g., individual counts and aggregate counts, with respect to the higher frequency features. The one or more metrics are further processed to compute a degree or strength of phase-amplitude coupling.

Prior to describing the foregoing method of computing measures of phase-amplitude coupling in an active implantable medical device in detail, an overview of phase-amplitude coupling in electrographic signals is provided, followed by an overview of an active implantable medical device that may be configured to implement the method.

Overview of Phase-Amplitude Coupling in Electrographic Signals

As used herein, the term "phase-amplitude coupling" refers to a measure derived from electrographic signals sensed from a subject's neural tissue in the brain that indicates whether and, if so, to what degree the phase of lower frequency components (or oscillations) of the signal modulate the amplitude of higher frequency components (or oscillations). The frequency components of the signal may be conveniently categorized in ranges, such as the following ranges: delta (approximately 1 to 4 Hz), theta (approximately 4 to 8 Hz), alpha (approximately 8 to 13 Hz), and beta (approximately 13 to 30 Hz), gamma (approximately 30 Hz to 80 Hz), and high gamma (greater than about 80 Hz).

As used herein the term "electrographic signal" refers to a signal that represents aggregate neuronal activity potentials (local field potentials or LFPs) detectable via electrodes. When the electrodes are applied to a patient's scalp, the signals acquired are usually referred to as an EEG. When the electrodes are applied intracranially, such as placed on or near the surface of the brain (e.g., on or near the dura mater) or within the brain (e.g., via depth electrodes), the signals acquired may be referred to as an ECoG (electrocorticogram) or ECoGs (electrocorticographic signals). Electrographic signals, EEG, and ECoGs may be referred to herein as brain signals or waveforms.

Studies have shown that phase-amplitude coupling serves important brain functions, for example, the presence or lack of phase-amplitude coupling is relevant to the brain's cognitive processing ability. R. T. Canolty and R. T. Knight. The functional role of cross-frequency coupling. *Trends Cogn Sci* 14 (11):506-515, 2010. It has been proposed that theta-gamma coupling electrographic signals is a mechanism by which information processing is coordinated across multiple spatiotemporal scales in the brain. R. T. Canolty and R. T. Knight. The functional role of cross-frequency coupling. *Trends Cogn Sci* 14 (11):506-515, 2010.

The degree (or strength) of phase-amplitude coupling may be correlated to a clinical state of the subject, or to a condition or disorder of the subject. For example, research suggests that the degree of phase-amplitude coupling between theta and gamma oscillations in sensed brain signals correlates with a subject's performance accuracy in memory tasks. A. B. Tort, R. W. Komorowski, J. R. Munns, N. J. Kopell, and H. Eichenbaum. Theta-gamma coupling increases during the learning of item-context associations. *Proc Natl. Acad Sci U.S.A.* 106 (49):20942-20947, 2009. In addition, in epilepsy, it is known that phase-amplitude coupling between the phase of delta activity (1-4 Hz) and the amplitude of high-frequency activity (40-140 Hz) increases around the time of the onset of a seizure. C. varado-Rojas, M. Valderrama, A. Fouad-Ahmed, H. Feldwisch-Drentrup, M. Isle, C. A. Teixeira, F. Sales, A. Schulze-Bondages, C. Adam, A. Dour ado, S. Charier, V. Navarro, and Quyen M. Le Van. Slow modulations of high-frequency activity (40-140-Hz) discriminate preictal changes in human focal epilepsy. *Sci Rep* 4:4545, 2014].

In other studies, electrical stimulation has successfully been applied to evoke cross frequency coupling in electrographic signals (neuronal oscillations) where it is absent or not present to a significant degree, with results shown to be beneficial in memory retrieval in rodents. P. R. Shirak, P. R. Rapp, and M. L. Shapiro. Bidirectional changes to hippocampal theta-gamma comodulation predict memory for recent spatial episodes. *Proc Natl. Acad Sci U.S.A.* 107 (15):7054-7059, 2010.

Phase-amplitude coupling between theta and gamma components of an electrographic signal is presently a commonly used measure in research. This measure represents how the phase of the lower frequency component (theta approximately 4 to 8 Hz) modulates the amplitude of the higher frequency component (gamma approximately 40 Hz to 80 Hz. A. B. Tort, R. W. Komorowski, J. R. Manns, N. J. Kopell, and H. Eichenbaum. Theta-gamma coupling increases during the learning of item-context associations.

Proc Natl. Acad Sci U.S.A. 106 (49):20942-20947, 2009; R. T. Canolty and R. T. Knight. The functional role of cross-frequency coupling. *Trends Cogn Sci* 14 (11):506-515, 2010. This form of phase-amplitude coupling may be referred to as "theta-gamma coupling" for short.

Several studies have shown that phase-amplitude coupling between the beta (approximately 13 to 30 Hz) and gamma components of an electrographic signal may be relevant in patients with the movement disorder Parkinson's disease ("beta-gamma coupling"). Hemptinne C. de, E. S. Ryapolova-Webb, E. L. Air, P. A. Garcia, K. J. Miller, J. G. Ojemann, J. L. Ostrem, N. B. Galifianakis, and P. A. Starr. Exaggerated phase-amplitude coupling in the primary motor cortex in Parkinson disease. *Proc Natl. Acad Sci U.S.A.* 110 (12):4780-4785, 2013.

Other examples of phase-amplitude coupling include "alpha-gamma coupling", where the phase of alpha (approximately 8 to 13 Hz) is measured with respect to the amplitude of gamma and "alpha-gamma coupling", where the phase of alpha is measured with respect to the amplitude of gamma (greater than about 40 Hz). F. Roux and P. J. Uhlhaas. Working memory and neural oscillations: alpha-gamma versus theta-gamma codes for distinct WM information? *Trends Cogn Sci* 18 (1):16-25, 2014; and "delta-beta coupling", where the phase of delta (approximately 1 to 4 Hz) is measured with respect to the amplitude of the beta. N. Axmacher, M. M. Henseler, O. Jensen, I. Weinreich, C. E. Elger, and J. Fell. Cross-frequency coupling supports multi-item working memory in the human hippocampus. *Proc Natl. Acad Sci U.S.A.* 107 (7):3228-3233, 2010.

Because it is currently a commonly sought measure, aspects of the following detailed description of methods for computing measures of phase-amplitude coupling in an active implantable medical device concerns theta-gamma coupling, it will be appreciated that the methods described may be extended to other types of cross-frequency coupling measurement, such as those identified above.

If phase-amplitude coupling in electrographic signals can be measured in real time or close to real time from a subject, the measure may be beneficially used in diagnosing a condition or disorder of a patient, or as an indicator of a state the patient's brain is in (e.g., a state that is prone to seizures, a state in which memory performance is optimized, etc.) Moreover, real time measurement of phase-amplitude coupling may be effective in driving therapeutic interventions (e.g., delivering electrical stimulation to reduce the severity of a seizure or to prevent one from developing at all) or sustaining a level of or evoking a level of cross frequency coupling that is deemed beneficial (e.g., to minimize a symptom of a movement disorder, such as tremor).

Real time measurements of phase-amplitude coupling desirably may be accomplished with one or more implantable components of a medical device system, so that the subject can remain ambulatory and not tied to external devices or components while the measurements are being undertaken. To minimize power requirements of the implantable components, and in light of other trade-offs important and common in the design of in implantable medical devices, the measurements beneficially may be carried out using an algorithm or algorithms of relatively low computational complexity.

Thus, disclosed herein is a method of calculating measures of phase-amplitude coupling in an active implantable medical device. The modifier "active" is used herein for convenience in this description to distinguish the implanted component of medical device system which is carrying out the calculations from other implanted components of the system, such as the leads that are conduits through which electrical activity sensed from the patient's brain is introduced to the implanted component carrying out the calculations. It will be appreciated, however that a given medical device system incorporating a method of measuring phase-amplitude coupling may include other implantable components that contain "active" components inasmuch as they may include and use active electronics to acquire measurements (e.g., an active lead) or to deliver a therapy (e.g., a separate implantable system component configured to deliver electrical stimulation or some other form of treatment intended to modulate neural function in the brain).

The method analyzes electrographic signals in the time domain to approximate the power of the signal in a low frequency range and a higher frequency range by detecting features, e.g., oscillations, in the electrographic signal in the low and higher frequency ranges using a half wave detector or half wave detection tool. For example, the implantable medical device may include two half wave detectors, one tuned for the low frequency and the other tuned for the higher frequency, where each detector is programmed to detect half waves that satisfy certain amplitude, duration, and hysteresis criteria indicative of the low or higher frequency range, respectively. When the method is used to measure theta-gamma coupling, the low frequency half wave detector may be tuned to detect half waves corresponding to the 4 to 8 Hz range, and the higher frequency half wave detector may be tuned to detect half waves corresponding to 40 Hz and above.

Once the half wave detectors have detected features in the low and higher frequency ranges, the active implantable medical device processes information corresponding to the respective features to assign one or more phase ranges to the low frequency feature, and to determine one or more metrics, e.g., individual counts and aggregate counts, with respect to the higher frequency features. The one or more metrics are further processed to compute a degree or strength of phase-amplitude coupling.

Overview of the Active Implantable Medical Device

Embodiments of an active implantable medical device that can be configured to implement the method, and a system including it, are now described with references to FIGS. 1-4.

FIG. 1 is an illustration of the implantable components of a medical device system according to embodiments, namely, an active implantable neurostimulator 110 and two electrode-bearing brain leads 124, 126, implanted in a patient. The neurostimulator 110 is affixed in the patient's cranium 112 by way of a ferrule 118. The ferrule 118 is a structural member adapted to fit into a cranial opening, attach to the cranium 112, and retain the neurostimulator 110. To implant the neurostimulator 110, a craniotomy is performed in the parietal bone anterior to the lambdoidal suture to define an opening 120 slightly larger than the neurostimulator 110. The ferrule 118 is inserted into the opening 120 and affixed to the cranium 112, ensuring a tight and secure fit. The neurostimulator 110 is then inserted into and affixed to the ferrule 118.

The neurostimulator 110 includes a lead connector 122 adapted to receive one or more of the brain leads, such as a deep brain or depth lead 124 and a cortical strip lead 126. (The depth lead is intended to be implanted so that a distal end of it is situated within the patient's neural tissue, whereas the cortical strip lead is intended to be implanted under the dura mater so that a distal end of it rests on a surface of the brain). The lead connector 122 acts to physically secure the brain leads 124, 126 to the neurostimulator 110, and facilitates electrical connection to conductors in the brain leads 124, 126 coupling one or more electrodes at or near a distal end of the lead to circuitry within the neurostimulator 110. The lead connector 122 accomplishes this in a substantially fluid-tight environment with biocompatible materials.

More particularly, the brain leads 124, 126 include a flexible elongated member having one or more conductors. As shown, the brain leads 124, 126 are coupled to the neurostimulator 110 via the lead connector 122. The proximal portion of the deep brain lead 124 is generally situated on the outer surface of the cranium 112 (and under the patient's scalp), and extends between the neurostimulator 110 and a burr hole 134 or other cranial opening. The distal portion of the deep brain lead 124 enters the cranium 112 and is coupled to at least one depth electrode 130 implanted in a desired location in the patient's brain. The proximal portion of the cortical lead 126 is generally situated on the outer surface of the cranium 112 (and under the patient's scalp), and extends between the neurostimulator 110 and a burr hole (not visible) or other cranial opening. The distal portion of the cortical lead 126 enters the cranium 112 through the burr hole and is secured in place by a burr hole cover 132. The distal portion of the cortical lead 126 includes at least one cortical electrode (not visible) implanted in a desired location on the patient's brain.

The neurostimulator 110 includes a durable housing 128 fabricated from a biocompatible material, such as titanium. As the neurostimulator 110 is self-contained, the housing 128 encloses a battery and any electronic circuitry necessary or desirable to provide the functionality described herein, as well as any other features. A telemetry coil or other antenna may be provided outside of the housing 128 (and potentially integrated with the lead connector 122) to facilitate communication between the neurostimulator 110 and external devices.

Figure 2:
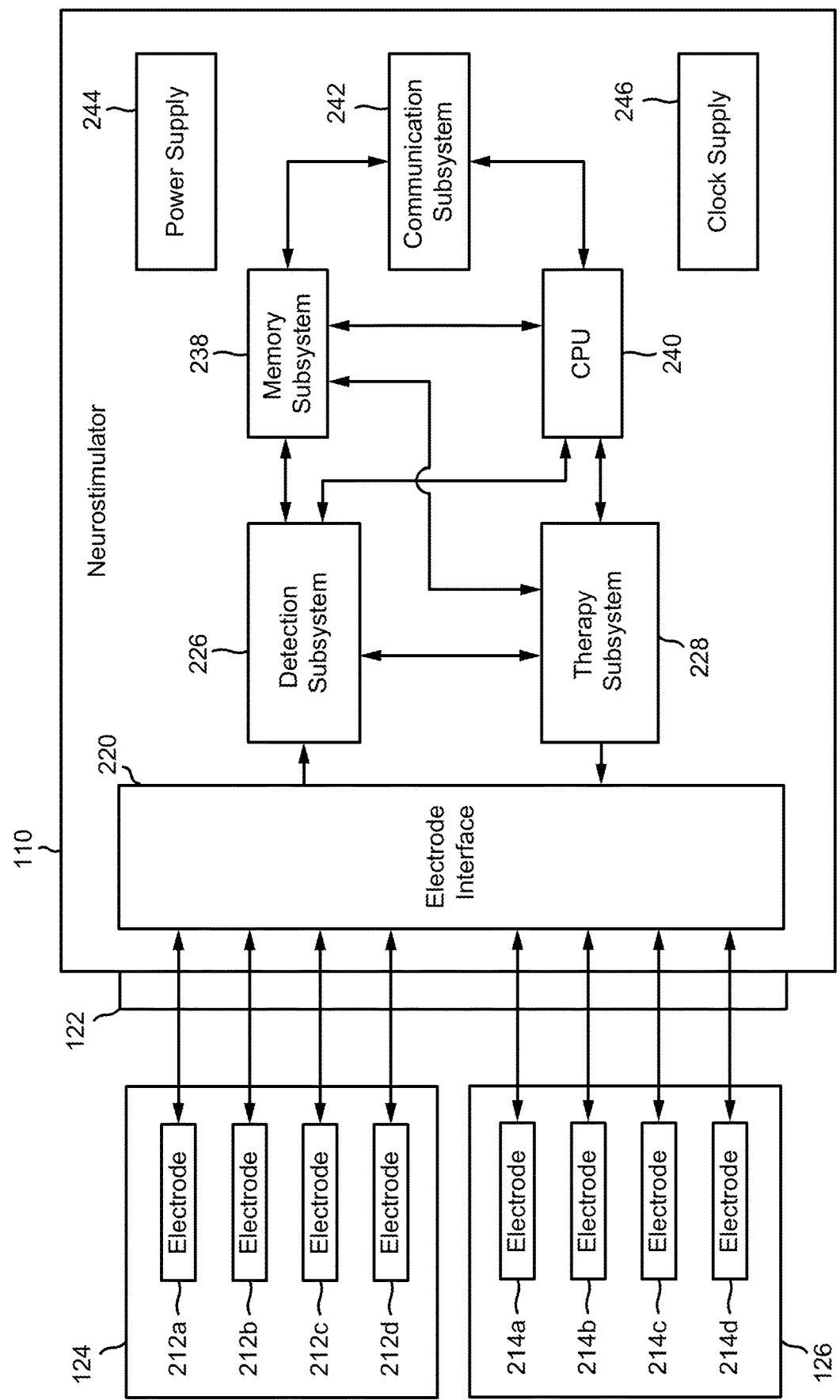
FIG. 2 is a block diagram of the active medical device (e.g. a neurostimulator) and leads of FIG. 1, illustrating some of the functional subsystems of the active medical device.

FIG. 2 is a block diagram of a medical device system including an active implantable neurostimulator 110 and two brain leads 124, 126, each bearing four electrodes 212a-d, 214a-d. The neurostimulator 110 may be configured to compute measures of phase-amplitude coupling in accordance with the techniques disclosed herein. The neurostimulator 110 may be further configured to process the measures of phase-amplitude coupling for purposes of driving therapeutic interventions in accordance with techniques disclosed herein.

The neurostimulator 110 includes a lead connector 122 adapted to receive a connector end of each brain lead 124, 126, to thereby electrically couple each lead and its associated electrodes 212a-d, 214a-d with the neurostimulator. The neurostimulator 110 may configure an electrode 212a-d, 214a-d as either a sensor (for purposes of sensing electrical activity of the brain, which activity is subsequently processed by other components of the neuro stimulator for purposes of computing measures of phase-amplitude coupling) or a stimulator (for purposes of delivering therapy to the patient in the form of electrical stimulation, which delivery may be in response to computed measures of phase-amplitude coupling) or both. Although eight electrodes 212a-d, 214a-d are shown in FIG. 2, more electrodes may be available depending on the number of implanted leads and the number of electrodes per lead.

The electrodes 212a-d, 214a-d are connected to an electrode interface 220. The electrode interface 220 is capable of selecting each electrode 212a-d, 214a-d as required for sensing and stimulation. The electrode interface 220 may also provide any other features, capabilities, or aspects, including but not limited to amplification, isolation, and charge-balancing functions, that are required for a proper interface with neurological tissue. The electrode interface 220 is coupled to a detection subsystem 226, which is configured to process electrical activity of the brain sensed through the electrode 212a-d, 214a-d to compute measures of phase-amplitude coupling. Details of the detection subsystem 226 are described later below with references to FIG. 3. The electrode interface 220 may also be coupled to a therapy subsystem 228, which is configured to deliver therapy to the patient through the electrode 212a-d, 214a-d in the form of electrical stimulation.

The neurostimulator 110 includes a memory subsystem 238 and a central processing unit (CPU) 240, which can take the form of a microcontroller. The memory subsystem 238 is coupled to the detection subsystem 226, and may receive and store data representative of sensed electrographic signals, measures of phase-amplitude coupling, and other sensor data. The memory subsystem 238 is also coupled to the therapy subsystem 228 and the CPU 240. In addition to the memory subsystem 238, the CPU 240 is also connected to the detection subsystem 226 and the therapy subsystem 228 for direct control of those subsystems.

The neurostimulator 110 also includes a communication subsystem 242. The communication subsystem 242 enables communication between the neurostimulator 110 and the outside world, such as an external programmer, through a wireless communication link. The programmer allows the physician to read out a history of events detected including electrographic signal information before, during, and after each neurological event, as well as specific information relating to the detection of each event. Information related to measures of phase-amplitude coupling may also be read from the neurostimulator 110. The neurostimulator 110 also includes a power supply 244 and a clock supply 246. The power supply 244 supplies the voltages and currents necessary for each of the other subsystems. The clock supply 246 supplies substantially all the other subsystems with any clock and timing signals necessary for their operation.

Figure 3:
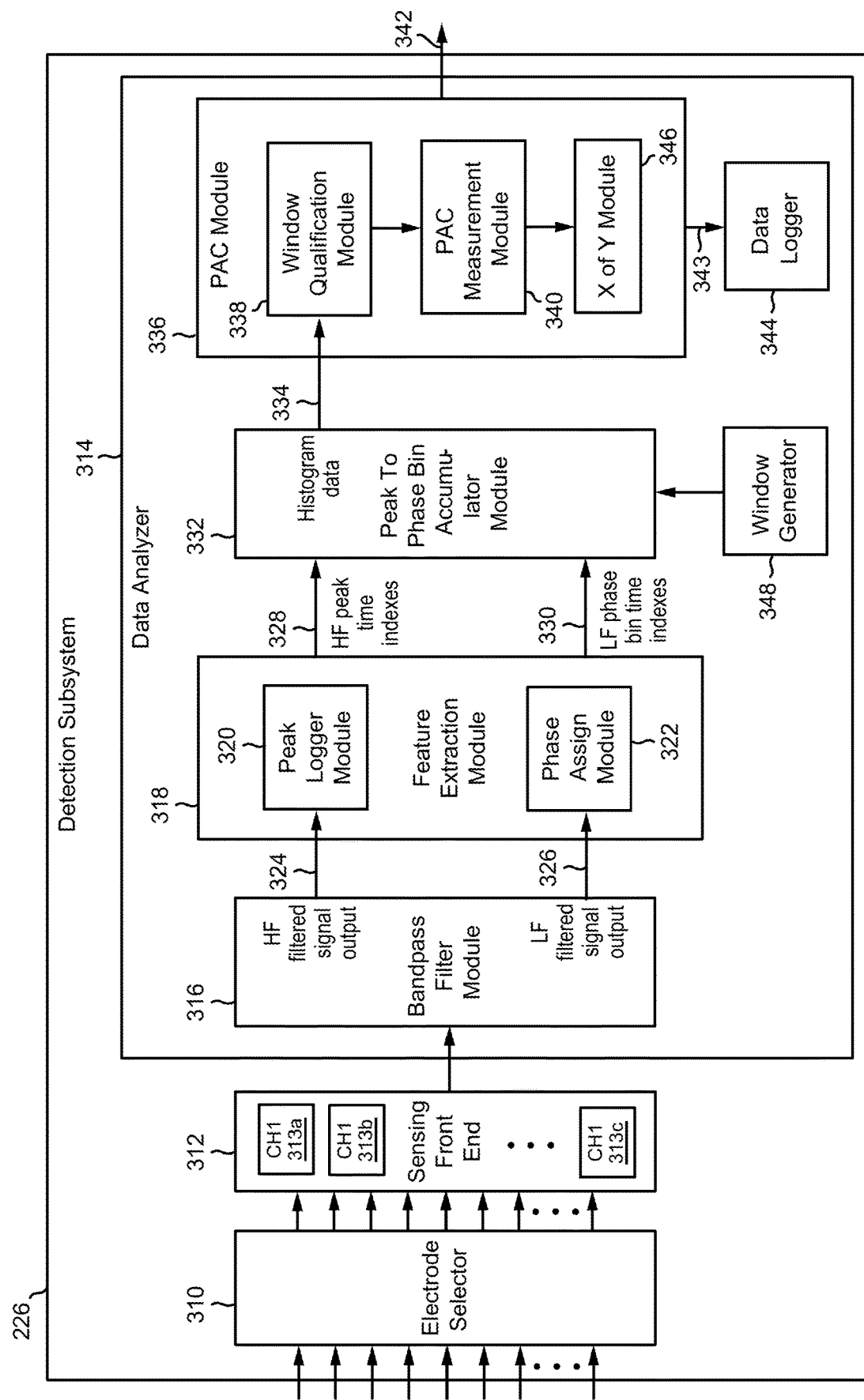
FIG. 3 is a block diagram of the detection subsystem of FIG. 2, illustrating some of its functional components.

FIG. 3 illustrates details of the detection subsystem 226 of FIG. 2. Signals received from the electrodes 212a-d, 214a-d are received in an electrode selector 310. The electrode selector 310 allows the device to select which electrodes 212a-d, 214a-d should be routed to which individual sensing channels 313a, 313b, 313c associated with the sensing front end 312.

The electrode selector 310 provides signals corresponding to each pair of selected electrodes to the sensing front end 312, which performs amplification, analog to digital conversion, and multiplexing functions on the signals in the sensing channels 313a, 313b, 313c. Preferably, any of the electrodes 212a-d, 214a-d can be unused (i.e., not connected to any sensing channel), coupled to a positive or negative input of a single sensing channel, coupled to the positive inputs of multiple sensing channels, or coupled to the negative inputs of multiple sensing channels.

A multiplexed input signal representative of all active sensing channels 313a, 313b, 313c is fed from the sensing front end 312 to a data analyzer 314. The data analyzer 314 may be a special-purpose digital signal processor (DSP) adapted for use in some embodiments, or in some alternative embodiments, may comprise a programmable general-purpose DSP.

In accordance with embodiments disclosed herein, the data analyzer 314 includes modules configured to perform functions related to computing measures of phase-amplitude coupling. In an example configuration, the data analyzer 314 includes a bandpass filter 316 that includes one or more individual bandpass filters, a feature extraction module 318 that includes a peak logger 320 and a phase assignment module 322, a peak-to-phase accumulator 332, and a phase-amplitude coupling (PAC) module 336.

Figure 4A:
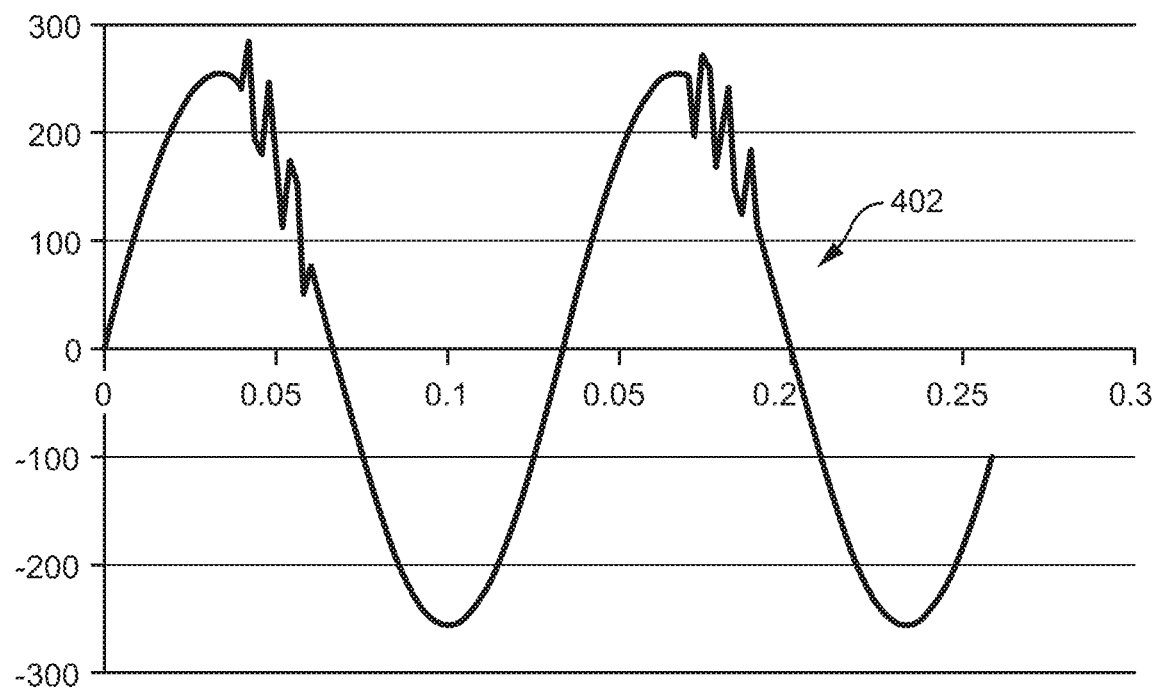
FIG. 4A illustrates a composite electrographic signal including a high-frequency component with signal content or oscillation in a high-frequency range, and a low-frequency component with signal content or oscillations in a low-frequency range.

The bandpass filter 316 receives an amplified and digitized electrographic signal from the sensing front end 312 and separates the signal into various frequency components that are of interest in measuring phase-amplitude coupling. For example, referring to FIG. 4A, an electrographic signal 402 may be a composite of approximately 7 Hz as a low frequency component and 50 Hz as a higher frequency component. The electrographic signal 402 shown in FIG. 4A is a simplified waveform used to illustrate the function of the data analyzer 314. An actual electrographic signal typically has more frequency and amplitude components.

Figure 4B:
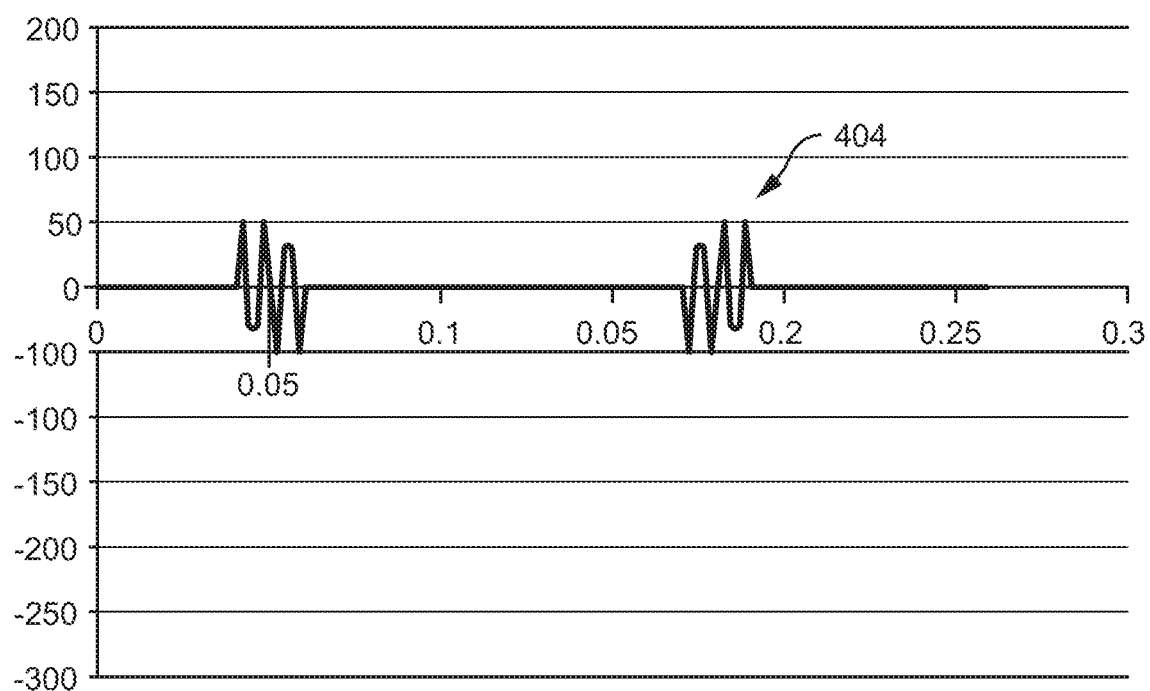
FIG. 4B illustrates the high-frequency component of the electrographic signal of FIG. 4A.
Figure 4C:
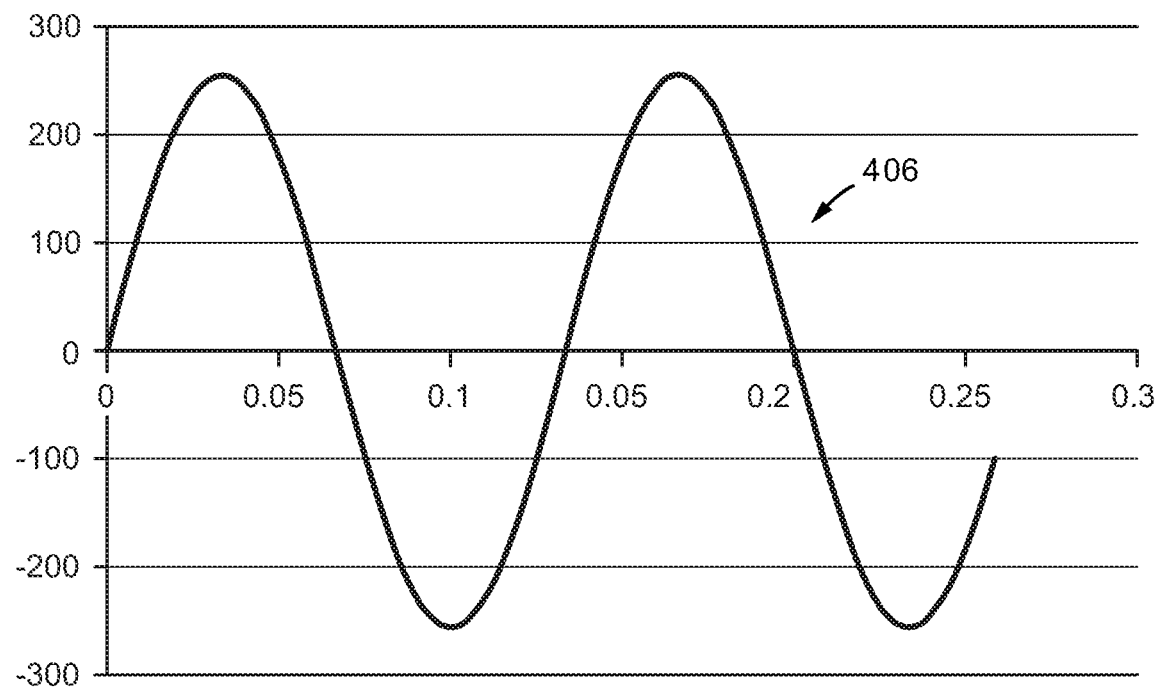
FIG. 4C illustrates the low-frequency component of the electrographic signal of FIG. 4A.

The electrographic signal 402 of FIG. 4A may be processed by two different band pass filters within the bandpass filter 316. For example, one bandpass filer may be designed to pass the high frequency component and the other bandpass filter may be designed to pass the low frequency component. FIG. 4B illustrates the high frequency component 404 of the electrographic signal of FIG. 4A. FIG. 4C illustrates the low frequency component 406 of the electrographic signal of FIG. 4A. The frequency components of the electrographic signal that are not passed by a bandpass filter are attenuated.

The bandpass filters in the bandpass filter 316 are programmable so that the center frequencies can be selected to pass particular frequencies of interest. For example, bandpass filters may be programmed to pass the following frequencies of interest:

Delta (1-4 Hz)
Theta (4-8 Hz)
Alpha (8-13 Hz)
Beta (13-25 Hz)
Low gamma (25-50 Hz)
High gamma (50-200 Hz)
Gamma (25 Hz high pass)
Pass-thru (no filtering)

In one configuration, the bandpass filters accept 10-bit digitized electrographic signals that are sampled at up to 1000 Hz. These digitized electrographic signals are accepted from the sensing channels 313a, 313b, 313c of the sensing front end 312. On the output side, each bandpass filter provides an electrographic data stream, filtered in accordance with the frequency specifications of the bandpass filter. For example, as shown in FIG. 3, the bandpass filter 316 may output a high-frequency filtered signal 324 (in the form of an electrographic data stream) provided by a high-frequency bandpass filter. This high-frequency filtered signal 324 corresponds to the high frequency component of the electrographic signal, such as shown in FIG. 4B. The bandpass filter 316 may also output a low-frequency filtered signal 326 (also in the form of an electrographic data stream) provided by a low-frequency bandpass filter. This low-frequency filtered signal 326 corresponds to the low frequency component of the electrographic signal, such as shown in FIG. 4C.

Each of the high-frequency filtered signal 324 and the low-frequency filtered signal 326 are input to the feature extraction module 318. More specifically, the high-frequency filtered signal 324 is input to the peak logger 320, which is configured to identify high-frequency content or features within the high-frequency filtered signal, and the low-frequency filtered signal 326 is input to the phase assignment module 322, which is configured to identify low-frequency content or features within the low-frequency filtered signal.

In the implementation disclosed in detail herein, the feature extraction module 318 is configured to include one or more half wave detectors or half wave detection tools for purposes of detecting features that represent oscillations in the electrographic signals. Half wave detectors, however, are not the only way to detect such features. Accordingly, the feature extraction module 318 may be configured with feature or content detectors other than half wave detectors. For example, filters comprised of both digital components (e.g., numerical calculations) and analog components (e.g., resistors and capacitors) may be used with varying degrees of success and power consumption to detect features that represent oscillation in the electrographic signals.

Regarding half wave detectors, details of such detectors are described in U.S. Pat. No. 6,810,285 titled "Seizure Sensing and Detection Using an Implantable Device," U.S. Patent Publication No. 2014/0276181 titled "Methods and Systems for Automatically Identifying Detection Parameters for an Implantable Medical Device", and U.S. Application Serial No. 2017/0049351 titled "Neurological Event Detection Tools for Implantable Medical Devices," the disclosures of which are incorporated herein by reference.

In general, the half wave detection tool measures characteristics of an electrographic signal related to the dominant frequency content of the signal. The half wave detection tool processes data samples corresponding to a portion of an electrographic signal against a set of detection criteria, and identifies the portion as a "qualified" half wave when the detection criteria are satisfied. Half wave detection criteria may be defined by a programmed set of detection parameters including: a minimum amplitude threshold, a maximum amplitude threshold, a hysteresis value, a minimum duration threshold and a maximum duration threshold.

In one implementation, a portion of an electrographic signal being processed by a half wave detector is identified as a "qualified" half wave when: 1) the difference between a local waveform minimum and a local waveform maximum of the portion, i.e., the half wave amplitude, is within the minimum and maximum amplitude thresholds, with hysteresis applied, and 2) a duration of the portion is within the minimum and maximum duration thresholds. If the portion of the electrographic signal being processed satisfies only one of the amplitude criteria (with hysteresis applied) and the duration criteria, but not both, the portion of the electrographic signal is identified as an "unqualified" half wave. For example, a half wave that satisfies the local waveform minimum and a local waveform maximum within the minimum and maximum amplitude thresholds, with hysteresis applied, but does not satisfy the minimum and maximum duration thresholds, may be identified as an "unqualified" half wave.

In the description to follow, the portion of an electrographic signal being process may be referred to generically as a "half wave," without any "qualified" or "unqualified" designation. Only after completion of processing by a half wave detector, is the portion or half wave identified as either "qualified" or "unqualified." Furthermore, in some methods of computing measures of phase-amplitude coupling described herein, unqualified half waves that do not meet the qualification criteria are ignored. In other methods, however, both qualified and unqualified half waves are considered when computing measures of phase-amplitude coupling.

Figure 4D:
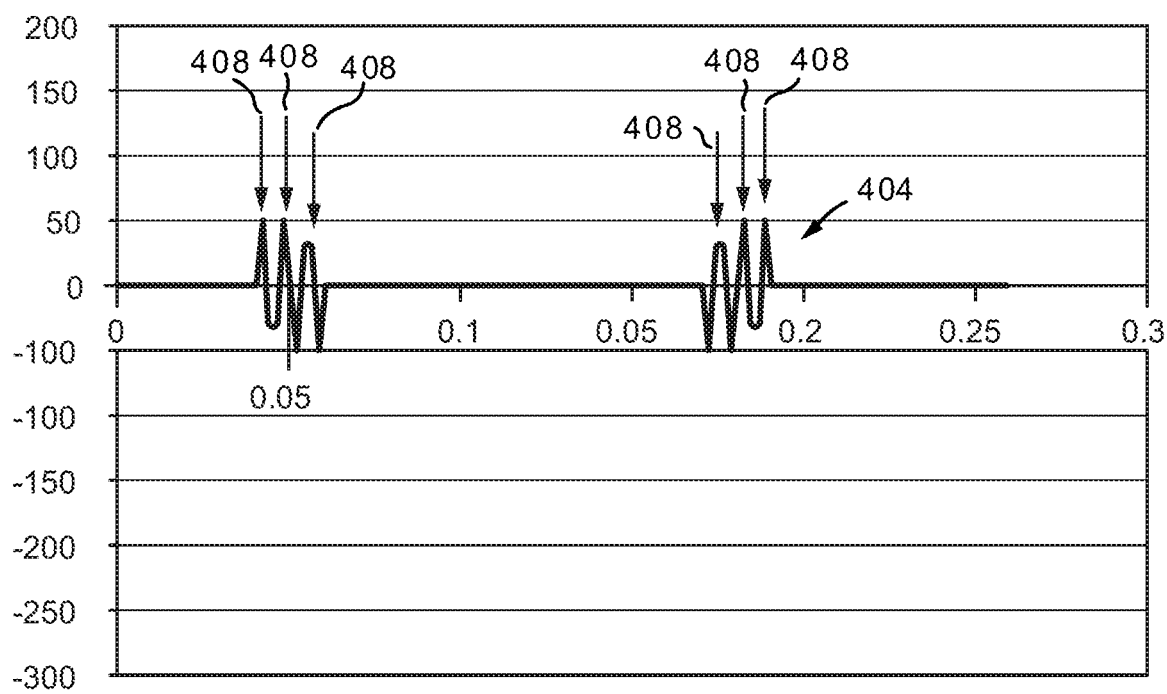
FIG. 4D illustrates occurrences of features (e.g., half wave peaks) representing signal content or oscillation in the high-frequency component of the electrographic signal of FIG. 4B.

With reference to FIGS. 3 and 4D, the peak logger 320 is configured to process the high-frequency filtered signal 324 to identify and mark the time of occurrence of high-frequency features of interest. For example, the peak logger 320 may be configured to identify the peaks 408 found in the high frequency component 404 of the electrographic signal 402. In one configuration, the peaks 408 are identified using a half wave method, and the peak logger 320 is configured to record the time of occurrences of peaks associated with detected qualified half waves. In FIG. 4D, these peaks 408, which may be referred to as "qualified peaks," are defined as the highest value electrographic data sample during a qualified half wave.

Figure 4E:
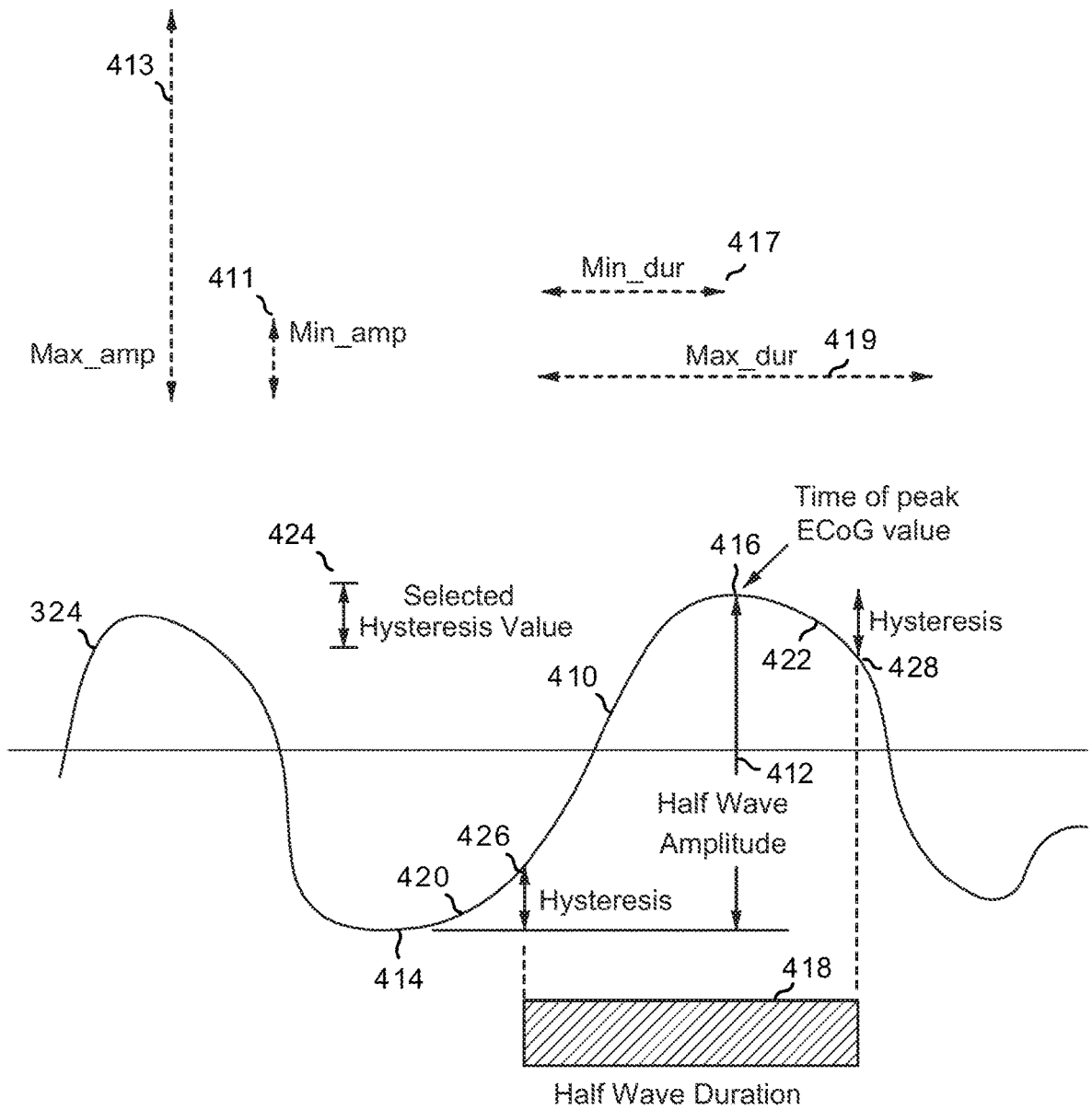
FIG. 4E illustrates a method of analyzing a region of interest of a high-frequency component of an electrographic signal to detect signal content or oscillations (e.g., half waves) in a high-frequency range.

With reference to FIG. 4E, the peak logger 320 may be configured, through a set of programmable detection parameters, to identify portions of the high-frequency filtered signal 324 as qualified half waves—more particularly, qualified rising half waves—when the following criteria are met:

a. The half wave 410 (e.g., the portion of the electrographic signal 324 between the local minimum 414 and the local maximum 416) has an upward slope.

b. The amplitude 412 of the half wave 410 is between a minimum amplitude threshold value 411 and a maximum amplitude threshold value 413, which values are independently selectable to favor detection of half waves representing signal content or oscillations within a high-frequency range. The amplitude 412 is defined as the amplitude difference between the local minimum 414 and the local maximum 416 that define the half wave 410.

c. The duration 418 of the half wave 410 is between a minimum duration threshold value 417 and a maximum duration threshold value 419, which values are independently selectable to favor detection of half waves representing signal content or oscillations within the high-frequency range. In one configuration, the half wave duration 418 may be defined as starting at the hysteresis crossing 426 after the local minimum 414 or negative inflection and ending at the hysteresis crossing 428 after the local maximum 416 or positive peak. Alternatively, the half wave duration may be defined as the time elapsed between the local minimum 414 and the local maximum 416 that define the half-wave.

d. Inflection regions 420, 422 of the electrographic signal 324 represent a change in amplitude equal to or greater than a selectable hysteresis value 424. Inflection regions generally correspond to the portion of the electrographic signal following a change in direction of the signal. In FIG. 4E, inflection region 420 is defined by the local minimum 414 and the hysteresis crossing 426, while inflection region 422 is defined by the local maximum 416 and the hysteresis crossing 428.

In an example configuration, a half wave detector may be tuned to detect high frequency waves having a frequency of around 40 Hz, based on the following detection parameters:
minimum amplitude threshold=0.1 mV,
maximum amplitude threshold=0.2 mV,
hysteresis=0.05 mV,
minimum duration threshold of 6 msec, and
maximum duration threshold of 8 msec.

The peak logger 320 is configured to output time stamp information 328 to the peak-to-phase accumulator 332 corresponding to the time of occurrence of each qualified half wave 410 in the high frequency signal. The time of occurrence of a qualified half wave may correspond to a start time or end time of the qualified half wave, or another fiducial point within the half wave. For example, the time of occurrence of a half wave may correspond to the time of the peak of the half wave corresponding to the local maximum 416, in which case the output of the peak logger 320 may be a time stamp that mark the time of occurrence of the peak 416.

This peak 416 may be identified as the highest valued data sample within the set of data samples defining the qualified half wave.

In one configuration, unqualified half waves that do not meet the qualification criteria are ignored and no peaks are identified. In another configuration, the peak logger 320 may identify both qualified and unqualified half waves and output time stamp information 328 to the peak-to-phase accumulator 332 corresponding to the time of occurrence of each type of half wave.

Returning to FIG. 3, the phase assignment module 322 is configured to process the low-frequency filtered signal 326 to identify qualified half waves and to assign phase ranges or phase bins to the half waves. In one configuration, the phase assignment module 322 identifies qualified half waves in the low frequency signal and determines the start time and stop time of phase bins associated with each qualified half wave. Both rising and falling half waves are processed and assigned phases.

Figure 4F:
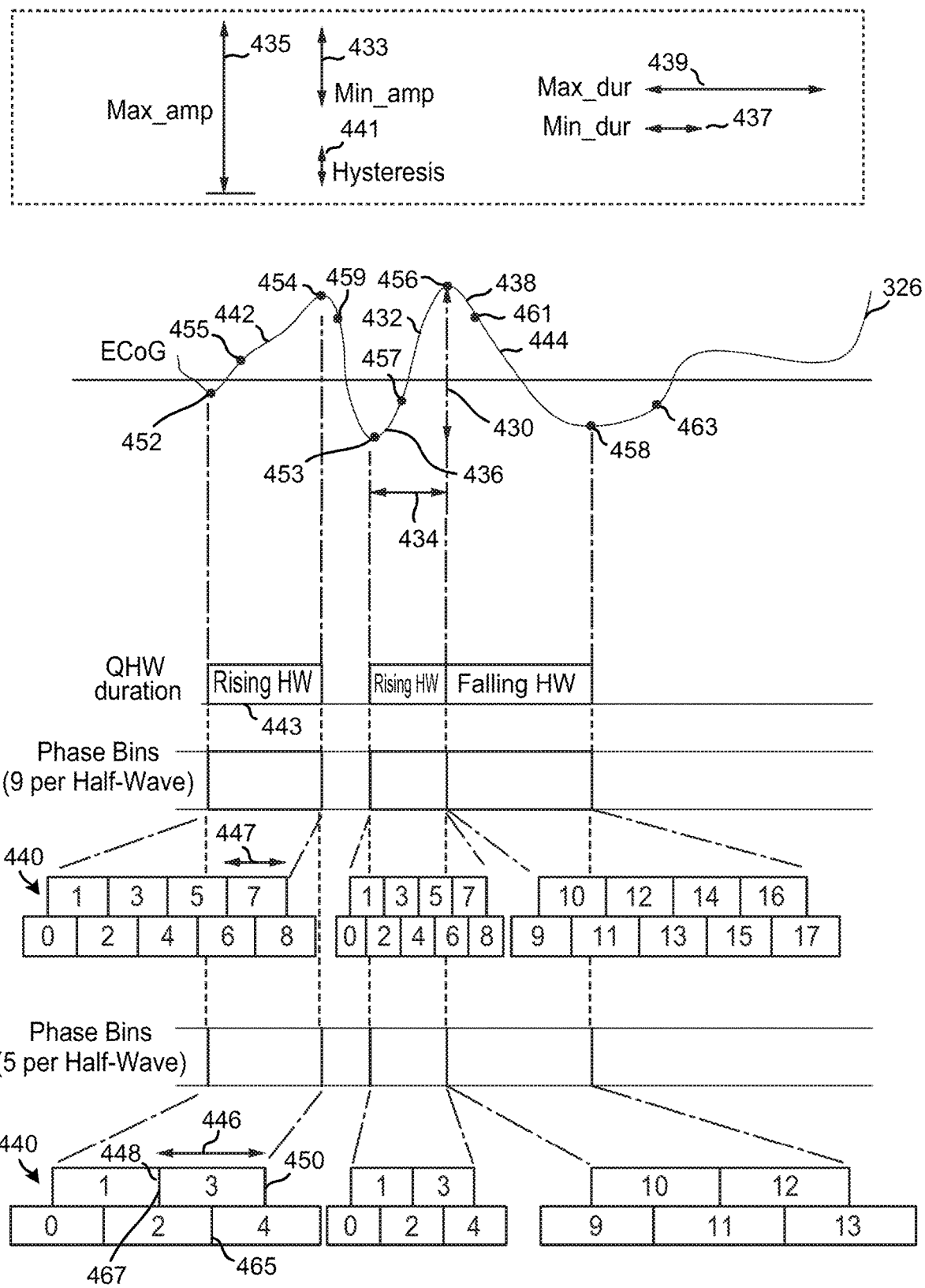
FIG. 4F illustrates a method of analyzing a region of interest of a low-frequency component of an electrographic signal to detect signal content or oscillations (e.g., half waves) in a low-frequency range, and to divide the detected signal content into designated phase ranges or phase bins.

With reference to FIGS. 3 and 4F, the phase assignment module 322 may be configured through a set of programmable detection parameters to identify portions of a low-frequency filtered signal 326 as qualified half waves when the following criteria are met:

a. The amplitude 430 of the half wave 432 is between a minimum amplitude threshold 433 and a maximum amplitude threshold 435, which values are independently selectable to favor detection of half waves representing signal content or oscillations within a low-frequency range. The amplitude 430 is defined as the amplitude difference between the local minimum 453 and the local maximum 456 that define the half wave 432.

b. The duration 434 of the half wave 432 is between a minimum duration threshold 437 and a maximum duration threshold 439, which values are independently selectable to favor detection of half waves representing signal content or oscillations within a low-frequency range.

c. Inflection regions 436, 438 of the electrographic signal 326 represent a change in amplitude equal to or greater than a selected hysteresis value 441. In FIG. 4F, inflection region 436 is defined by the local minimum 453 and the hysteresis crossing 457, while inflection region 438 is defined by the local maximum 456 and the hysteresis crossing 461

In an example configuration, a half wave detector may be tuned to detect low frequency waves having a frequency of around 7 Hz, based on the following detection parameters:
minimum amplitude threshold=1 my
maximum amplitude threshold=2 my
hysteresis=0.5 my
minimum duration threshold=60 msec
maximum duration threshold=80 msec In one configuration, unqualified half waves that do not meet the qualification criteria are ignored and no phase bins are assigned to them. In another configuration, the phase assignment module 322 may identify both qualified and unqualified half waves and assign phases to both types of half waves.

Continuing with FIG. 4F, the number of phase ranges or phase bins 440 per half wave is selectable and the phase bin numbers are assigned such that qualified rising half waves 432, 442 are given bin numbers contained by the range 0-8 and the qualified falling half waves 444 are given bin numbers contained by the range 9-17. For example, if 5 bins per half wave are selected then bin numbers 0-4 are assigned to rising half waves and bin numbers 9-13 are assigned to falling half waves. All other bin numbers (5, 6, 7, 8, 14, 15, 16, and 17) are unassigned in this example.

As shown toward the bottom of FIG. 4F, each phase bin 440 has a duration 446 that is proportional to the duration 443 of the associated half wave. Each phase bin 440 has a first time stamp that marks its start 448 and a second time stamp that marks its end 450. The arrangement of the phase bins 440 depends on the selected number of bins per half wave. In FIG. 4F, examples are given for 5 phase ranges or phase bins 440 per half wave and for 9 phase ranges or phase bins 440 per half wave.

Each qualified half wave 432, 442, 444 is either a qualified rising half wave 432, 442, or a qualified falling half wave 444. Each qualified rising half wave 432, 442 is defined as starting at a local minimum and ending at a local maximum. For example, qualified rising half wave 442 starts at a local minimum 452 and ends at a local maximum 454. Each qualified falling half wave 444 is defined as starting at a local maximum 456 and ending at a local minimum 458. The qualified half wave (QHW) line of FIG. 4F illustrates the durations of the qualified half waves 432, 442, 444.

Returning to the bottom of FIG. 4F, the start 448 and stop of 450 of each phase bin 440 is calculated based on the time of the start and end of each qualified half wave. For example, in the 5 phase-bin scenario, the duration 446 of each phase bin 440 is set to half the duration 443 of the associated qualified half wave 442. In the 9 phase-bin scenario, the duration 447 of each phase bin 440 is set to one-fourth the duration 443 of the associated qualified half wave 442. The start and end of each qualified rising half wave 432, 442 is defined as the time of the local minimum 452, 453 seen prior to an up hysteresis crossing 455, 457 and the time of the local maximum 454, 456 seen prior to a down hysteresis crossing 459, 461. The start and end of each qualified falling half wave 444 is defined as the time of the local maximum 456 seen prior to a down hysteresis crossing 461 and the time of the local minimum 458 seen prior to an up hysteresis crossing 463. Thus, for low frequency content processing, the delay between the peak and the hysteresis crossing is removed from the defined start and end of each half wave. This is different from the high frequency content described with reference to FIG. 4E, where in one configuration the start and end of each half wave (the half wave duration 418) depends on hysteresis crossings 426, 428.

The data analyzer 314 calculates the duration 446, 447 as follows. The half wave duration 443 is divided by 1, 2, or 4 respectively when 3, 5, or 9 phase bins per phase are selected respectively. Each phase bin 440 is assigned a duration 446, 447 that is equal to the quotient, with the remainder discarded. Thus, for a 5-phase-bin implementation, the duration 446 of each phase bin is one-half of the half wave duration 443. For the 9-phase-bin implementation, the duration 447 is one-fourth the half wave duration 443. In terms of data samples, if the half wave duration 443 is 54 samples and 9 bins per phase is selected, the duration 447 is the half wave duration (54) divided by 4. The quotient is 13 with a reminder of 2. Accordingly, each of the 9 phase bins may be characterized as being 13 electrographic signal samples wide.

Each duration 446, 447 of each respective phase bin 440 is defined by a start time corresponding to the time stamp of the first data sample in the bin, and an end time corresponding to the time stamp of the last data sample in the bin. In FIG. 4F, the phase bins 440 are illustrated in a stacked, overlapping manner. In terms of respective durations, this illustrates that the start times and end times of certain phase bins may be included in the durations of other bins; in other words, the start times and end times of certain phase bins may fall between the start time and end time of other bins.

For example, in the 5-phase-bin scenario, the end time 467 of bin 1 is included in the duration of bin 2. Likewise, the end time 465 of bin 2 is included in the duration of bin 3. The overlapping of bins also illustrates that the phase bins 440 cover the half wave duration 443 with approximately one-half bin width overhanging the start and end of the half wave. Thus, in the 5-phase-bin scenario, a portion of the duration of bin 0 and bin 4 are outside of the half wave duration 443, while in the 9-phase-bin scenario, a portion of the durations of bin 0 and bin 8 are outside of the half wave duration.

Returning to FIG. 3, the phase assignment module 322 is configured to output time information 330 to the peak-to-phase accumulator 332 corresponding to a series of time stamps that mark the start 448 and end 450 of each phase bin 440. The time information 330 may be provided as a series or index of time stamps.

The peak-to-phase accumulator 332 receives the time stamp information 328 from the peak logger 320 and the time stamp information from the phase assignment module 322 as inputs and processes these time stamps to determines—for each phase bin—how many high frequency peaks (wherein, each peak corresponds to a time stamp from the peak logger 320) happen coincident with the phase bin (wherein, each phase bin is defined by a pair of consecutive time stamps from the phase assignment module 322, which time stamps represent the beginning and end of the phase bin). As used herein, "coincident" is defined as happening after the start 448 of a phase bin 440 but before the end 450 of the phase bin. Accordingly, a time stamp from the peak logger 320 having a value between the value of the start time stamp and the value of the end time stamp of a phase bin is considered coincident with that bin.

The peak-to-phase accumulator 332 determines how many time stamps included in the time stamp information 328 from the peak logger 320 occur during the times marked as the start and end of each phase bin by the time information 330 from the phase assignment module 322. The data output 334 of the peak-to-phase accumulator 332 is a count high-frequency (HF) peaks (each of which corresponds to a qualified half wave in the high frequency signal) for each phase bin that takes the form shown below. Each time a high frequency peak occurs during a phase bin, the count for the bin number corresponding to the phase bin is incremented. The HF peaks correspond to first features or high-frequency features of the electrographic signal, while the rising half waves and falling half waves correspond to second features or low-frequency features of the signal.

| Bin Number | Count of HF Peaks |
|---|---|
| 0 | 1 |
| 1 | 2 |
| 2 | 4 |
| 3 | 2 |
| 4 | 1 |
| 5 | 5 |
| 6 | 3 |
| 7 | 2 |
| 8 | 1 |
| 9 | 25 |
| 10 | 50 |
| 11 | 45 |
| 12 | 10 |
| 13 | 5 |
| 14 | 2 |
| 15 | 4 |

-continued

| Bin Number | Count of HF Peaks |
|---|---|
| 16 | 3 |
| 17 | 2 |

The count per bin is referred to as a phase amplitude histogram. As described further below, the data analyzer 314 is configured to obtain phase amplitude histogram data 334 on a region of interest, or window, of an electrographic signal, and evaluate the data for phase-amplitude coupling. In this regard, the data analyzer 314 includes a window generator module 348 configured to generate a pulse at a regular interval. The time between consecutive pulses defines the duration of a window. The interval (or window duration) is selectable to be favorable to detect changes in the phase-amplitude coupling that are of interest. The range of selectable values for the window duration may range from 256 msec to 4096 msec, in 256 msec steps.

Regarding window duration, a longer window duration provides a larger amount of histogram data 334 from which more sensitive measures of PAC may be obtained. A shorter window duration provides more frequent measure of PAC and thus allows the data analyzer 314 to detect changes in the level of PAC more quickly. However, the shorter window duration provides a smaller amount of histogram data, which may cause the data analyzer to be less sensitive to small shifts in the level of PAC. Generally, a window duration is long compared to the frequency of the low frequency electrographic signal waveform. For example, if the window duration is set to 2 seconds and the low frequency waveform is on order of 10 Hz, and assuming there is one qualified rising halve wave and one qualified falling half wave per cycle, there could be approximately twenty qualified rising half waves and twenty qualified falling half waves. In this case, with respect to FIG. 4F, for the 5-phase bin example there would be 20 instances of each of phase bins 0-4 and 9-13.

During a window, histogram data 334 is produced by the above described operations of the peak logger 320, the phase assignment module 322, and the peak-to-phase accumulator 332. At the end of each window, the histogram data 334 for the window is provided to the PAC module 336, where, as described further below, the data is processed to compute measures of phase-amplitude coupling or PAC scores. The histogram data 334 is then cleared or zeroed out of the peak-to-phase accumulator 332, and new histogram data is produced for a next window.

Continuing with FIG. 3, the PAC module 336 includes one or more submodules configured to process the histogram data 334. The submodules may include, for example, a window qualification module 338, a PAC measurement module 340, and an X of Y module 346. In general, the PAC module 336 accepts the histogram data 334 that is presented to it at the end of each window as its input, processes the data for the just-expired window, and generates a PAC output 342 based on the processing outcome. The PAC module 336 may also provide diagnostic information 343 to a histogram logger 344. Diagnostic information 343 may include, for example, histogram data information, such as the bin number for the phase bin with the highest (lowest) number of high frequency peaks along with the number of peaks logged in that bin.

In one configuration, the histogram data 334 from a just-expired window is initially processed to determine if the histogram data meets criteria for additional processing. If the criteria are not met, the histogram data 334 for the just-expired window is deemed disqualified and is not processed, and a PAC output 342 indicative of this disqualification is generated by the PAC module 336. In an example implementation, the window qualification module 338 processes the histogram data 334 against criteria to determine if the just-expired window is a qualified window. Criteria may relate to the quantities of features representing signal content or oscillations in the low-frequency range, and features representing signal content or oscillations in the higher-frequency range. For example, one criterion may require that the just-expired window have at least a specified number of qualified low frequency rising and/or falling half waves. Another criterion may require that the total number of high frequency peaks within the just-expired window be either greater than a minimum number or less than a maximum number.

If the histogram data 334 from a just-expired window is determined to be qualified, the data is processed by the PAC measurement module 340 to derive a measure of PAC or a PAC score, and a PAC output 342 indicative of the PAC score is generated by the PAC module 336.

Regarding PAC scores, different algorithms may be implemented by the PAC measurement module 340 to such scores. Examples implementations follow:

Min/Max

Figure 4G:
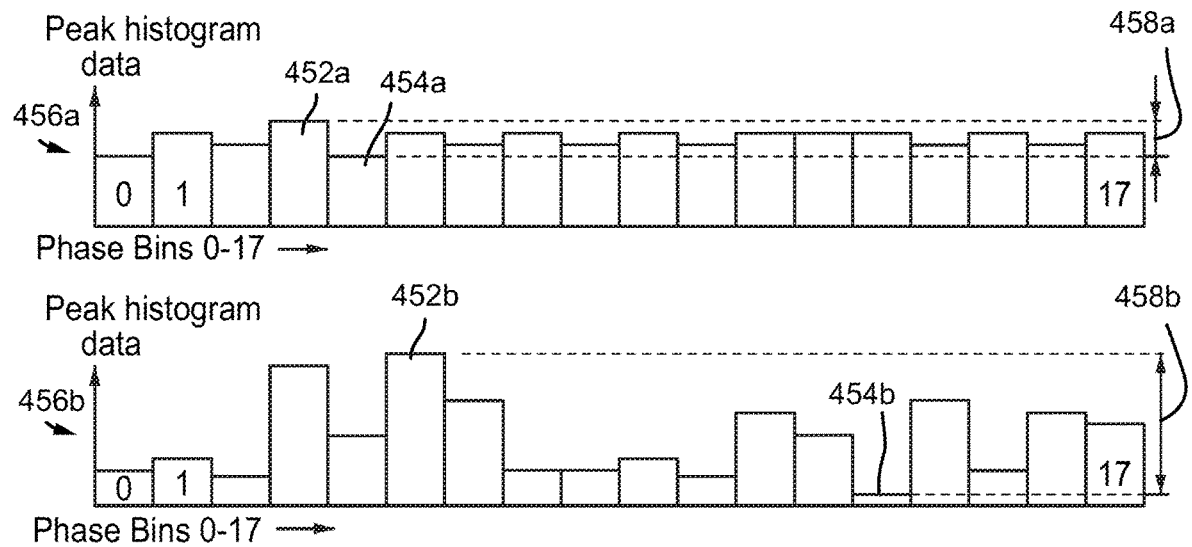
FIGS. 4G and 4H illustrate histograms representing counts of detected high-frequency content (e.g., half waves) per low-frequency phase range or phase bin assignments.

In this example implementation, the PAC measurement module 340 identifies the histogram bin having the highest count and the histogram bin having the lowest county, and subtracts the lowest count from the highest count to obtain a measure of PAC (or a PAC score). Referring to FIG. 4G, for the upper histogram 456a, the PAC measurement module 340 identifies histogram bin 452a as the highest-count bin and histogram bin 454a as having the lowest-count bin. The PAC measurement module 340 subtracts the lowest count from the highest count to obtain a PAC score 458a. For the lower histogram 456b of FIG. 4G, the PAC measurement module 340 identifies the histogram bin 452b as the highest-count bin and the histogram bin 454b as the lowest-count bin, and subtracts the counts to obtain a PAC score 458b. In the example histograms of FIG. 4G, the upper histogram 45a has a lower PAC score 458a.

Aggregated Bin Values

In this example implementation, the PAC measurement module 340 identifies multiple histogram bins having high counts and multiple histogram bins having low counts, accumulates the respective high counts and respective low counts, and processes the cumulative high count and the cumulative low count to arrive at a PAC score. For example, the PAC measurement module 340 may process the counts by determining the ratio of the cumulative high count to the cumulative low count. This ratio is the PAC score.

Figure 4H:
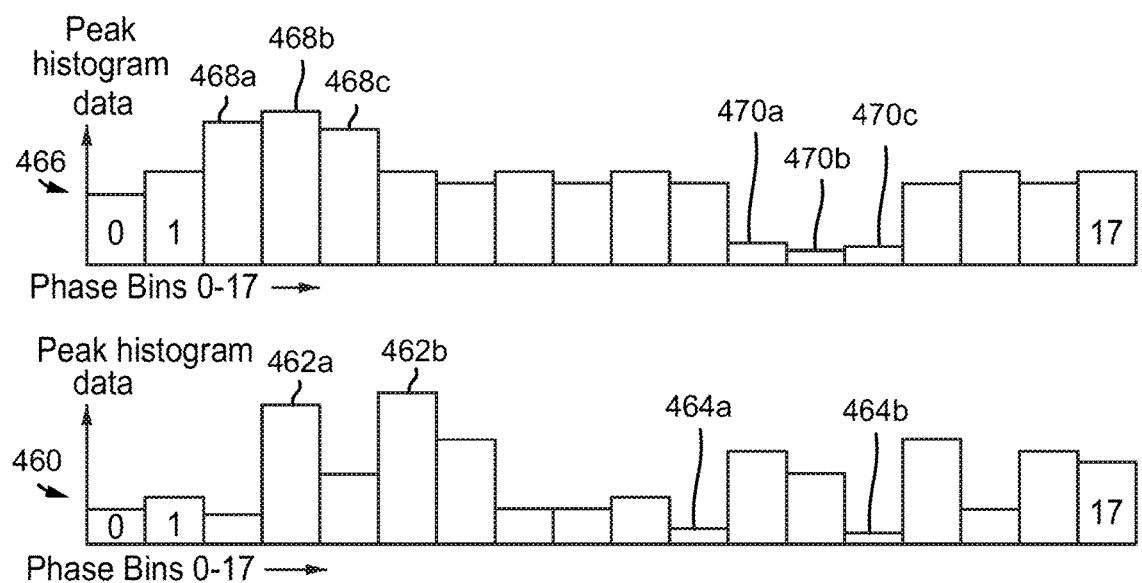

Referring to FIG. 4H, with respect to the upper histogram 460, in one embodiment, the PAC measurement module 340 may be configured to a) identify a number N of histogram bins 462a, 462b with the highest number of counts, and calculate the total number of counts in the identified bins, b) identify a number M of histogram bins 464a, 464b with the lowest number of counts, and calculate the total number of counts in the identified bins, and c) determine a PAC score as the ratio of the cumulative high count to the cumulative low count. M and N may be a number selected based on the total number of bins in the histogram.

With respect to the lower histogram 466 of FIG. 4H, in another embodiment, the PAC measurement module 340 may be configured to: a) identify a number N of contiguous histogram bins 468a, 468b, 468c with the highest number of counts, and calculate the total number of counts in the identified bins, b) identify the number M of contiguous histogram bins 470a, 470b, 470c with the lowest number of counts, and calculates the total number of counts in the identified bins, and c) determine a PAC score as the ratio of the cumulative high count to the cumulative low count. Again, M and N may be a number selected based on the total number of bins in the histogram.

Concentration Peaks

In this example implementation, the PAC measurement module 340 determines the minimum number of bins required to account for a selected percentage of accumulated peaks. The percentage may be a programmable value. The determined number of bins is the PAC score. For example, referring to the table below, if the total number of HF peaks accumulated for a just expired window is 160, and the selected percentage is 50%, then the PAC measurement module 340 may determine the PAC score as follows: First the PAC measurement module 340 scans through the list of bin numbers and associated counts to determine an order of bins from the highest peak count to the lowest peak count.

| Bin Number | Count of HF Peaks |
| --- | --- |
| 0 | 1 |
| 1 | 2 |
| 2 | 4 |
| 3 | 2 |
| 4 | 36 |
| 5 | 5 |
| 6 | 3 |
| 7 | 2 |
| 8 | 1 |
| 9 | 25 |
| 10 | 43 |
| 11 | 10 |
| 12 | 10 |
| 13 | 5 |
| 14 | 2 |
| 15 | 4 |
| 16 | 3 |
| 17 | 2 |

In this example, the order of bins is {10, 4, 9, 11, 12, 13, 2, 15, 6, 16, 1, 3, 7, 14, 2, 0, 8}. Next, the PAC measurement module 340 adds the counts associated with the bins, in the order determined by the order of bins, until a target count is reached or first exceeded, where the target count corresponds to the selected percentage of total counts. In this example, the target count is 50% of 160=80. The target count is first exceeded after adding the counts of bins 10, 4 and 9. More specifically: 43 (from bin 10)+36 (from bin 4)+25 (from bin 9)=104. Accordingly, the minimum number of bins it takes to reach or exceed the target count is 3. Thus, in this example, the PAC measurement module 340 determines the PAC score is 3.

Alternatively, the PAC measurement module 340 may determine the minimum number of contiguous bins required to account for a selectable percentage of accumulated peaks. The determined number of bins is the PAC score. Referring to the above table of bin counts, and working with the same target count of 50, the PAC measurement module 340 may determine the PAC score by scanning through the counts in order from 1-17 to identify sets of bins associated with bins having high counts. (In this implementation, the bins are not reordered from highest to lowest.) In the above example, bin 4 and bin 10 may be identified as having high counts and the bins on either side of these respective bins may be considered a set of associated bins. Next, the PAC measurement module 340 processes the bin counts to identify the set of associated bins having the least number of bins, that result in an accumulated count that reaches or exceeds the target count. In this example, the set of contiguous bins formed by bins {9, 10, 11, 12} represents the least number of bins having an accumulated count that exceeds the target count of 80. More specifically: 25 (from bin 9)+43 (from bin 10)+10 (from bin 11)+10 (from bin 12)=88. The other set of contiguous bins associated with bin 4 requires a greater number of bins to reach or exceed the target count. Accordingly, the minimum number of contiguous bins it takes to reach or exceed the target count is 4. Thus, in this example, the PAC measurement module 340 determines the PAC score is 4.

Pre-Selected Bins

In this implementation, the PAC measurement module 340 determines a measure based on the number of counts that occur during a selected set of bins. The set of bins may be selected through device programming. The measure is the PAC score. For example, the measure may be the percentage of peaks during a window that occur within the selected set of bins. The percentage is the PAC score. Referring to the table below, if the total number of HF peaks accumulated for a just expired window is 160, and the selected set of bins is {9, 10, 11, 12}, then the PAC measurement module 340 may determine the PAC score as follows: First, the PAC measurement module 340 accumulates the counts associated with the selected bins.

| Bin Number | Count of HF Peaks |
| --- | --- |
| 0 | 1 |
| 1 | 2 |
| 2 | 4 |
| 3 | 2 |
| 4 | 36 |
| 5 | 5 |
| 6 | 3 |
| 7 | 2 |
| 8 | 1 |
| 9 | 25 |
| 10 | 43 |
| 11 | 10 |
| 12 | 10 |
| 13 | 5 |
| 14 | 2 |
| 15 | 4 |
| 16 | 3 |
| 17 | 2 |

In this case, the count is: 25 (from bin 9)+43 (from bin 10)+10 (from bin 11)+10 (from bin 12)=88. Next, the PAC measurement module 340 calculates the percentage the accumulated count is of the total number of counts. In this example, the percentage is 88/160*100=55%. Thus, the PAC measurement module 340 determines the PAC score is 55%. The PAC score may be any other measure derivable from the counts. For example, the PAC score may be the ratio 88/160=0.55.

Other algorithms or processes may be implemented to obtain a measure of phase-amplitude coupling or a PAC score for a just-expired window. For example, as previously mentioned, additional processes may involve considering both qualified half waves and unqualified half waves when computing a measure of phase-amplitude coupling. These additional processes are described further below with reference to FIGS. 7A-11.

After obtaining a PAC score for a just-expired window, the PAC measurement module 340 may be further configured to evaluate the PAC score, together with other information derived from the histogram data to determine if the just-expired window should be identified or flagged as having satisfied a PAC criterion. For example, the PAC measurement module 340 may determine the number of qualified half waves from the lower frequency signal based on histogram data corresponding to the output of the phase assignment module 322, and the number of peaks from the higher frequency signal based on histogram data corresponding to the output of the peak logger 320. If all three measurements (PAC score, number of half waves, number of peaks) meet pre-selected threshold criteria then the PAC output 342 is set to indicate the just-expired window satisfies a PAC criterion.

The PAC measurement module 340 may be further configured to determine if PAC criteria is met for a group of windows. For example, the PAC measurement module 340 may include an X of Y module 346 that monitors the individual PAC scores for a series of windows to determine when at least X of the most recent Y windows met their individual PAC criterion.

Returning to FIGS. 2 and 3, the histogram logger 344 accepts data from the PAC module 336 and stores it in a memory, which may be configured as a FIFO buffer. These data are then available for the CPU 240 to collect and analyze or store for later upload through an electrographic signal data retrieval process. The content of the data can vary depending on the thresholding process selected in the PAC module 336. In one example, the histogram logger 344 may: a) read two bytes of data from the PAC module 336 one time per window, 2) store the data in a memory structure for at least 64 windows, and 3) provide a means for the CPU 240 to read the data from the memory structure.

Following are additional examples of methods of computing measures of phase-amplitude coupling using an implantable medical device.

Measuring Phase-Amplitude Coupling

With reference to FIGS. 5 through 11, a method of computing measures of phase-amplitude coupling using an implantable medical device is described. For example, the method may be implemented using the neurostimulation system described above with respect to FIGS. 2-4H. While details of the method are described within the context of measuring theta-gamma coupling, the method is equally applicable to different cross frequency couplings.

Obtaining a Brain Signal

Figure 5:
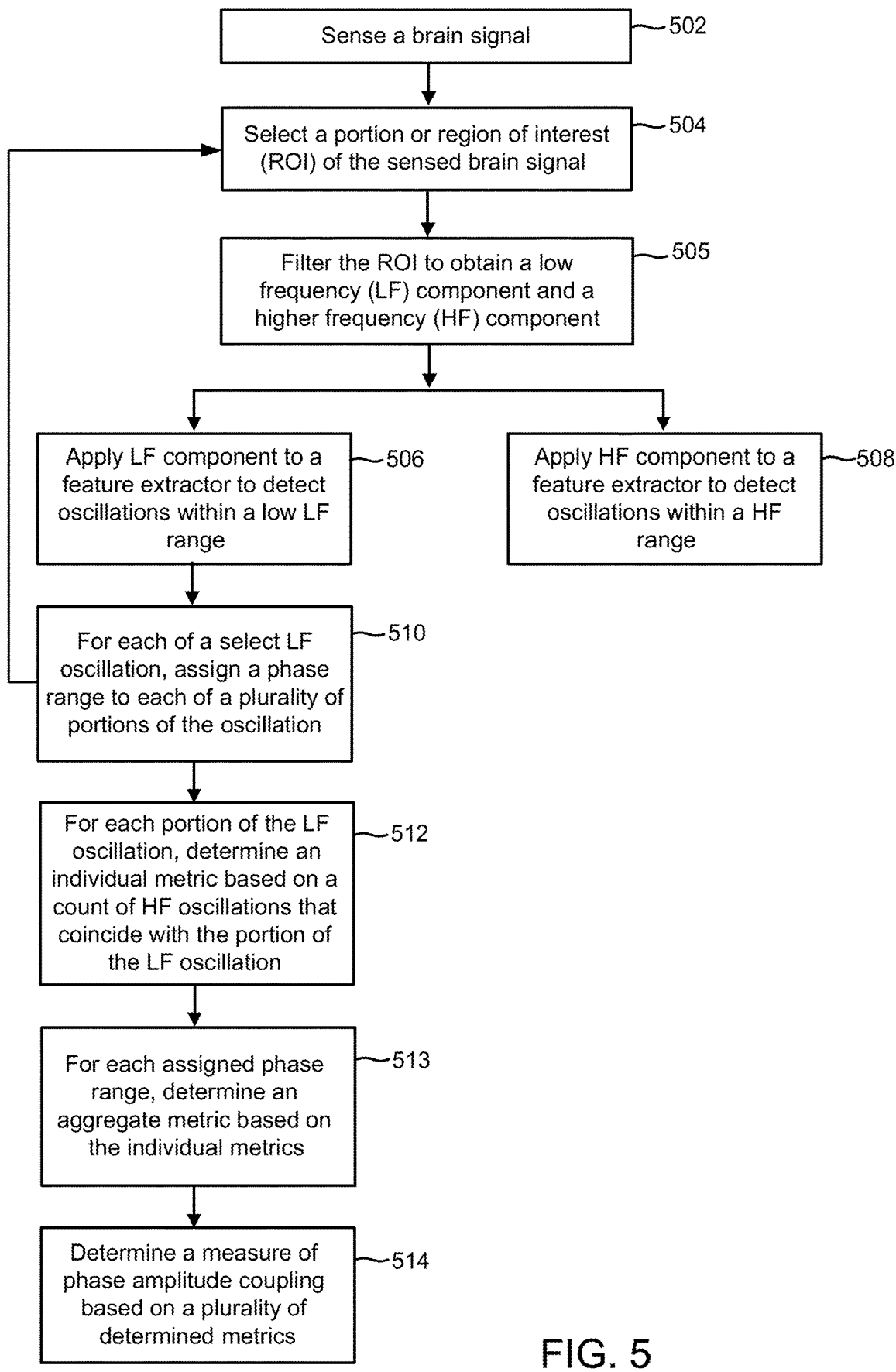
FIG. 5 is a flowchart of a method of measuring phase-amplitude coupling using an active implantable medical device.

With reference to FIG. 5, at block 502 a brain signal is sensed by the implantable medical device. The brain signal may be sensed continuously using one or more of the intracranial implanted electrodes shown in FIG. 1. For example, voltage potentials sensed across implanted electrodes may be sampled as a function of time to obtain data samples that may represent a composite electrographic signal including features across various frequency ranges. An example of a composite electrographic signal 602 is shown in FIG. 6A.

At block 504, a portion of the sensed brain signal 602 is selected by the implantable medical device for further processing. The selected portion is referred to herein as a "region of interest" (ROI) of the electrographic signal. In cases where the brain signal 602 is continuously sensed, the implantable medical device may define a processing window 612 of time through which the continuously sensed brain signal passes. In FIG. 6A, the brain signal 602 may be viewed as passing through the processing window in the direction of the arrow 614. The implantable medical device may at any given time select the portion of the brain signal 602 that is within the processing window 612 for further processing. The duration of the processing window 612 may be adjusted depending on the cross-frequency coupling being calculated and on a neurological state of the patient. For example, for theta-gamma coupling, the processing window may be a 5-10 second window and for alpha-beta coupling, the processing window may be a 1-2 second window.

Processing the Brain Signal

At block 505, the selected region of interest of the electrographic signal is filtered, for example, by applying the region of interest to the bandpass filter 316 shown in FIG. 3. Filtering the region of interest provides a low-frequency component 604 of the region of interest and a higher-frequency component 606 of the region of interest.

At block 506, the low-frequency component 604 is applied to a first feature extractor of the implantable medical device. The first feature extractor may be embodied as a half wave detector and may correspond to the phase assignment module 322 of FIG. 3. The first feature extractor is configured to process the low-frequency component 604 to detect features representing oscillations within a low frequency range. These detected features may be referred to herein as "first features" or "low-frequency features."

As an example, the first feature extractor may be embodied as a half wave detector programmed with a set of detection parameters (such as described above with reference to FIG. 4F) that result in detection of theta half waves in the frequency range of 4-8 Hz. Oscillations in the theta range are shown in the theta waveform 604 in FIG. 6B. A small portion of a region of interest of a theta-gamma coupled brain signal 702 marked with theta half wave detections is shown in FIG. 7A. The two adjacent vertical lines 704 represent the maximum and minimum amplitude thresholds for detecting theta half waves, the adjacent horizontal lines 708 represent the maximum and minimum duration thresholds for detecting theta half waves, and the single vertical line 706 represents a hysteresis value for detecting local maxima and minima.

At block 508 the high-frequency component 606 is applied to a second feature extractor of the implantable medical device. The second feature extractor may be embodied as a half wave detector and may correspond to the peak logger 320 of FIG. 3. The second feature extractor is configured to process the high-frequency component 606 to detect features representing oscillations in a higher frequency range. These detected features may be referred to herein as "second features" or "higher-frequency features".

As an example, the second feature extractor may be embodied as a half wave detector programmed with a set of detection parameters (such as described above with reference to FIG. 4E) that result in detection of gamma half waves in the frequency range above 40 Hz. Oscillations in the gamma range are shown in the gamma waveform 606 in FIG. 6C. A region of interest of a theta-gamma coupled brain signal 710 marked with gamma half wave detections is shown in FIG. 7B. The two adjacent vertical lines 712 represent the maximum and minimum amplitude thresholds for detecting gamma half waves, the adjacent horizontal lines 714 represent the maximum and minimum duration thresholds for detecting gamma half waves, and the single vertical line 716 represents a hysteresis value for detecting local maxima and minima Assigning Phase Ranges to Select Oscillations in the Low Frequency Range Returning to FIG. 5, at block 510, the implantable medical device partitions select oscillations in the low frequency range into a number of assigned phase ranges. Selection of oscillations in the low frequency range for partitioning and phase range assignment may be based on qualification of half waves. As described above, within the context of half wave detectors, an oscillation in the low frequency range, e.g., a low-frequency half wave, may be either of a qualified half wave or an unqualified half wave.

With reference to FIG. 7A, qualified and unqualified half waves detected by a theta half wave detector, are identified by graphic symbols including filled, downward arrows and unfilled inverted triangles, and are numbered from 1 to 9. Within the set of theta half waves 1 to 9, theta half waves 1, 5, 6 and 7 are qualified theta half waves because each meets the set amplitude and duration criteria, i.e., their amplitudes are within the set minimum and maximum amplitude thresholds and their durations are within the set minimum and maximum duration thresholds. Theta half waves 2, 3, 4 are unqualified theta half wave because each has a duration that exceeds the set maximum duration threshold. Theta half waves 8 and 9 are unqualified theta half waves because each has an amplitude less than the set minimum amplitude threshold.

With reference to FIG. 7B, qualified and unqualified half waves detected by a gamma half wave detector are identified by graphic symbols including filled, downward arrows and unfilled inverted triangles. By applying rules for hysteresis, and amplitude and duration thresholds similar to those described above for the theta half-wave detector, the second half wave detector for gamma half waves identifies qualified and unqualified gamma half waves in accordance with the legend shown in FIG. 7B.

Returning to FIG. 5, in one implementation of the method of computing measure of phase-amplitude coupling using an implantable medical device, only qualified oscillations in the low frequency range, e.g., qualified low-frequency half waves, are processed. Accordingly, at block 510, if no qualified oscillations in the low frequency range are identified, the process returns to block 504, where a next portion of the continuously monitored brain signal is selected for processing. If qualified oscillations in the low frequency range are detected at block 510, the process proceeds with phase assignment. In an alternate implementation, both qualified and certain unqualified oscillations in the low frequency range may be processed. The following description of phase range assignment is made with respect to the implementation that processes only qualified half waves. The phase range assignment procedure, however, is equally applicable to an implementation that used both qualified and unqualified half waves. An implementation that uses both qualified and unqualified half waves is described later below.

Assigning Phase Ranges

Continuing with block 510, in the case where qualified oscillations in the low frequency range are selected for processing, each of the qualified oscillations in the low frequency range identified in block 510 are further processed on an individual basis, with some commonality depending on whether a qualified half wave is a rising half wave or a falling half wave. A rising half wave has an upward slope; while a falling half wave has a downward slope. In general, each qualified oscillation in the low frequency range is divided into a number of portions or phases that span an equal number of phase ranges. Each portion or phase of the qualified oscillation in the low frequency range is assigned a phase range or phase bin. Common phase ranges are assigned to qualified oscillations in the low frequency range having the same slope. In other words, each downward sloping portion of an oscillation in the low frequency range has the same phase ranges, and each upward sloping portion of an oscillation in the low frequency range has the same phase ranges.

Figure 8:
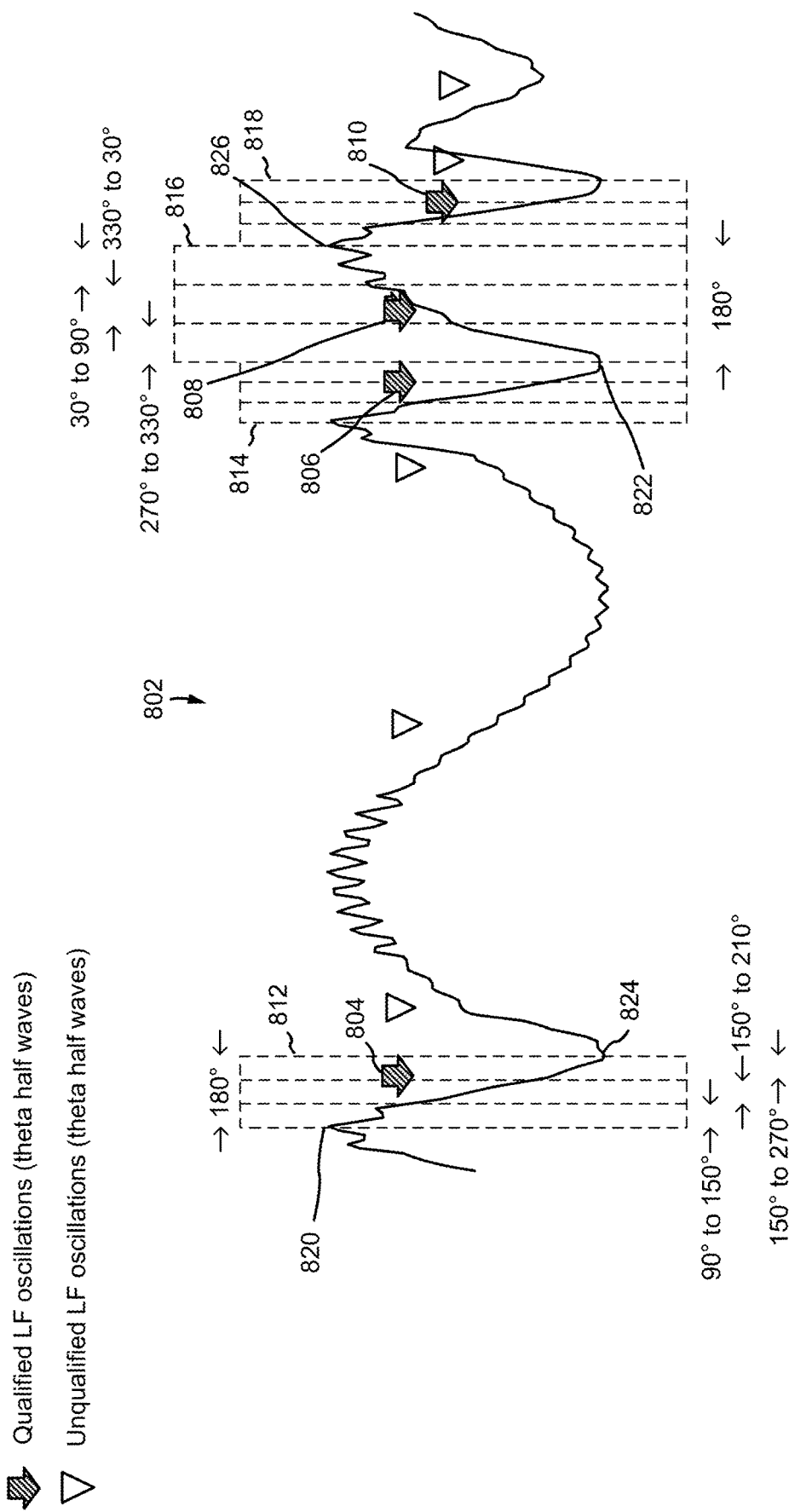
FIG. 8 illustrates a method of analyzing a region of interest of an electrographic signal characterized by cross-frequency coupling in which the phase ranges of low-frequency signal content or oscillations are identified.

An example of a partitioning of qualified oscillations in the low frequency range—in this case, qualified theta half waves—is illustrated in FIG. 8, wherein a region of interest of a theta-gamma coupled brain signal 802 is marked with four qualified theta half wave detections 804, 806, 808, 810. The first qualified theta half wave 804 corresponds to the portion of the brain signal 802 bounded by dashed box 812. The second qualified theta half wave 806 corresponds to the portion of the brain signal 802 bounded by dashed box 814. The third qualified theta half wave 808 corresponds to the portion of the brain signal 802 bounded by dashed box 816. The fourth qualified theta half wave 810 corresponds to the portion of the brain signal 802 bounded by dashed box 818. Each of the dashed boxes 812, 814, 816, 818 is partitioned in three by two vertical lines. The first qualified theta half wave 804, the second qualified theta half wave 806, and the fourth qualified theta half wave 810 are downward sloping, while the third qualified theta half wave 808 is upward sloping.

Returning to the first qualified theta half wave 804, this half wave is divided into "n" equal portions, wherein each portion is bounded by an adjacent pair of the dashed vertical lines. In this example, n=3. A phase range is assigned to the portion of the half wave spanning between the dashed vertical lines. In this case the spanned phase range is 180 degrees and is bounded on the left by the half wave maximum 820 at 90 degrees and on the right by the half wave minimum 824 at 270 degrees. Each pair of adjacent dashed vertical lines is allotted a portion of the overall phase range, in this example 60 degrees. Phase range values may be assigned to different portions of a qualified half wave depending, for example, on the half waves similarity in position to a sine wave of similar frequency as shown here.

In this example, the portion of the first qualified theta half wave 804 spanning between the first pair of vertical lines includes the positive peak 820 or local maxima of the first qualified theta half wave and is assigned the phase range of 90 degrees to 150 degrees. The portion of the first qualified theta half wave 804 spanning between the second pair of vertical lines is assigned the phase range of 150 degrees to 210 degrees. The portion of the first qualified theta half wave 804 spanning between the third pair of vertical lines corresponds to the phase range 210 degrees to 270 degrees. The second qualified theta half wave 806 and the fourth qualified theta half wave 810 have the same type of slope, i.e., downward slope, as the first qualified theta half wave 804 and thus are assigned the same phase ranges as the first qualified half wave.

The third qualified theta half wave 808 is upward sloping. Like the other qualified theta half waves 804, 806, 810, the third qualified theta half wave 808 is divided into three portions, wherein each portion is bounded by an adjacent pair of the dashed vertical lines. A phase range is assigned across the span of the dashed vertical lines. The overall phase range is 180 degrees, just like the downward sloping qualified theta half waves 804, 806, 810, however, the overall phase range of the third qualified theta half wave 808 is bound on the left by the half wave minimum 822 at 270 degrees and on the right by the half wave maximum 826 at 90 degrees, which is different from the boundaries of the downward sloping qualified half waves. Each pair of adjacent dashed vertical lines is allotted a portion of the overall phase range. In this example, the portion of the third qualified half wave 808 spanning between the first pair of vertical lines includes the negative peak 822 or local minima of the third qualified theta half wave 808 and is assigned the phase range of 270 degrees to 330 degrees. The portion of the third qualified theta half wave 808 spanning between the second pair of vertical lines is assigned the phase range of 330 degrees to 30 degrees. The portion of the third qualified theta half wave 808 spanning between the third pair of vertical lines is assigned the phase range 30 degrees to 90 degrees.

Figures 9A, 9B, 9C:
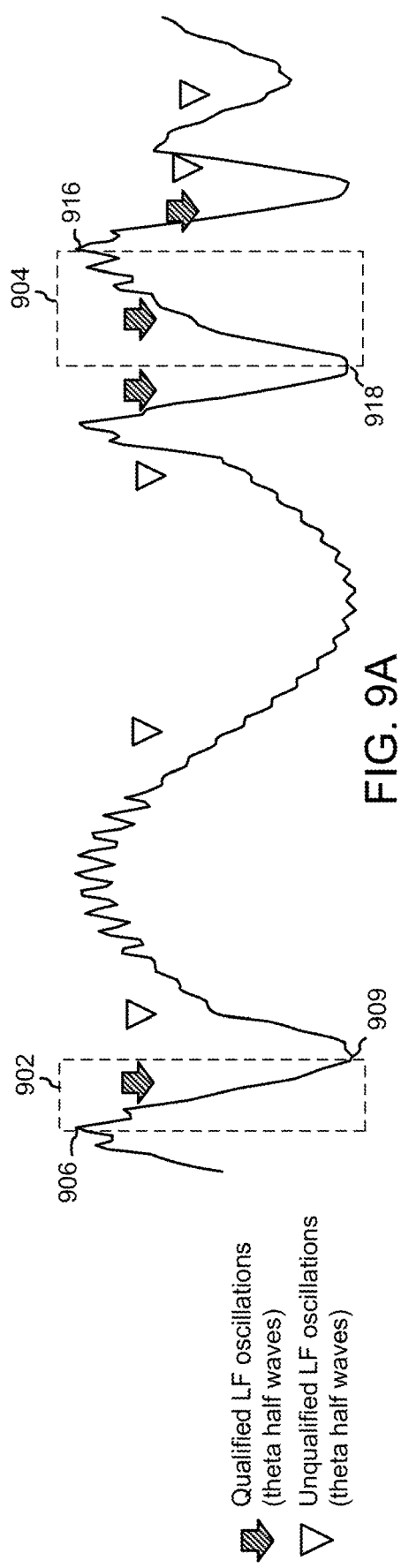
FIGS. 9A-9C illustrate a method of analyzing a region of interest of an electrographic signal characterized by cross-frequency coupling, in which low-frequency signal content or oscillations (e.g., half waves) are divided into phase ranges or phase bins, and associated with a number of data samples of the electrographic signal.

The foregoing partitioning of qualified theta half waves 804, 806, 808, 810 and assignment of phase ranges may be implemented by the implantable medical device through the grouping of signal samples into bins and the correlating of bins to phase ranges. For example, with reference to FIG. 9A, a first qualified theta half wave 902 having a downward slope, and a second qualified theta half wave 904 having an upward slope are highlighted. A detail of the first qualified theta half wave 902, together with its corresponding assignment of signal-sample-groupings to bins, and bins to phase ranges, is illustrated in FIG. 9B. Likewise, a detail of the second qualified theta half wave 904, together with its corresponding signal sample groupings to bins, and bins to phase ranges, is illustrated in FIG. 9C.

With reference to FIGS. 9A and 9B, when processing the first qualified theta half wave 902 the implantable medical device determines that the local maxima 906 of the half wave is at sample number "233," and that the local minima 908 is at sample "250." Based on these determinations, the device identifies that this theta half wave 902 has a downward slope. The device determines the number of signal samples spanning the first qualified theta half wave 902 based on the difference in the sample number of the local minima 908 (sample "233") and the sample number of the local maxima 906 (sample "250"). In this example, there are 18 data samples spanning the first qualified theta half wave 902.

The device groups samples to corresponding phase bins by dividing the total number of data samples spanning the first qualified theta half wave 902 into a number (n). The number (n) may be programmed into the device. In the example of FIG. 9B, n=3 and the 18 samples are thus divided into three bins 910, 912, 914, identified as bins 1, 2, and 3, respectively. The first bin 910 contains samples between sample number 233 to 238, the second bin 912 contains samples between 239 to 244, and the third bin 914 contains samples between 245 to 250. Note that in this example, the number of data samples between the first qualified theta half wave 902 is exactly divisible by the number of bins. In cases where the number of samples is not exactly divisible by the number (n) of bins, the device may choose some bins to be allotted more samples than other bins. The bins that receive more samples may be selected at random.

With reference to FIGS. 9A and 9C, when processing the second qualified theta half wave 904 the implantable medical device determines that the local maxima 916 of the half wave is at sample number "1250," and that the local minima 918 is at sample "1223." Based on these determinations, the device identifies that the second qualified theta half wave 904 has an upward slope. The device determines the number of signal samples between the second qualified theta half wave 904 based on the difference in the sample number of the local maxima 916 (sample "1250") and the sample number of the local minima 918 (sample "1223"). In this example, there are 28 data samples between the second qualified theta half wave 904.

The device groups samples to corresponding bins by dividing the total number of data samples spanning the second qualified theta half wave 904 into a number (n). In the example of FIG. 9C, n=3 and the 28 samples are thus divided into three bins 920, 922, 924, identified as bins 4, 5, and 6 respectively. Since the slope of the second qualified theta half wave 904 is different from the slope of the first qualified theta half wave 902, the bin numbers (bin 4, bin 5, bin 6) assigned to the second qualified theta half wave are different than the bin numbers (bin 1, bin 2, bin 3) assigned to the first qualified theta half wave. If the slopes of the first and second qualified half waves 902, 904 are the same, the same bin numbers are assigned to the samples.

Continuing with FIG. 9C, the fourth bin 920 contains samples between sample number "1223" to "1231," the fifth bin 922 contains samples between "1232" to "1240," and the sixth bin 924 contains samples between "1241" to "1250." Note that the number of bins (n=3) assigned to each of the downward sloping first qualified theta half wave 902 and the upward sloping second qualified theta half wave 904 is the same. As a result, the number of samples in each of bins 4, 5, and 6, of the second qualified theta half wave 904 is greater than the number of samples in bins 1, 2, and 3 of the first qualified theta half wave 902. It is noted that the total number of bins for the two half waves comprising the downward sloping first qualified theta half wave 902 and the upward sloping second qualified theta half wave 904 is 6.

Continuing with FIGS. 9A, 9B, and 9C, the implantable medical device assigns phase ranges to each of the bins 1 through 6. In a perfect sine wave, 90 degrees is the local maxima and 270 degrees is the local minima. Similar phase values may be assigned to similar portions of qualified theta half waves 902, 904 identified by the device. For example, the point in each qualified theta half wave 902, 904 containing the local maxima may be assigned phase 90 degrees and the point in each qualified theta half wave containing the local minima will be assigned phase 270 degrees. This is evident in FIGS. 9B and 9C, wherein the bin 910 (bin 1) containing the local maxima 906 (sample "233") of the first qualified theta half wave 902, and the bin 924 (bin 6) containing the local maxima 916 (sample "1250") of the second qualified theta half wave 904, are each assigned a phase range that includes phase 90 degrees. Likewise, the bin 914 (bin 3) containing the local minima 908 (sample "250") of the first qualified theta half wave 902, and the bin 920 (bin 4) containing the local minima 918 (sample "1223") of the second qualified theta half wave 904, are each assigned a phase range that includes phase 270 degrees.

The cumulative phase range across the total number of bins may be 360 degrees, with the bins of the downward sloping or falling qualified half waves spanning a total of 180 degrees and the bins of the upward sloping or rising qualified half waves also spanning a total of 180 degrees. Within each group of bins, e.g., bins of the downward sloping half waves (bins 1 to 3) and bins of the upward sloping half waves (bins 4-6), the 180 degrees may be evenly divided, with each individual bin spanning 60 degrees.

Computing a Measure of Phase-Amplitude Coupling

Returning to FIG. 5, at block 512, the implantable medical device determines a metric based on counts of oscillations in the higher frequency range, e.g., higher-frequency half waves, or gamma half waves. Specifically, the device determines a metric for each portion of the low-frequency oscillations assigned a phase range or phase bin in block 510. The determined metric is based on a count of oscillations in the higher frequency range, e.g., gamma half waves, that coincide with the portion of the oscillations in the low frequency range, e.g., theta half waves. "Coincide" in this context means that an oscillation in the higher frequency range occurs in the same portion of the brain signal as an oscillation in the low frequency range.

At block 513, the implantable medical device determines an aggregate metric for each assigned phase range or phase bin. The aggregate metric is based on the individual metrics determined for each portion of the detected feature having the phase range or phase bin assigned thereto.

At block 514, the implantable medical device determines a measure of phase-amplitude coupling, e.g., a phase-amplitude coupling index, based on the determined metrics. Detailed descriptions of blocks 512, 513 and 514 follow.

Higher Frequency Oscillation Metrics

In one implementation of determining metrics for use in calculating a measure of phase-amplitude coupling, a metric, e.g., count or number, of oscillations in the high frequency range, e.g., gamma half waves, is determined for each phase range or phase bin, of each oscillation in the lower frequency range, e.g., theta half wave. An aggregate metric is then determined based on the individual metrics.

Figure 10:
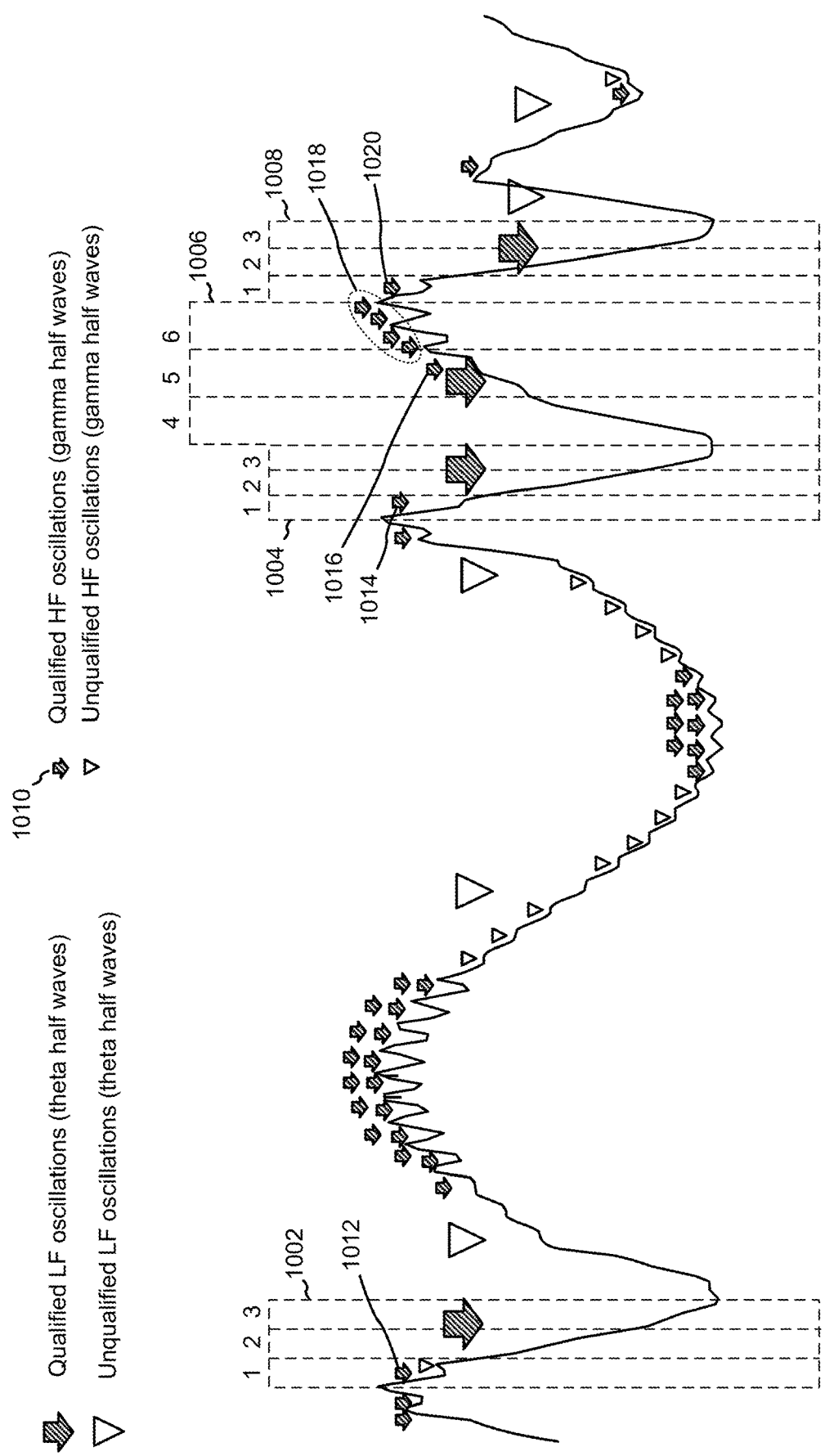
FIG. 10 illustrates a method of analyzing a region of interest of an electrographic signal characterized by cross-frequency coupling, in which cross frequency coupling of oscillations in a low-frequency range (theta) and oscillations in a higher frequency range (gamma) is present.

With reference to FIG. 10, which is an enlarged illustration of the theta-gamma coupling signal of FIG. 9, four qualified oscillations in the low frequency range, e.g., theta half waves 1002, 1004, 1006, 1008, are shown together with qualified oscillations in the higher frequency range, e.g., gamma half waves 1010. Each of the qualified theta half waves 1002, 1004, 1006, 1008 is partitioned into three portions as indicated by the vertical dashed lines, with each portion being assigned to a bin number. The bin number assignments correspond to the assignments described above with respect to FIGS. 9A, 9B, and 9C; and are indicated in FIG. 10 by numbers 1 through 6 at the top of the dashed boxes.

The implantable medical device counts the number of qualified gamma half waves 1010 that are detected in each bin of each qualified theta half wave 1002, 1004, 1006, 1008 or more specifically within the data samples in each bin of a qualified theta half wave. The bins correspond to phase ranges and qualified gamma half waves 1010 detected within the data samples in a particular bin are considered to "coincide" with the portion of the qualified theta half wave 1002, 1004, 1006, 1008 associated with the particular bin.

These counts of qualified gamma half waves 1010 correspond to individual metrics. For example, for qualified theta half wave 1002, the device detects one qualified gamma half wave 1012 in bin 1, and no qualified gamma half waves in either of bin 2 or bin 3. For the qualified theta half wave 1004, the device detects one qualified gamma half wave 1014 in bin, and no qualified gamma half waves in either of bin 2 or bin 3. For qualified theta half wave 1006, the device detects no qualified gamma half waves in bin 4, one qualified gamma half wave 1016 in bin 5, and four qualified gamma half waves 1018 in bin 6. For qualified theta half wave 1008, the device detects one qualified gamma half wave 1020 in bin 1, and no qualified gamma half waves in either of bin 2 or bin 3. A table summarizing these individual metrics, e.g., counts, follows:

TABLE 1

|  | Bin 1 (phase 90 to 150) | Bin 2 (phase 150 to 210) | Bin 3 (phase 210 to 270) | Bin 4 (phase 270 to 330) | Bin 5 (phase 330 to 30) | Bin 6 (phase 30 to 90) |
| --- | --- | --- | --- | --- | --- | --- |
| # of qualified gamma HWs (for theta HW 1002) | 1 | 0 | 0 | n/a | n/a | n/a |
| # of qualified gamma HWs (for theta HW 1004) | 1 | 0 | 0 | n/a | n/a | n/a |
| # of qualified gamma HWs (for theta HW 1006) | n/a | n/a | n/a | 0 | 1 | 4 |
| # of qualified gamma HWs (for theta HW 1008 | 1 | 0 | 0 | n/a | n/a | n/a |
| Aggregate (sum) | 3 | 0 | 0 | 0 | 1 | 4 |

In Table 1, an aggregate metric for each bin is obtained by summing the individual metrics within a bin. Alternatively, the aggregate metric may be a statistical measure of the individual metrics, such as an average of the individual metrics within a bin.

The brain signal of FIG. 10 is approximately one second in duration to allow for clarity of illustration. Accordingly, the total number of gamma half wave counts in Table 1 is small. However, as previously described, the implantable medical device may process a brain signal of a particular duration for a particular application through the use of a programmable processing window 612. For example, a user may program the device to process a 5 second duration of the brain signal. In this case, the number of gamma half wave counts would likely be higher and thereby present more data upon which to base a measure of phase-amplitude coupling.

In another implementation of determining metrics to be used to calculate a measure of phase-amplitude coupling, the metric, e.g., count or number, of gamma half waves is normalized relative to a measure of the duration of the portion of the low-frequency oscillation or the duration of the phase bin. The measure of the duration of the low-frequency oscillation portion or phase bin may correspond to the number of data samples in the portion or phase bin. Accordingly, a normalized count of gamma half waves may be obtained by dividing the number of gamma half waves within a bin of a theta half wave by the number of samples in the bin. The gamma half waves may be qualified only, or both qualified and unqualified.

With reference to FIGS. 9A, 9B, 9C, and 10, in an example of the process of normalizing gamma half waves, the implantable medical device counts the number of qualified gamma half waves 1010 that are detected in each bin of each qualified theta half wave 1002, 1004, 1006, 1008, that is, within the data samples in each bin of a qualified theta half wave. For example, for qualified theta half wave 1002, the device detects one qualified gamma half wave 1012 in bin 1, and no qualified gamma half waves in either of bin 2 or bin 3. As shown in FIG. 9B, bin 1 includes 6 data samples. Accordingly, the individual metric for bin 1 of qualified theta half wave 1002 is 1/6. For qualified theta half wave 1004, the device detects one qualified gamma half wave 1014 in bin 1, and no qualified gamma half waves in either of bin 2 or bin 3. Bin 1 includes 6 data samples, so the individual metric for bin 1 of qualified theta half wave 1004 is 1/6.

For qualified theta half wave 1006, the device detects no qualified gamma half waves in bin 4, one qualified gamma half wave 1016 in bin 5, and four qualified gamma half waves 1018 in bin 6. As shown in FIG. 9C, each of bin 4 and bin 5 includes 9 data samples. Accordingly, the individual metric for bin 4 of qualified theta half wave 1002 is 1/9, and the individual metric for bin 5 is 4/9. For qualified theta half wave 1008, the device detects one qualified gamma half wave 1020 in bin 1, and no qualified gamma half waves in either of bin 2 or bin 3. As shown in FIG. 9B, bin 1 includes 6 data samples. Accordingly, the individual metric for bin 1 of qualified theta half wave 1008 is 1/6. A table summarizing these counts follows:

TABLE 2

|  | Bin 1 (phase 90 to 150) | Bin 2 (phase 150 to 210) | Bin 3 (phase 210 to 270) | Bin 4 (phase 270 to 330) | Bin 5 (phase 330 to 30) | Bin 6 (phase 30 to 90) |
| --- | --- | --- | --- | --- | --- | --- |
| # of qualified gamma HWs/ number of data samples (for theta HW 1002) | 1/6 | 0 | 0 | n/a | n/a | n/a |
| # of qualified gamma HWs/ number of data samples (for theta HW 1004) | 1/6 | 0 | 0 | n/a | n/a | n/a |
| # of qualified gamma HWs/ number of data samples (for theta HW 1006) | n/a | n/a | n/a | 0 | 1/9 | 4/10 |
| # of qualified gamma HWs/ number of data samples (for theta HW 1008) | 1/6 | 0 | 0 | n/a | n/a | n/a |
| Aggregate (sum) | 3/6 | 0 | 0 | 0 | 1/9 | 4/10 |

The individual metrics of each bin are further processed by aggregating the metrics. For example, an aggregate metric of a bin may be obtained by summing the individual metrics associated with the bin. This type of aggregation is reflected in Table 2. Alternatively, the aggregate may be a statistical measure of the individual metrics associated with the bin, such as an average.

Measure of Phase-Amplitude Coupling

Returning to FIG. 5, after determining metrics for the oscillations in the higher frequency range, e.g., gamma half waves, the process proceeds to block 514, wherein the implantable medical device determines a measure of phase-amplitude coupling or a PAC score based on the metrics.

In one implementation described above, referred to as the "Min/Max" implementation, a PAC score is computed as the difference between the maximum aggregate metric and minimum aggregate metric across all assigned phase ranges, as follows:

$$\text{PAC score} = \text{max entry} - \text{min entry} \qquad \text{(Eq. 1)}$$

where, max entry=the maximum aggregate metric, and min entry=the minimum aggregate metric If the PAC score is 0, then gamma has no preference for the different phases of theta, and phase-amplitude coupling is considered absent. A non-zero PAC score indicates that measurable phase-amplitude coupling is present. With reference to the aggregate metrics in Table 1, the PAC score=4−0=4. A PAC score of 4 reflects measurable gamma coupling with theta. In other words, a PAC score of 4 reflects the presence of coupling in time between two different frequencies. The location of the theta-gamma coupling corresponds to the bin having the maximum aggregate metric. In Table 1, the largest aggregate metric is 4, and is in bin 6, which corresponds to phases between 30 and 90 degrees. Accordingly, in the example of Table 1, most oscillations in the higher frequency range, e.g., gamma oscillations, are coupled to phases between 30 and 90 degrees of oscillations in the low frequency range, e.g., theta oscillations.

With respect to the aggregate metrics in Table 2, the PAC score=3/6−0=0.5. A PAC score of 0.5, as in Table 2, reflects measurable gamma coupling with theta. In Table 2, the largest aggregate metric is 3/6, and is in bin 1, which corresponds to phase 90 to 150. Accordingly, in the example of Table 2, most of the oscillations in the higher frequency range, e.g., gamma oscillations, are coupled to phase 30 to 90 of oscillations in the low frequency range, e.g., theta oscillations.

The foregoing process of calculating a measure of phase-amplitude coupling may be performed periodically, e.g., once an hour, once a minute, etc., or continuously, on a rolling basis. In the case of periodic performance, the implantable medical device captures the portion of a brain signal within a processing window 612, such as shown in FIG. 6, and calculates a measure of phase-amplitude coupling based on that portion. The duration of the processing window may range from several milliseconds to several hundreds of seconds.

In the case of continuous performance, the implantable medical device continuously analyzes a continuously sensed brain signal and detects for qualified oscillations in the low frequency range, and for qualified oscillations in the higher frequency range that coincide with qualified oscillations in the low frequency range. Metrics of oscillations in the higher frequency range, as described above, are computed on a rolling basis, using a current set of metrics. The current set of metrics may be the most metrics obtained from a most recent "x" seconds of the brain signal, where "x" may be programmed into the device.

Other Calculations of Phase-Amplitude Coupling

In another implementation, instead of computing a PAC score using Eq. 1, a set of rules may be applied to the counts in the bins to determine if significant phase-amplitude coupling is present. For example, the implantable medical device may be programmed to monitor the total count of second-frequency oscillations in the higher frequency range, e.g., gamma half waves, in each of a number of bins and then process the collection of counts to determine if the counts are skewed toward a subset of the bins. Essentially, the device processes the counts to determine if the majority of the counts occur in a few bins, or if there is a more even distribution of counts across all bins. For example, if there are 100 counts and ten bins, the device may conclude that the counts are not skewed if there are 10 counts in each of the ten bins. However, if three of the bins each contain 30 counts, and the remaining 10 counts are dispersed among the remaining seven bins, then the device may conclude that the counts are skewed.

In terms of a measure of phase-amplitude coupling, a case where the counts are skewed to a small number of bins implies that there is a high level of phase-amplitude coupling, whereas a more even distribution of the counts among the bins implies a low level of phase-amplitude coupling. In general terms, the device may process the counts to determine if more than x % of entries in the bins are distributed among y % of the total number of bins. The values of x and y determine whether the outcome indicates a high measure of phase-amplitude coupling or a low measure. For example, if x=80 and y=30, then an outcome that indicates that 80% of the counts are distributed among 30% of the bins indicates a skewing of counts and a high measure of phase-amplitude coupling. Whereas, if x=80 and y=80, then an outcome that indicates that 80% of the counts are distributed among 80% of the bins indicates an even distribution of counts and a low measure of phase-amplitude coupling.

As noted above, the counts in the bins may be computed on a rolling basis on x seconds worth of data. In this way, the counts in the bins are continuously updated with a moving processing window 612 that runs over new portions of a continuously sensed brain signal, as the brain signal becomes available. Counts in the bins correspond to the neural signal in the moving processing window and as the window moves to the next brain signal sample(s), the older counts in the bin that no longer correspond to the brain signal within the new processing window are overwritten by new entries. As previously described, the user may select the processing window to be a few milliseconds long or several seconds depending on the application. The device may be programmed to store (at least temporarily) all counts in the bins for subsequent downloading to an external computer for further processing and viewing by a user.

Measure of Phase-Amplitude Coupling Based on Qualified and Unqualified Half Waves As previously described, in an alternate implementation, both qualified and certain unqualified half waves may be used to compute a measure of phase-amplitude coupling. If an oscillation in a low frequency range, e.g., a theta half wave, is deemed unqualified because of its amplitude not meeting the minimum and maximum amplitude threshold criteria, the unqualified theta half wave may still be processed together with qualified oscillations in the low frequency range to calculate a measure of phase-amplitude coupling.

The unqualified nature of these theta half waves is accounted for in the process by assigning a weight to the bins into which the unqualified theta half waves fall. A bin may be assigned a weight that depends on the difference or the ratio between the amplitude of the unqualified theta half wave and the minimum or maximum amplitude threshold the theta half wave failed to satisfy. For example, if the amplitude of the theta half wave is 2 mV and the minimum amplitude threshold is at 2.5 mV, a weight of 2/2.5, which equals 0.8, may be assigned to the bins corresponding to this particular unqualified theta half wave.

Similarly, if a theta half wave is deemed unqualified because its duration does not satisfy the minimum and maximum duration threshold criteria, the unqualified theta half wave may be processed together with qualified theta half wave to calculate a measure of phase-amplitude coupling. The unqualified nature of these theta half waves is accounted for in the process by assigning a weight to the bins into which such unqualified theta half waves fall. For example, a bin may be assigned a weight that depends on the difference or the ratio between the duration of the unqualified half wave and the duration threshold the theta half wave failed to satisfy. For example, if the duration of the theta half wave is 3 msec and the maximum duration threshold is 2.8 msec, a weight of $1-((\beta-2.8|)/2.8)$, which equals 0.93, may be assigned to the bins corresponding to this particular unqualified half wave.

For theta half waves that do not meet amplitude and duration constraints, both amplitude and duration threshold based weights may be combined to derive a new weight in such cases. The product of the respective weights may be served as a combined weight. For example, if the amplitude threshold weight is 0.8 and the duration threshold weight is 0.93, the combined weight would be 0.8*0.93=0.74.

Figure 11:
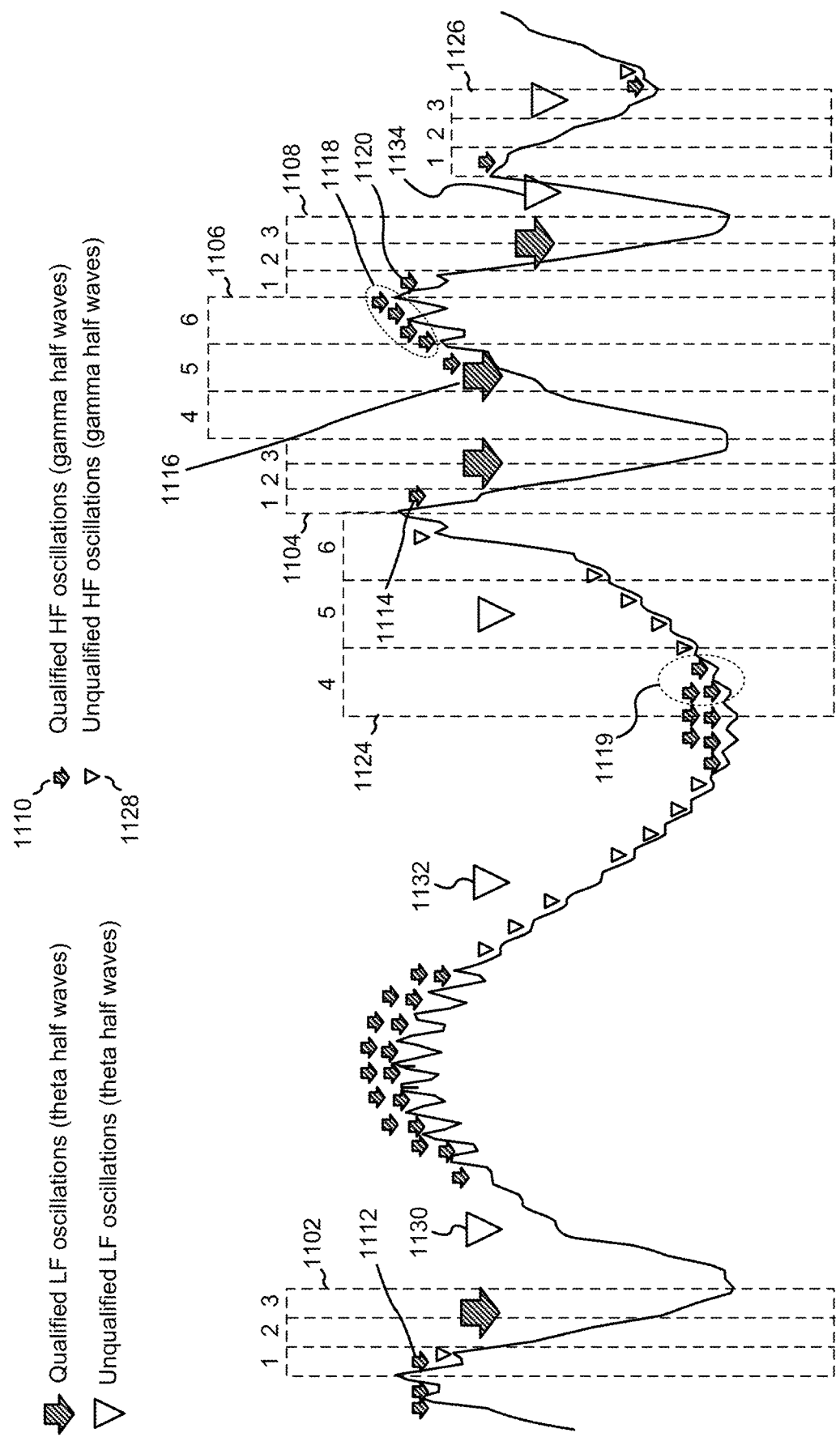
FIG. 11 illustrates another method of analyzing a region of interest of an electrographic signal characterized by cross-frequency coupling, in which cross frequency coupling of oscillations in a low-frequency range (theta) and oscillations in a higher frequency range (gamma) is present.

With reference to FIG. 11, which is an enlarged illustration of the theta-gamma coupled signal of FIG. 8, four qualified oscillations in the low frequency range, e.g., theta half waves 1102, 1104, 1106, 1108, and two selected unqualified oscillations in the low frequency range, e.g., unqualified theta half waves 1124, 1126, are shown together with qualified oscillations in the higher frequency range, e.g., gamma half waves 1110 and unqualified oscillations in the higher frequency range, e.g., gamma half waves 1128. In this example, the unqualified theta half waves 1124, 1126 are selected for analysis along with the qualified theta half waves 1102, 1104, 1106, 1108 because of their failure to satisfy the amplitude criteria, while the other three unqualified theta half waves 1130, 1132, 1134 are excluded from the analysis for not meeting the duration criteria. In other instances, half waves that are unqualified based on duration may be selected for inclusion in the analysis over those that are unqualified based on amplitude. In other cases, all unqualified half waves may be selected for analysis.

Continuing with FIG. 11, each of the qualified theta half waves 1102, 1104, 1106, 1108 is partitioned into three portions as indicated by the vertical dashed lines, with each portion being assigned to a bin number. Each of the unqualified theta half waves 1124, 1126 is also partitioned into three portions as indicated by the vertical dashed lines, with each portion being assigned to a bin number. The bin number assignment corresponds to the assignments described above with respect to FIGS. 9B and 9C, and are indicated in FIG. 11 by numbers 1 through 6 at the top of the dashed boxes.

The implantable medical device counts the number of qualified gamma half waves 1110 that are detected in each bin of each qualified theta half wave 1102, 1104, 1106, 1108 or more specifically within the data samples in each bin of a qualified theta half wave. The bins correspond to phase ranges and qualified gamma half waves 1110 detected within the data samples in a particular bin are considered to "coincide" with the portion of the theta half wave associated with the particular bin.

These counts of qualified gamma half waves 1110 correspond to individual metrics. For example, for qualified theta half wave 1102, the device detects one qualified gamma half wave 1112 in bin 1, and no qualified gamma half waves in either of bin 2 or bin 3. For qualified theta half wave 1104, the device detects one qualified gamma half wave 1114 in bin 1, and no qualified gamma half waves in either of bin 2 or bin 3. For qualified theta half wave 1106, the device detects no qualified gamma half waves in bin 4, one qualified gamma half wave 1116 in bin 5, and four qualified gamma half waves 1118 in bin 6. For qualified theta half wave 1108, the device detects one qualified gamma half wave 1120 in bin 1, and no qualified gamma half waves in either of bin 2 or bin 3. These four theta half waves 1102, 1104, 1106, 1108 are qualified. Thus, the weights associated with each of these theta half waves is 1.

The implantable medical device also counts the number of qualified gamma half waves 1110 that are detected in each bin of each unqualified theta half wave 1124, 1126. For example, for unqualified theta half wave 1124, the device detects 3 qualified gamma half waves 1119 in bin 4 and no qualified gamma half waves in either of bin 5 or bin 6. For unqualified theta half wave 1126, the device detects one qualified gamma half wave 1120 in bin 1, and no qualified gamma half waves in either of bin 2 or bin 3. These two theta half waves 1124 and 1126 are unqualified. Thus, a lower weight is associated with each of these.

As described above, the weight for an unqualified theta half wave may be based on the difference or the ratio between the amplitude of the unqualified theta half wave and the minimum or maximum amplitude threshold the theta half wave failed to satisfy. The weight may also be based on the difference or the ratio between the duration of the unqualified half wave and the duration threshold the theta half wave failed to satisfy. In this example, theta half wave is 1124 assigned a weight of 0.7, and the theta half wave 1126 is assigned a weight of 0.4. A table summarizing these individual metrics, e.g., counts, and weights follows:

TABLE 3

| | Bin 1 (phase 90 to 150) | Bin 2 (phase 150 to 210) | Bin 3 (phase 210 to 270) | Bin 4 (phase 270 to 330) | Bin 5 (phase 330 to 30) | Bin 6 (phase 30 to 90) | Weight based on theta HW |
|---|---|---|---|---|---|---|---|
| # of qualified gamma HWs (theta HW 1102) | 1 | 0 | 0 | n/a | n/a | n/a | 1 |
| # of qualified gamma HWs | 1 | 0 | 0 | n/a | n/a | n/a | 1 |

TABLE 3-continued

|  | Bin 1 (phase 90 to 150) | Bin 2 (phase 150 to 210) | Bin 3 (phase 210 to 270) | Bin 4 (phase 270 to 330) | Bin 5 (phase 330 to 30) | Bin 6 (phase 30 to 90) | Weight based on theta HW |
|---|---|---|---|---|---|---|---|
| # of qualified gamma HWs (theta HW 1104) | n/a | n/a | n/a | 0 | 1 | 4 | 1 |
| # of qualified gamma HWs (theta HW 1106) | 1 | 0 | 0 | n/a | n/a | n/a | 1 |
| # of qualified gamma HWs (theta HW 1108) | n/a | n/a | n/a | 3 (weighted to 2.1) | 0 | 0 | 0.7 |
| # of unqualified gamma HWs (theta HW 1124) | 1 (weighted to 0.4) | 0 | 0 | n/a | n/a | n/a | 0.4 |
| # of unqualified gamma HWs (theta HW 1126) |  |  |  |  |  |  |  |
| Aggregate (average) | 0.85 | 0 | 0 | 1.05 | 1 | 2 |  |

The entries across the rows of Table 3 represent the counts of qualified gamma half waves detected in the corresponding bins. For those counts associated with an unqualified theta half wave, the weight for the unqualified theta half wave is applied to the count. For example, because theta half wave 1124 is unqualified, the count in bin 4 would be weighted to 2.1 (3×0.7=2.1). Likewise, because theta half wave 1126 is unqualified, the count in bin 1 would be weighted to 0.4 (1×0.4=0.4). In the example of Table 3, the aggregate value for a bin is calculated by calculating an average of the counts in the bin. For bin 1, the aggregate is (1+1+1+0.4)/4=0.85. For bin 4, the aggregate is (0+2.1)/2=1.05. For bin 6, the aggregate is (4+0)/2=2. The PAC score may be calculated using Eq. 1 above, which results in PAC score=2−0=2.

In another implementation, unqualified oscillations in the higher frequency range, e.g., gamma half waves, may also be processed. Similar weighing functions as described with respect to unqualified theta half waves may be applied for oscillations in the higher frequency range, e.g., gamma half waves, that are unqualified. However, in the case of an unqualified gamma half wave a weight is applied to the individual count of the gamma half wave. For example, if there are two qualified gamma half waves and one unqualified gamma half wave in bin 2, and the unqualified gamma half wave has an amplitude threshold weight of 0.8, the individual counts of the two qualified gamma half waves would be unweighted and thus equal to 1, and the individual count for the one unqualified gamma half wave would be weighted and thus equal to (1*0.8)=0.8. Thus, the aggregate metric for bin 2 would be: 1+1+0.8=2.8. If the theta half wave in which the unqualified gamma half wave coincides happens to be an unqualified theta half wave, the individual count of the unqualified gamma half wave may be further weighted by the weight of the unqualified theta half wave. Continuing with the preceding example, if the unqualified gamma half wave weighted to 0.8 coincides with an unqualified theta half wave weighted to 0.4, then the aggregate metric for bin 2 would be: 1+1+(0.8*0.4)=2.32.

Applications of Phase-Amplitude Coupling

Figure 12:
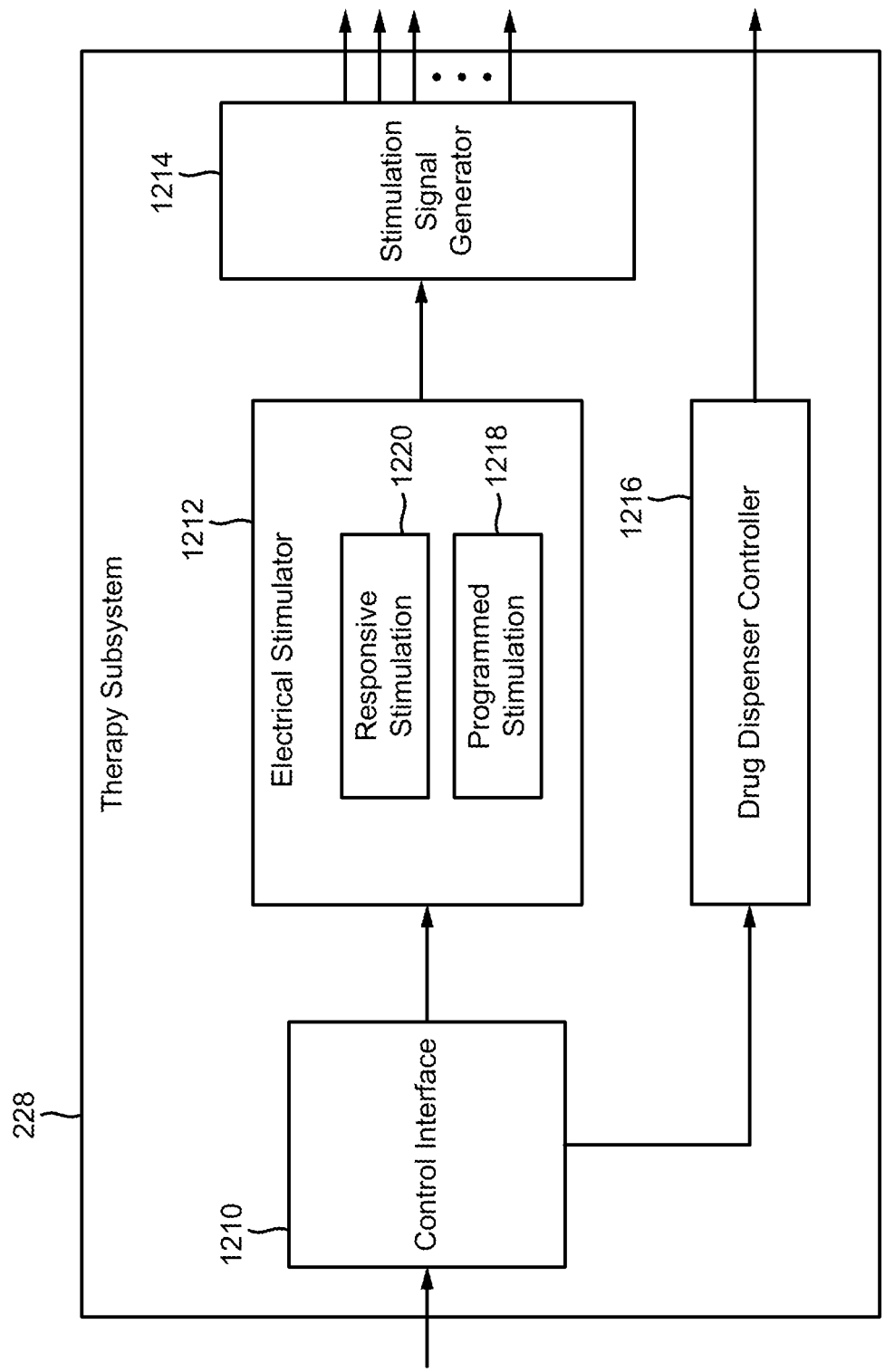
FIG. 12 is a block diagram of the therapy subsystem of FIG. 3, illustrating some of its functional components.

The implantable medical device may be configured to deliver neuromodulation therapy to the patient based on measures of phase-amplitude coupling or PAC scores. To this end, and with reference to FIGS. 2 and 12, the neurostimulator 110 may include a therapy subsystem 228 configured to delivery neuromodulation therapy in one or more forms, including for example electrical stimulation and drug delivery.

The therapy subsystem 228 includes a control interface 1210, which receives commands, data, and other information from the CPU 240, the memory subsystem 238, and the detection subsystem 226. The control interface 1210 uses the received commands, data, and other information to control an electrical stimulator 1212, which in turn, controls a stimulation signal generator 1214. The stimulation signal generator 1214 is configured to generate electrical pulses and is capable of being coupled to one or more electrodes 212a-212d, 214a-214d through the electrode interface 220. The stimulation signal generator 1214 receives commands and data from the electrical stimulator 1212 and generates electrical stimulation signals having the desired characteristics that are properly time-correlated and applied to neurological tissue through associated electrodes.

The electrical stimulator 1212 is adapted to control the stimulation signal generator to provide electrical stimulation signals appropriate for application to neurological tissue. This can be accomplished in different manners. For example, in applications of therapy in response to measures of phase-amplitude coupling to be described below, it may be advantageous in some circumstances to provide programmed stimulation in the form of a substantially continuous stream of pulses, or on a scheduled basis. This form of stimulation, sometimes referred to as "programmed stimulation," is provided by a programmed stimulation function 1218 of the electrical stimulator 1212. Therapeutic stimulation may also be provided in response to abnormal events or measures of phase-amplitude coupling detected by the data analysis functions of the detection subsystem 226. This form of stimulation, namely "responsive stimulation," is provided by a responsive stimulation function 1220 of the electrical stimulator 1212. The neurostimulation therapy may be applied in an effort to terminate a present or predicted undesired neurological event, such an epileptic seizure or tremor due to Parkinson's, or to improve cognitive ability of a patient, such as memory improvement.

The control interface 1210 may also use the received commands, data, and other information to control a drug dispenser controller 1216, which is adapted to selectively allow the release of a drug or other therapeutic agent from a drug dispenser to one or more desired sites, within or near the patient's brain or elsewhere in the body. As is the case with therapeutic electrical stimulation, drug therapy can be performed in response to a detected neurological event or condition, on a substantially continuous basis or scheduled. An example drug dispenser configurable for use with the drug dispenser controller 1216 is described in U.S. Pat. No. 8,190,270 titled "Refillable Reservoir Lead Systems," the disclosure of which is incorporated herein by reference.

The control interface 1210 may continuously or periodically receive measures of phase-amplitude coupling or PAC scores from the data analyzer 314. The control interface 1210 is configured to process these measures or scores based on intended applications of such measures. For example, the control interface 1210 may act on each received PAC score individually by comparing a just-received, or current PAC score against a programmed threshold and initiating neuromodulation therapy based on the comparison outcome.

In other implementations, the control interface 1210 may be configured to act on plurality of received PAC scores by determining a PAC index based on one or more individual PAC scores, and applying the PAC index to a rule to determine whether therapy should be delivered. The PAC index may be a PAC score, or it may be a statistical measure, e.g., mean, median, max or minimum, based on the most recent "x" number of PAC scores, or may be a trend, e.g., increasing or decreasing, in a series of individual PAC scores or in a series of individual PAC indices, where each index itself is based on statistical measures of PAC scores. The rule may be based on a comparison outcome between a PAC index and a PAC index criterion. If a PAC index computed by the control interface 1210 satisfies the PAC index criterion, the device may deliver therapy. For example, if the comparison outcome indicates that the PAC index exceeds a threshold corresponding to the PAC index criterion, the device may deliver therapy. In a different application, stimulation may be delivered when the comparison outcome indicates that the PAC index falls below the threshold. In yet another application, an implantable medical device may adjust its stimulation parameters based on the PAC index comparison outcome. The PAC index criterion or threshold may correspond to a value that indicates the presence of a meaningful coupling between theta and gamma frequencies (i.e., significant PAC) that warrants neuromodulation therapy, in an effort to either increase the measure of phase-amplitude coupling or decrease the measure of phase-amplitude coupling.

Examples of areas or fields of use for the application neuromodulation therapy based on measures of phase-amplitude coupling are disclosed below.

Epilepsy

An example application of neuromodulation therapy based on measures of phase-amplitude coupling relates to epilepsy. Regarding this application, it is known that phase-amplitude coupling increases at seizure onsets. C. Avarado-Rojas, M. Valderrama, A. Fouad-Ahmed, H. Feldwisch-Drentrup, M. Ihle, C. A. Teixeira, F. Sales, A. Schulze-Bonhage, C. Adam, A. Dourado, S. Charpier, V. Navarro, and Quyen M. Le Van. Slow modulations of high-frequency activity (40-140-Hz) discriminate preictal changes in human focal epilepsy. *Sci Rep* 4:4545, 2014.

Accordingly, measures of phase-amplitude coupling based on brain signals that are monitored and processed in real time by the implantable medical device using an embodiment comprising a technique disclosed herein, may serve as a biomarker of seizure onset. Such a biomarker may be useful for diagnostic purposes (e.g., determining the nature of the onset of a seizure for the patient) as well as for treatment purposes (e.g., using the occurrence of a seizure onset to trigger a therapy to modulate neural activity in the hopes of stopping the seizure or at least reducing its severity).

In one implementation, a measure of PAC computed from brain signals sensed from a patient just prior to a seizure may serve as a PAC index criterion against which subsequent PAC indices derived measures of phase-amplitude coupling obtained in real time may be monitored. A subsequent PAC index that falls within a specified range of the PAC index criterion, or a series of PAC scores that are trending toward the PAC index criterion may serve as an indication of a seizure onset. Similarly, a measure of phase-amplitude coupling computed from brain signals sensed from a patient while the patient is at a baseline state of neural activity (e.g., not in a seizure onset state or seizure state) may serve as a PAC index criterion against which subsequent PAC indices may be monitored. A subsequent PAC index that falls outside an acceptable range of the PAC index criterion (e.g., measures that are too high or too low), or a series of PAC scores that are trending away from the PAC index criterion may serve as an indication of an impending seizure.

An indication of a seizure onset or an impending seizure may trigger the implantable medical device (or a related implanted device) to deliver a form of electrical stimulation to the neural tissue, with an objective of reducing the effect of the seizure that develops after the onset and stopping or reducing the likelihood or severity of the seizure. The device may also send an alert signal to the patient, so the patient may move herself to a safe location in anticipation of a seizure.

Memory

Another example application of neuromodulation therapy based on measures of phase-amplitude coupling relates to memory improvement. Regarding this application, the strength of phase-amplitude coupling, particularly theta-gamma coupling, has been shown to be directly correlated with an increase in performance accuracy in memory tasks. A. B. Tort, R. W. Komorowski, J. R. Manns, N. J. Kopell, and H. Eichenbaum. Theta-gamma coupling increases during the learning of item-context associations. *Proc Natl. Acad Sci U.S.A.* 106 (49):20942-20947, 2009.

Accordingly, measures of phase-amplitude coupling (e.g., theta-gamma coupling) obtained in real time by an implantable medical device using a technique disclosed herein, may provide a useful measure that serves as an indicator of memory performance under certain circumstances. The device may deliver a neuromodulation therapy (e.g., electrical stimulation delivered according to a particular regimen or protocol) designed to keep the measure of the theta-gamma coupling at or near a value correlated to maintaining or improving a patient's memory quality. This application may be beneficial to patients suffering from a range of memory related disorders such as in Alzheimer's, traumatic brain injury, or in epilepsy where memory deficits are common.

In one implementation, a PAC index criterion corresponding to a measure of PAC correlated to maintaining or improving a patient's memory quality is obtained. The PAC index criterion may be computed from brain signals sensed from a patient while the patient is not experiencing memory loss. The PAC index criterion may also be computed from corresponding measures obtained across a patient population that exhibit above average memory capabilities. Subsequent PAC indices obtained in real time may be monitored relative to the PAC index criterion. For example, a PAC index that falls below the PAC index criterion by a specified amount may serve as an indication of poor memory quality for the patient.

An indication of poor memory quality may trigger the implantable medical device (or a related implanted device) to deliver a form of electrical stimulation to the neural tissue, with an objective of maintaining or improving a patient's memory quality, and helping the patient with information processing.

Abnormal Neural Coupling

Another group of applications relate to neuromodulation strategies to treat abnormal neural coupling. Regarding this application, studies have shown that electrical stimulation can be used to evoke cross-frequency coupled neuronal oscillations. P. R. Shirvalkar, P. R. Rapp, and M. L. Shapiro. Bidirectional changes to hippocampal theta-gamma comodulation predict memory for recent spatial episodes. *Proc Natl. Acad Sci U.S.A.* 107 (15):7054-7059, 2010. Studies have also shown that phase-amplitude coupling is vital for certain brain functions such as cognitive processing. For example, it has been proposed that theta-gamma coupling of neural signals is a neural mechanism by which information processing is coordinated across multiple spatiotemporal scales in the brain. R. T. Canolty and R. T. Knight. The functional role of cross-frequency coupling. Trends Cogn Sci 14 (11):506-515, 2010.

Thus, measures of phase-amplitude coupling (e.g., theta-gamma coupling) obtained in real time by an implantable medical device using a technique disclosed herein, may provide a useful measure that serves as an indicator of the quality of cognitive processing. PAC indices that deviate from a PAC index criterion or that fall outside a pre-determined range of the PAC index criterion, may serve as an indication of impaired cognitive processing. The device may deliver a neuromodulation therapy (e.g., electrical stimulation delivered according to a particular regimen or protocol) designed to keep the measure of the theta-gamma coupling at or near a value correlated to maintaining or improving a patient's cognitive processing.

In these applications, an implantable medical device may be configured to obtain PAC indices based on measures of phase-amplitude coupling within a single brain area or between two brain areas that exhibit abnormal coupling. Measure of phase-amplitude coupling within a single brain area are computed based on brain signals sensed by a sensor (e.g., pair of electrodes) place in or on the single brain area. Measure of phase-amplitude coupling between two brain areas are computed based on brain signals sensed by a sensor that spans the two areas (e.g., a first electrode in or on a first brain area and a second electrode in or on a second brain area). Electrical stimulation may be delivered by the device in accordance with one or more of the stimulation strategies described below, to increase or decrease the measure of phase-amplitude coupling within a single brain area or between two brain areas.

FIG. 13A-13G are illustrations of various waveforms representing different electrical stimulation strategies for effecting changes in measures of phase-amplitude coupling. For ease of illustration, the stimulation strategies represented in FIGS. 13A-13G show electrical stimulation in the form of unipolar square wave pulses. Other, more complex, pulse waveforms may be used, including for example, charge-balanced biphasic waveforms with rectangular, exponential, triangular, Gaussian, and sinusoidal stimulus pulse shapes.

Figure 13A:
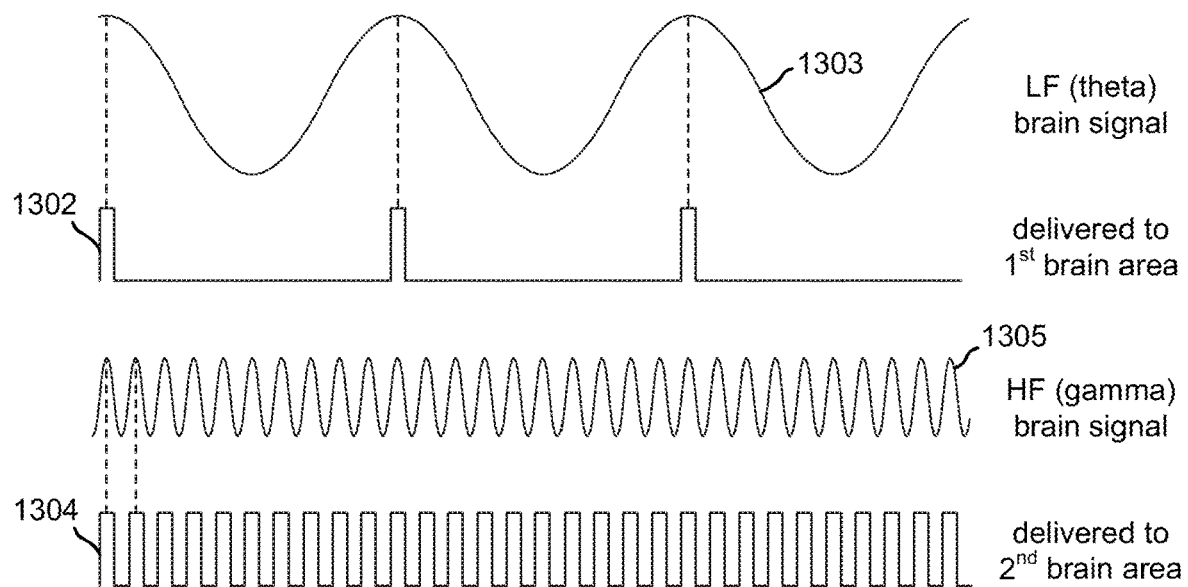
FIG. 13A-13G are illustrations of various waveforms representing different electrical stimulation strategies for effecting changes in measures of phase-amplitude coupling.

With reference to FIG. 13A, in one stimulation strategy, to increase the measure of phase-amplitude coupling between two brain areas, the device may be configured to deliver electrical pulses 1302 to a first area of the brain at a first frequency, and to deliver electrical pulses 1304 to a second area of the brain at a second frequency, greater than the first frequency. For theta-gamma coupling, the lower, first frequency may be at or near the frequency of a filtered theta brain signal 1303 (e.g., within the range of 4-8 Hz) and the higher, second frequency may be at or near the frequency of a filtered gamma brain signal 1305 (e.g. within the range of 25-200 Hz). Delivery of the electrical pulses 1302, 1304 is synchronized or near-synchronized with a fiducial point, such as the maximum amplitudes or any other desired phase, of the respective brain signal 1303, 1305.

Figure 13B:
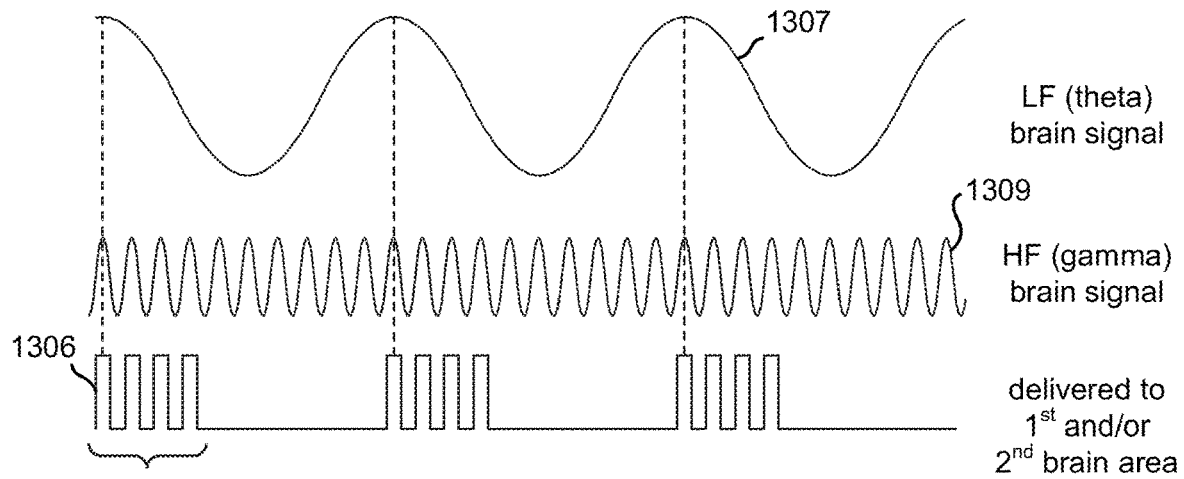

In an alternative stimulation strategy shown in FIG. 13B, to increase the measure of phase-amplitude coupling at either of, or between two brain areas, the device is configured to deliver electrical pulses 1306 at a second, higher frequency in short bursts 1308 which are delivered at a frequency equal to a first, lower frequency. For theta-gamma coupling, the lower burst frequency may be at or near the frequency of a filtered theta brain signal 1307 and the higher, second frequency of the pulses 1306 within each burst 1308 may be at or near the frequency of a filtered gamma brain signal 1309. The start of the pulse bursts 1308 is synchronized or near-synchronized with the maximum amplitudes or other fiducial point of the filtered theta brain signal 1307. Alternatively, delivery of the bursts 1308 may be timed so that the center of the burst is synchronized or near-synchronized with the maximum amplitudes or other fiducial points of the filtered theta brain signal 1307. In either case, this intermittent burst stimulation may be delivered to one or more brain areas.

Figure 13C:
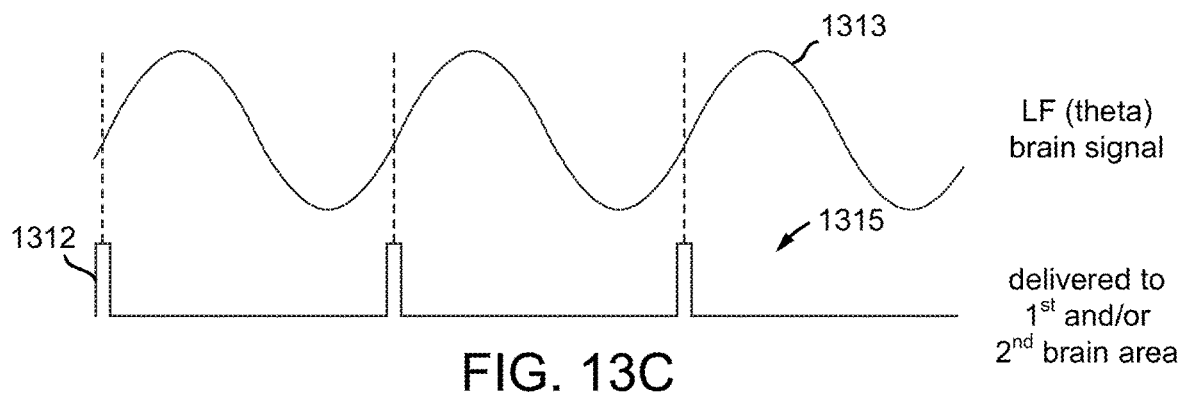

Referring to FIG. 13C, in another stimulation strategy, to decrease the measure of phase-amplitude coupling at either of, or between two brain areas, the device may be configured to deliver electrical pulses 1312 to one or more brain areas at a first, lower frequency at a specific phase, e.g., out of phase, with a filtered low frequency brain signal. For theta-gamma coupling, the lower frequency may be at or near the frequency of a filtered theta brain signal 1313. Each electrical pulse 1312 is delivered at a time offset from the time of a maximum amplitude or other fiducial point of the filtered theta brain signal in an effort to interfere with the theta brain signal. In this case, while delivery of the electrical pulse waveform 1315 is out of phase with the theta brain signal 1313, the pulse waveform and brain signal 1313 are phase locked in that each pulse 1312 in the pulse waveform occurs at the same phase of the brain signal.

Figure 13D:
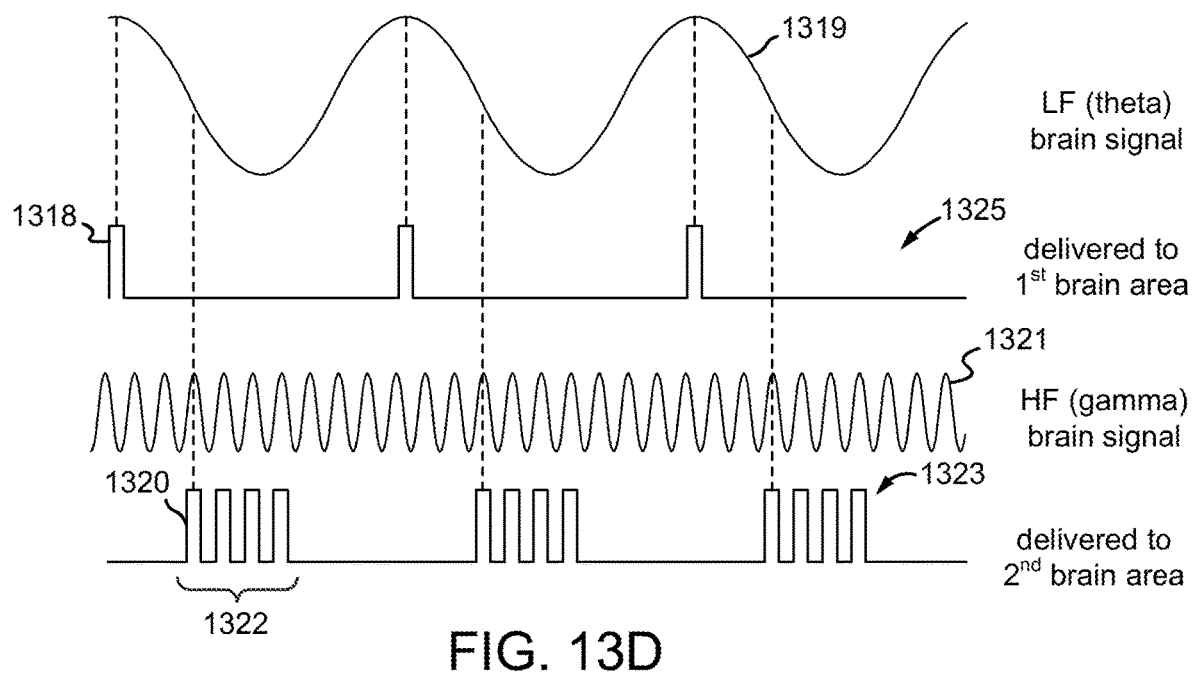

In an alternative stimulation strategy shown in FIG. 13D, to decrease the measure of phase-amplitude coupling between two brain areas, the device may be configured to deliver electrical pulses 1318 to a first area of the brain at a first, lower frequency, and to deliver electrical pulses 1320 to a second area of the brain at a second, higher frequency in short bursts 1322 at a specific phase, e.g., out of phase, with a filtered lower frequency brain signal 1319. For theta-gamma coupling, the lower frequency at which electrical pulses 1318 are delivered and the lower burst frequency at which pulse bursts 1322 are delivered may be at or near the frequency of a filtered theta brain signal 1319. The higher frequency of the pulses 1320 within each burst 1322 may be at or near the frequency of a filtered gamma brain signal 1321. Delivery of the electrical pulses 1318 is synchronized or near-synchronized with a desired phase, e.g., the maximum amplitude or other fiducial point, of the filtered theta brain signal 1319, while the start of the pulse bursts 1322 is offset from the maximum amplitudes or other fiducial points of the filtered theta brain signal. In this case, while delivery of the electrical pulse-burst waveform 1323 to the second brain area is out of phase with the theta brain signal 1319 (and out of phase with the pulse waveform 1325 delivered to the first brain area), the pulse-burst waveform 1323 and the theta brain signal are phase locked in that each burst 1322 in electrical pulse-burst waveform occurs at the same phase of the theta brain signal.

Figure 13E:
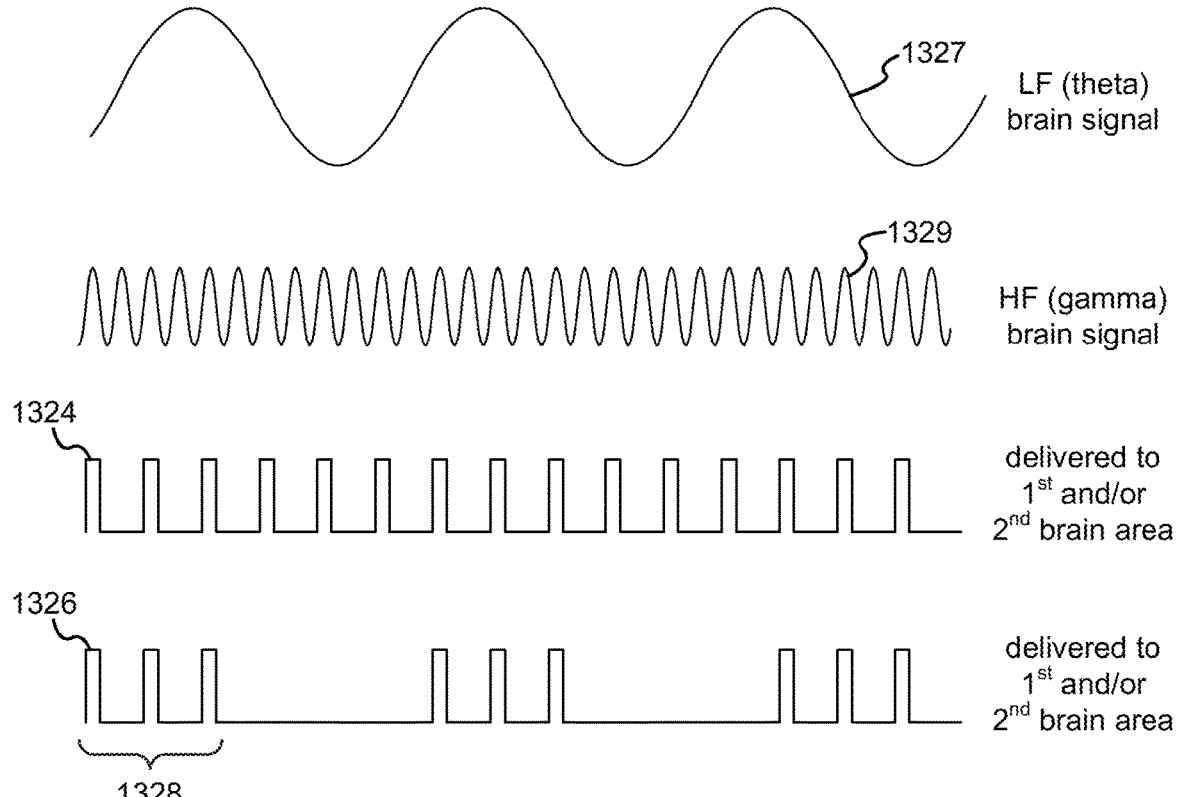

In yet another alternative stimulation strategy shown in FIG. 13E, to decrease the measure of phase-amplitude coupling at either of, or between two brain areas, the device may be configured to deliver electrical pulses 1324 to one or more selected brain areas at a frequency different from the frequencies of observed brain signals. In the case of theta-gamma coupling, the pulse frequency of the electrical pulses 1324 would be different from the frequency of a filtered theta brain wave 1327 and the frequency of a filtered gamma brain signal 1329. For example, the pulse frequency may be in a range between the 4-8 Hz theta range and the 25-200 Hz gamma range. In a variation of this stimulation strategy, the pulse frequency may change over time. For example, the pulse frequency may sweep through a number of different frequencies between the 4-8 Hz theta range and the 25-200 Hz gamma range.

In yet another alternative stimulation strategy also shown in FIG. 13E, to decrease the measure of phase-amplitude coupling at either of, or between two brain areas, the device may be configured to deliver electrical pulses 1326 to one or more selected brain areas in short bursts 1328, wherein the pulse frequency of the electrical pulses 1326 within a burst 1328, and the burst frequency at which pulse bursts 1328 are delivered, are each at a frequency different from the frequencies of observed brain signals. In the case of theta-gamma coupling, the pulse frequency of the electrical pulses 1326 within a burst 1328 and the burst frequency of the bursts 1328 would be different from the frequency of a filtered theta brain wave 1327 and the frequency of a filtered gamma brain signal 1329. In a variation of this stimulation strategy, one or more of the pulse frequency and the burst frequency may change over time. For example, each of the pulse frequency and the burst frequency may sweep through a number of different frequencies between the 4-8 Hz theta range and the 25-200 Hz gamma range.

Figure 13F:
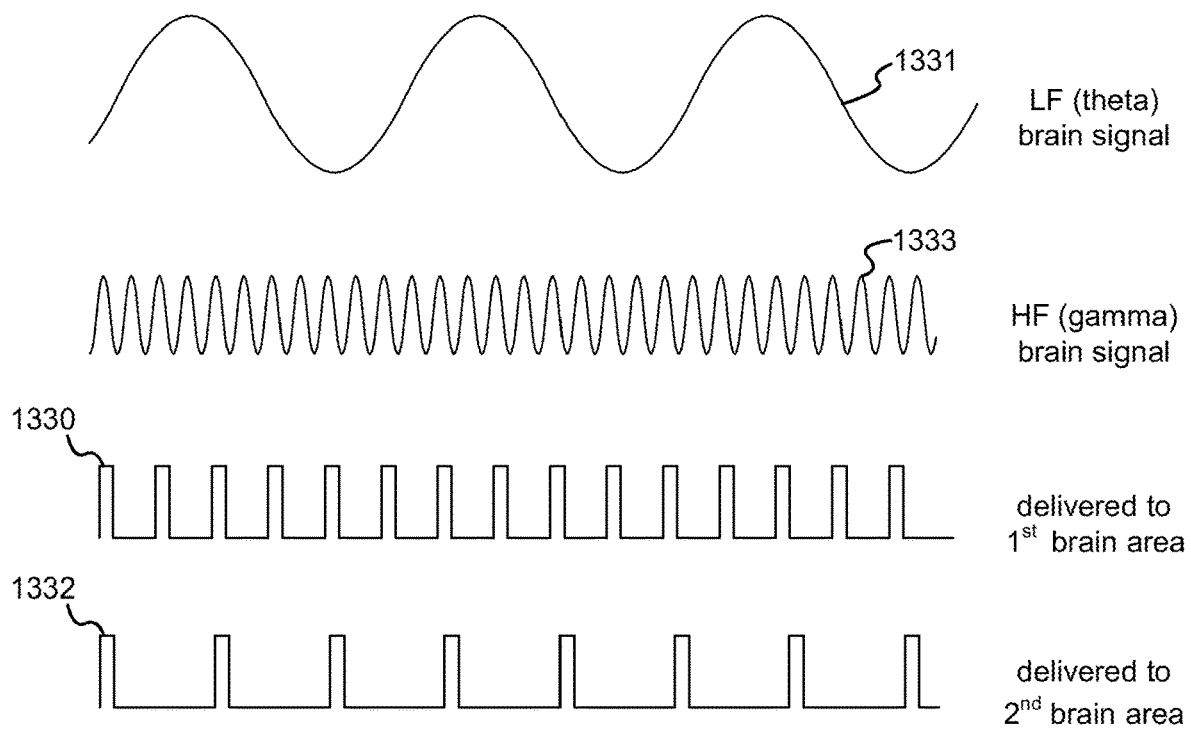

In another alternative stimulation strategy shown in FIG. 13F, to decrease the measure of phase-amplitude coupling at either of, or between two brain areas, the device may be configured to deliver electrical pulses 1330 to one selected brain area at a first pulse frequency that is different from the frequencies of observed brain signals, while simultaneously delivering electrical pulses 1332 to another selected brain area at a second pulse frequency that is different from the first frequency and also different from the frequencies of observed brain signals. In the case of theta-gamma coupling, the pulse frequency of the electrical pulses 1330 and the pulse frequency of the electrical pulses 1332 would each be different from the frequency of a filtered theta brain wave 1327 and the frequency of a filtered gamma brain signal 1329. For example, the first pulse frequency and the second pulse frequency may each be in a range between the 4-8 Hz theta range and the 25-200 Hz gamma range. In a variation of this stimulation strategy (not shown in FIG. 13F), the device may be configured to simultaneously deliver electrical pulses 1330 and electrical pulses 1332 to the same selected brain area(s). In another variation of this stimulation strategy, one or more of the first pulse frequency and the second pulse frequency may change over time. For example, each of the first pulse frequency and the second pulse frequency may sweep through a number of different frequencies between the 4-8 Hz theta range and the 25-200 Hz gamma range.

Figure 13G:
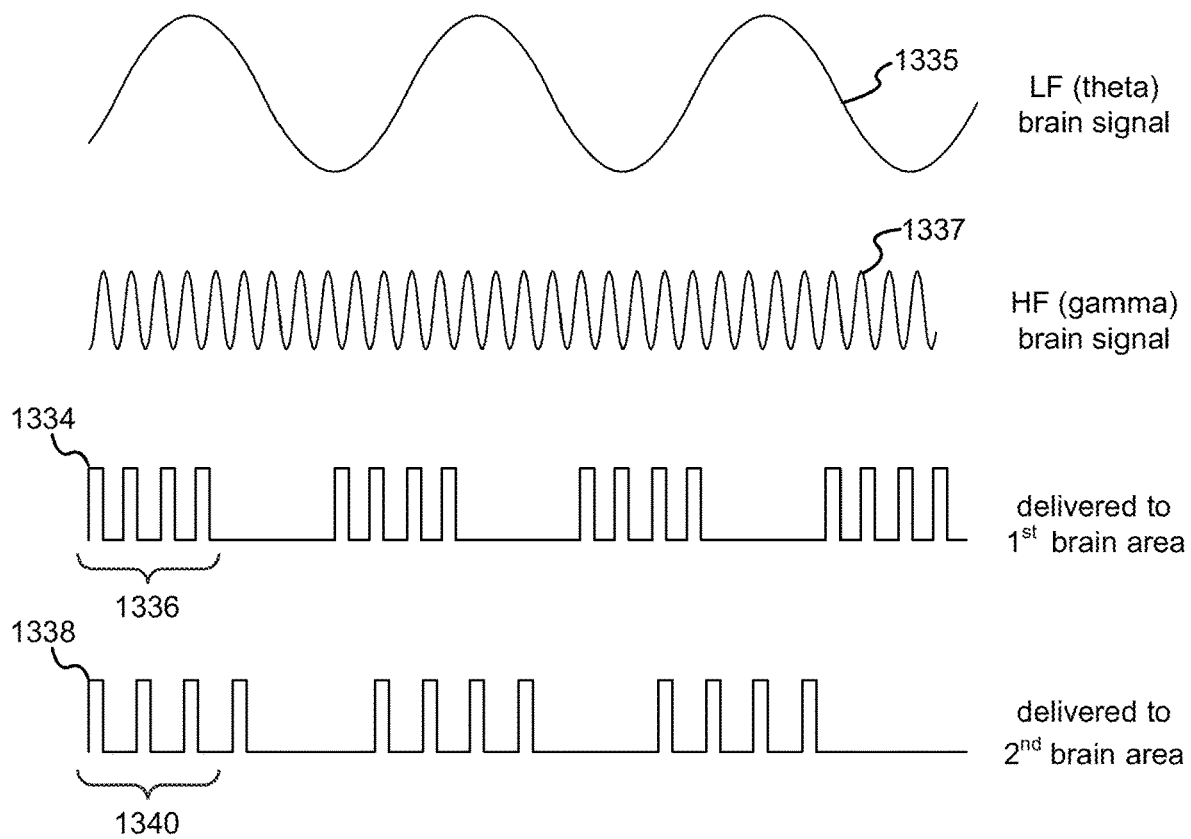

In another alternative stimulation strategy shown in FIG. 13G, to decrease the measure of phase-amplitude coupling at either of, or between two brain areas, the device may be configured to deliver electrical pulses 1334 to a selected brain area in short bursts 1336, wherein the pulse frequency of the electrical pulses 1334 within a burst 1336, and the burst frequency at which pulse bursts 1336 are delivered, are each at a frequency different from the frequencies of observed brain signals, while simultaneously delivering electrical pulses 1338 to another selected brain areas in short bursts 1340, wherein the pulse frequency of the electrical pulses 1338 within a burst 1340, and the burst frequency at which pulse bursts 1340 are delivered, are also each at a frequency different from the frequencies of observed brain signals. In the case of theta-gamma coupling, the pulse frequency of the electrical pulses 1334, the burst frequency of pulse bursts 1336, the pulse frequency of the electrical pulses 1332, and the burst frequency of pulse bursts 1340 would each be different from the frequency of a filtered theta brain wave 1327 and the frequency of a filtered gamma brain signal 1329. For example, each of the foregoing pulse frequencies and burst frequencies may be in a range between the 4-8 Hz theta range and the 25-200 Hz gamma range. In a variation of this stimulation strategy (not shown in FIG. 13G), the device may be configured to simultaneously deliver bursts 1336 of electrical pulses 1334 and bursts 1340 of electrical pulses 1338 to the same selected brain area(s). In another variation of this stimulation strategy, one or more of the foregoing pulse frequencies and burst frequencies may change over time. For example, each of the pulse frequencies and the burst frequencies may sweep through a number of different frequencies between the 4-8 Hz theta range and the 25-200 Hz gamma range.

One example of abnormal neural coupling may be abnormally decreased phase-amplitude coupling due to injury that may be due to stroke or traumatic brain injury. In this example, an implantable medical device may be configured to deliver electrical stimulation to increase the measure of phase-amplitude coupling between the injured area of the brain and other brain areas. For example, stimulation such as shown in FIG. 13A may be delivered to increase coupling between a region of motor cortex and sensory cortex, or between two regions of motor cortex. Alternatively, intermittent bursting stimulation as shown in FIG. 13B may be delivered to a single injured brain area to increase the measure of phase-amplitude coupling within that area. Measures of phase-amplitude coupling may then be used to assess changes in coupling and subsequently select or refine first and second PAC frequencies.

Another example of abnormal neural coupling may be abnormally increased phase-amplitude coupling in one or more brain areas due to a movement disorder such as Parkinson's disease, essential tremor, or dystonia, resulting in tremor, rigidity or freezing. In this example, an implantable medical device may be configured to measure phase-amplitude coupling between two or more brain areas that exhibit abnormal coupling, and electrical stimulation such as shown in FIG. 13D may be delivered that may decrease the observed phase-amplitude coupling between the affected brain areas.

Another example of abnormal neural coupling may be abnormal phase-amplitude coupling in one or more brain areas associated with any of the autistic spectrum disorders. In this example, an implantable medical device may be configured to decrease abnormally high phase-amplitude coupling, or increase abnormally low phase-amplitude coupling in one or more brain areas using one of the previously described stimulation strategies.

Other neurological disorders including but not limited to schizophrenia, depression, and mood disorders may be characterized by abnormal coupling within and between different brain areas. In these disorders, an implantable medical device may be configured to increase or decrease phase-amplitude coupling using one or more of the previously described stimulation strategies. These treatments may help normalize neural coupling and lead to clinical improvements.

Figure 14:
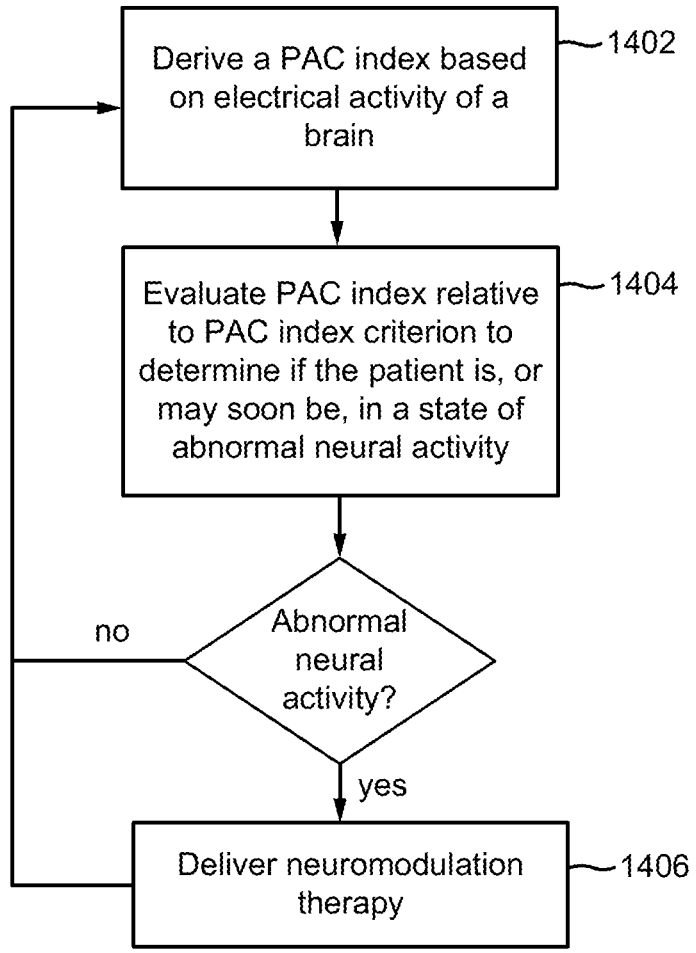
FIG. 14 is a flowchart of a method of delivering neuromodulation therapy based on measures of phase-amplitude coupling.

FIG. 14 is a flowchart of a method of delivering neuromodulation therapy based on measures of phase-amplitude coupling. The method may be implemented by the implantable neurostimulator and leads of FIG. 2.

In block 1402, the neurostimulator derives a PAC index based on electrical activity of a brain sensed with at least one sensor associated with a lead. The PAC index may correspond to a PAC score or may be derived from a plurality of PAC scores obtained over a period of time. The PAC index may be obtained from measures of phase-amplitude coupling computed in accordance with the methods described above with reference to FIGS. 3-11.

At block 1404, the neurostimulator evaluates the PAC index relative to a PAC index criterion to determine if the patient is, or may soon be, in a state of abnormal neural activity (e.g., seizure onset, poor memory quality, impaired cognitive processing, abnormal neural coupling). In some configurations, the PAC index criterion may be based on one or more measures of phase-amplitude coupling or PAC scores computed from brain signals sensed while a patient was experiencing abnormal neural activity (e.g., a seizure onset, memory loss, abnormal neural coupling). In this case, a PAC index that falls within a specified range, e.g., 5-10%, of the PAC index criterion or a series of PAC scores that are trending toward the PAC index criterion, may be a biomarker of abnormal neural activity. In other configurations, the PAC index criterion may be based on one or more measures of phase-amplitude coupling computed from brain signals sensed while patient was in a state of normal neural activity. In this case, a PAC index that falls outside a specified acceptable range, e.g., 5-10%, of the PAC index criterion or a series of PAC scores that are trending away from the PAC index criterion, may be a biomarker of abnormal neural activity.

At block 1406, if the neurostimulator determines that the patient is, or may soon be, in a state of abnormal neural activity, the neurostimulator delivers a neuromodulation therapy to the patient. Neuromodulation therapy in the form of electrical stimulation may be delivered to one or more areas of the brain in accordance with one or more of the stimulation strategies described above to bring about a desired change in subsequently derived PAC indices by either increasing phase-amplitude coupling or decreasing phase-amplitude coupling within an area of the brain or between two different areas of the brain.

After delivery of neuromodulation therapy, the process returns to block 1402, and is repeated. The process also returns to block 1402 if the if the neurostimulator determines that the patient is in a state of normal neural activity.

It should be observed that while the foregoing detailed description of various embodiments of the present invention is set forth in some detail, the invention is not limited to those details and an implantable medical device made according to the invention can differ from the disclosed embodiments in numerous ways. In particular, it will be appreciated that embodiments of the present invention may be employed in many different applications to measure phase-amplitude coupling in at least one portion of a patient's brain. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. An implantable medical device comprising:
   at least one sensor configured to be implanted in or on a brain, and to sense electrical activity of the brain;
   a data analyzer coupled to the at least one sensor and configured to:
      monitor an electrographic signal corresponding to the electrical activity of the brain sensed by the at least one sensor;
      for a selected portion of the electrographic signal, detect features of the electrographic signal that represent oscillations in a low frequency range, and features of the electrographic signal that represent oscillations in a higher frequency range; and
      determine a measure of phase-amplitude coupling between oscillations in the low frequency range and oscillations in the higher frequency range based on occurrences of oscillations in the higher frequency range which coincide with one or more phases of oscillations in the low frequency range; and
   a therapy subsystem coupled to the data analyzer, and configured to:
      receive the measure of phase-amplitude coupling from the data analyzer;
      process the measure of phase-amplitude coupling against a criterion; and
      initiate an action by the implantable medical device when the measure of phase-amplitude coupling satisfies the criterion, wherein the data analyzer determines a measure of phase-amplitude coupling by being further configured to:
for each detected feature in the low frequency range, assign a phase range to each of a plurality of portions of the detected feature;
for each portion of the detected feature, determine an individual metric based on a count of detected features in the higher frequency range that coincide with the portion;
for each assigned phase range, determine an aggregate metric based on the individual metrics determined for each portion of the detected feature having the phase range assigned thereto; and
determine the measure of phase-amplitude coupling based on a plurality of determined aggregate metrics.

2. The implantable medical device of claim 1, wherein the individual metric for a portion of the detected feature is weighted based on a characteristic of the detected feature.

3. The implantable medical device of claim 1, wherein the individual metric for a portion of the detected feature is normalized based on a measure of the duration of the portion.

4. The implantable medical device of claim 1, wherein the aggregate metric comprises a sum or a statistical measure of the individual metrics.

5. The implantable medical device of claim 1, wherein the measure of phase-amplitude coupling corresponds to an index that is a difference between a maximum of the plurality of determined aggregate metrics and a minimum of the plurality of determined aggregate metrics.

6. The implantable medical device of claim 1, wherein the selected portion of the electrographic signal corresponds to a portion of the electrographic signal that lies within a processing window having a specified duration.

7. An implantable medical device comprising:
at least one sensor configured to be implanted in or on a brain, and to sense electrical activity of the brain;
a data analyzer coupled to the at least one sensor and configured to:
monitor an electrographic signal corresponding to the electrical activity of the brain sensed by the at least one sensor;
for a selected portion of the electrographic signal, detect features of the electrographic signal that represent oscillations in a low frequency range, and features of the electrographic signal that represent oscillations in a higher frequency range; and
determine a measure of phase-amplitude coupling between oscillations in the low frequency range and oscillations in the higher frequency range based on occurrences of oscillations in the higher frequency range which coincide with one or more phases of oscillations in the low frequency range; and
a therapy subsystem coupled to the data analyzer, and configured to:
receive the measure of phase-amplitude coupling from the data analyzer;
process the measure of phase-amplitude coupling against a criterion; and
initiate an action by the implantable medical device when the measure of phase-amplitude coupling satisfies the criterion,
wherein the data analyzer is configured to:
detect features of the electrographic signal that represent oscillations in the low frequency range by applying the selected portion of the electrographic signal to a half wave detector programmed to detect half waves within the low frequency range, and
detect features of the electrographic signal that represent oscillations in the higher frequency range by applying the selected portion of the electrographic signal to a half wave detector programmed to detect half waves within the higher frequency range.

8. The implantable medical device of claim 7, wherein the data analyzer determines a measure of phase-amplitude coupling by being further configured to:
a) for each detected half wave within the low frequency range:
i) divide the detected half wave into a plurality of phase bins;
ii) assign a bin number to each of the plurality of phase bins, wherein the bin number is selected from a first set of bin numbers when the detected half wave has an upward slope, and from a second set of bin numbers when the detected half wave has a downward slope;
b) for each phase bin, determine an individual metric based on a number of detected half waves within the higher frequency range that coincide with the phase bin;
c) for each assigned bin number, determine an aggregate metric based on the individual metrics determined for each phase bin having the bin number assigned thereto; and
d) determine the measure of phase-amplitude coupling based on a plurality of determined aggregate metrics.

9. The implantable medical device of claim 8, wherein data analyzer is further configured to designate each of the detected half waves within the low frequency range is as: a) a qualified half wave, or b) an unqualified half wave, and each of the detected half waves within the higher frequency range is as: a) a qualified half wave, or b) an unqualified half wave.

10. The implantable medical device of claim 9, wherein the individual metric for each phase bin is either weighted or unweighted based on designations of the detected half wave within the low frequency range and the detected half waves within the higher frequency range.

11. The implantable medical device of claim 10, wherein:
the individual metric for a phase bin is weighted when the phase bin is part of an unqualified half wave within the low frequency range or when a detected half wave within the higher frequency range that coincides with the phase bin is an unqualified half wave, and
the individual metric for a phase bin is when the phase bin is part of a qualified half wave within the low frequency range and when each detected half wave within the higher frequency range that coincides with the phase bin is a qualified half wave.

12. The implantable medical device of claim 8, wherein:
the aggregate metric for an assigned bin number comprises a sum or a statistical measure of the individual metrics obtained for the assigned bin number, and
the determined measure of phase-amplitude coupling comprises an index that is a difference between an aggregate metric for a first bin number and an aggregate metric for a second bin number.

13. The implantable medical device of claim 1, wherein:
the low frequency range is one of: a delta frequency range of approximately 1 to 4 Hz, a theta frequency range of approximately 4 to 8 Hz, an alpha frequency range of approximately 8 to 13 Hz, and a beta frequency range of approximately 13 to 30 Hz, and the higher frequency range is one of: a theta frequency range of approximately 4 to 8 Hz, an alpha frequency range of approximately 8 to 13 Hz, a beta frequency range of approximately 13 to 30 Hz, and a gamma frequency range of approximately greater than 30 Hz.

14. The implantable medical device of claim 1, wherein the action modulates neural activity.

15. The implantable medical device of claim 1, wherein the action comprises one or more of: 1) a delivery of a therapy to a patient, and 2) a modification of one or more therapy parameters defining a therapy to be delivered to a patient.

16. The implantable medical device of claim 1, wherein the criterion is a threshold and the criterion is satisfied when the measure of phase-amplitude coupling exceeds the threshold.

17. The implantable medical device of claim 1, wherein the criterion is a threshold and the criterion is satisfied when the measure of phase-amplitude coupling is below the threshold.

18. A method of measuring phase-amplitude coupling comprising:
sensing electrical activity of a brain with at least one sensor implanted in or on the brain;
monitoring with an implanted data analyzer an electrographic signal corresponding to the electrical activity of the brain sensed by the at least one sensor;
for a selected portion of the electrographic signal, detecting with the implanted data analyzer features of the electrographic signal that represent oscillations in a low frequency range, and features of the electrographic signal that represent oscillations in a higher frequency range;
determining with the implanted data analyzer a measure of phase-amplitude coupling between oscillations in the low frequency range and oscillations in the higher frequency range based on occurrences of oscillations in the higher frequency range which coincide with one or more phases of oscillations in the low frequency range;
processing with an implanted therapy subsystem the measure of phase-amplitude coupling against a criterion; and
initiating with the implanted therapy subsystem an action when the measure of phase-amplitude coupling satisfies the criterion,
wherein determining a measure of phase-amplitude coupling comprises:
for each detected feature in the low frequency range, assigning a phase range to each of a plurality of portions of the detected feature;
for each portion of the detected feature, determining an individual metric based on a count of detected features in the higher frequency range that coincide with the portion;
for each assigned phase range, determining an aggregate metric based on the individual metrics determined for each portion of the detected feature having the phase range assigned thereto; and
determining the measure of phase-amplitude coupling based on a plurality of determined aggregate metrics.

19. A method of measuring phase-amplitude coupling comprising:
sensing electrical activity of a brain with at least one sensor implanted in or on the brain;
monitoring with an implanted data analyzer an electrographic signal corresponding to the electrical activity of the brain sensed by the at least one sensor;
for a selected portion of the electrographic signal, detecting with the implanted data analyzer features of the electrographic signal that represent oscillations in a low frequency range, and features of the electrographic signal that represent oscillations in a higher frequency range;
determine with the implanted data analyzer a measure of phase-amplitude coupling between oscillations in the low frequency range and oscillations in the higher frequency range based on occurrences of oscillations in the higher frequency range which coincide with one or more phases of oscillations in the low frequency range;
processing with an implanted therapy subsystem the measure of phase-amplitude coupling against a criterion; and
initiating with the implanted therapy subsystem an action when the measure of phase-amplitude coupling satisfies the criterion,
wherein:
detecting features of the electrographic signal that represent oscillations in a low frequency range comprises applying the selected portion of the electrographic signal to a half wave detector programmed to detect half waves within the low frequency range, and
detecting features of the electrographic signal that represent oscillations in a higher frequency range comprises applying the selected portion of the electrographic signal to a half wave detector programmed to detect half waves within the higher frequency range.

20. The method of claim 19, wherein determining a measure of phase-amplitude coupling comprises:
a) for each detected half wave within the low frequency range:
i) dividing the detected half wave into a plurality of phase bins;
ii) assigning a bin number to each of the plurality of phase bins, wherein the bin number is selected from a first set of bin numbers when the detected half wave has an upward slope, and from a second set of bin numbers when the detected half wave has a downward slope;
b) for each phase bin, determining an individual metric based on a number of detected half waves within the higher frequency range that coincide with the phase bin;
c) for each assigned bin number, determining an aggregate metric based on the individual metrics determined for each phase bin having the bin number assigned thereto; and
d) determining the measure of phase-amplitude coupling based on a plurality of determined aggregate metrics.

21. The method of claim 18, wherein the action modulates neural activity.

22. The method of claim 18, wherein initiating an action comprises one or more of: 1) delivering a therapy to a patient, and 2) modifying one or more therapy parameters defining a therapy to be delivered to a patient.

* * * * *